(12) United States Patent
Wolff et al.

(10) Patent No.: US 7,589,059 B2
(45) Date of Patent: *Sep. 15, 2009

(54) DELIVERY OF MOLECULES AND COMPLEXES TO MAMMALIAN CELLS IN VIVO

(75) Inventors: Jon A. Wolff, Madison, WI (US); Vladimir G. Budker, Middleton, WI (US); Hans Herweijer, Madison, WI (US); James E. Hagstrom, Middleton, WI (US); Sean D. Monahan, Madison, WI (US); Julia Hegge, Monona, WI (US); Vladimir Subbotin, Madison, WI (US)

(73) Assignee: Roche Madison Inc., Madison, WI (US)

( * ) Notice: Subject to any disclaimer, the term of this patent is extended or adjusted under 35 U.S.C. 154(b) by 878 days.

This patent is subject to a terminal disclaimer.

(21) Appl. No.: 10/628,792

(22) Filed: Jul. 28, 2003

(65) Prior Publication Data

US 2004/0023850 A1    Feb. 5, 2004

Related U.S. Application Data

(60) Provisional application No. 60/398,762, filed on Jul. 26, 2002.

(51) Int. Cl.
*A61K 38/00* (2006.01)
*A61K 38/08* (2006.01)
*C07K 14/00* (2006.01)

(52) U.S. Cl. .................. 514/2; 514/8; 514/12; 530/300; 530/350

(58) Field of Classification Search ................ None
See application file for complete search history.

(56) References Cited

U.S. PATENT DOCUMENTS

| | | | |
|---|---|---|---|
| 4,663,166 A * | 5/1987 | Veech | 424/663 |
| 5,346,696 A * | 9/1994 | Kim et al. | 424/85.4 |
| 5,521,291 A | 5/1996 | Curiel | |
| 5,580,859 A | 12/1996 | Felgner | |
| 5,583,020 A | 12/1996 | Sullivan | |
| 5,602,094 A * | 2/1997 | Goddard | 514/12 |
| 5,633,230 A * | 5/1997 | Twist et al. | 514/15 |
| 5,698,531 A | 12/1997 | Nabel | |
| 5,744,335 A | 4/1998 | Wolff et al. | |
| 5,922,687 A | 7/1999 | Mann | |
| 6,143,306 A * | 11/2000 | Donovan | 424/236.1 |
| 6,180,784 B1 | 1/2001 | Wolff et al. | |
| 7,144,869 B2 * | 12/2006 | Wolff et al. | 514/44 |
| 2001/0009904 A1 | 7/2001 | Wolff et al. | |
| 2002/0001574 A1 * | 1/2002 | Woiff et al. | 424/93.1 |
| 2002/0064520 A1 * | 5/2002 | Rozenberg et al. | 424/93.2 |
| 2003/0125281 A1 | 7/2003 | Lewis et al. | |
| 2003/0143204 A1 | 7/2003 | Lewis et al. | |

FOREIGN PATENT DOCUMENTS

WO      WO 99/31982      7/1999

OTHER PUBLICATIONS

Tanabe T, Pricer WE, Ashwell G, Subcellular Membrane Topology and Turnover of a Rat Hepatic Binding Protein Specific for Asialoglycoproteins, Journal of Biological Chemistry, 1979, 254(4): 1038-1043.*
Acsadi G et al. "Direct gene transfer and expression into rat heart in vivo" The New Biologist; 1991 vol. 3 No. 1 pp. 71-81.
Boulikas, Teni, "Gene Therapy to Human Diseases: Ex Vivo and In Vivo Studies (Review)." International Journal of Oncology; 1996; vol. 9; pp. 1239-1251.
Budker V et al. "Naked DNA delivered intraportally expresses efficiently in hepatocytes." Gene Therapy; 1996 vol. 3 No. 7 pp. 593-598.
Budker V et al. "The efficient expression of intravascularly delivered DNA in rat muscle," Gene Therapy; 1998 vol. 5 No. 2 pp. 272-276.
Chapman G et al. "Gene transfer into coronary arteries of intact animals with a percutaneous balloon catheter," Circ. Res; 1992 vol. 71 pp. 27-33.
Chowdhury JR et al. "Long-term improvement of hypercholesterolemia after ex vivo gene therapy in LDLR-deficient rabbits," Science; 1991 vol. 254 pp. 1802-1805.
Coll JL et al. "In Vivo Delivery to Tumors of DNA Complexed With Linear Polyethylenimine." Human Gene Therapy; 1999 vol. 10 pp. 1659-1666.
Ferry N et al. "Retroviral-mediated gene transfer into hepatocytes in vivo ," Proc Natl Acad Sci USA; 1991 vol. 88 pp. 8377-8381.
French, Brent A., et al., "Cellular and Molecular Cardiology: Percutaneous Transluminal In Vivo Gene Transfer by Recombinant Adenovirus in Normal Porcine Coronary Arteries, Atherosclerotic Arteries, and Two Models of Coronary Restenosis." Circulation; Nov. 1994; vol. 90(5); pp. 2402- 2413.
Greelish JP et al. "Stable restoration of the sarcoglycan complex in dystrophic muscle perfused with histamine and a recombinant adeno-associated viral vector." Nature; 1999 vol. 5 No. 4 pp. 439-443.
Hengge UR et al. "Cytokine gene expression in epidermis with biological effects following injection of naked DNA," Nature Genetics; 1995 vol. 10 pp. 161-166.
Hickman MA et al. "Gene expression following direct injection of DNA into liver," Human Gene Therapy; 1994 vol. 5 pp. 1477-1483.
Jaffe HA et al. "Adenovirus-mediated in vivo gene transfer and expression in normal rat liver," Nat. Genet; 1992 vol. 1 pp. 372-378.

(Continued)

*Primary Examiner*—Cecilia Tsang
*Assistant Examiner*—Julie Ha
(74) *Attorney, Agent, or Firm*—Kirk Ekena

(57) ABSTRACT

Disclosed is a system for providing in vivo delivery of molecules or complexes to extravascular mammalian cells using an intravascular administration route. The molecules or complexes are inserted in an injection solution into a mammalian vasculature. Insertion of the injection solution at an appropriate rate transiently increases the volume of extravascular fluid in the tissue thereby facilitating delivery of the molecule to the cell.

25 Claims, 22 Drawing Sheets

OTHER PUBLICATIONS

Kaleko M et al. "Persistent gene expression after retroviral gene transfer into liver cells in vivo," Hum Gene Ther; 1991 vol. 2 pp. 27-32.

Kaneda Y et al. "Increased expression of DNA cointroduced with nuclear protein in adult rat liver," Science; 1989 vol. 243 pp. 375-378.

Kaneda Y et al. "Introduction and expression of the human insulin gene in adult rat liver," J Biol Chem; 1989 vol. 264 pp. 12126-12129.

Kawabata K et al. "The Fate of Plasmid DNA After Intravenous Injection in Mice: Involvement of Scavenger Receptors in Its Hepatic Uptake." Pharmaceutical Research; 1995 vol. 12 No. 6 pp. 825-830.

Kay MA et al. "Hepatic gene therapy: persistent expression of human alpha 1-antitrypsin in mice after direct gene delivery in vivo," Hum Gene Ther; 1992 vol. 3 pp. 641-647.

Ledley FD et al. "Retroviral gene transfer into primary hepatocytes: implications for genetic therapy of liver-specific functions," PNAS; 1987 vol. 84 pp. 5335-5339.

Li Q et al. "Assessment of recombinant adenoviral vectors for hepatic gene therapy," Hum. Gene Ther; 1993 vol. 4 pp. 403-490.

Liu F et al. "Hydrodynamics-based transfection in animals by systemic administration of plasmid DNA." Gene Therapy; 1999 vol. 6 pp. 1258-1266.

Liu Y et al. "Cationic Liposome-Mediated Intravenous Gene Delivery." J Biol Chem; 1995 vol. 270 No. 42 pp. 24864-24870.

Malone RW et al. "Dexamethasone enhancement of gene expression after direct hepatic DNA injection," J Biol Chem; 1994 vol. 269 pp. 29903-29907.

Metrikin DC et al. "Intravitreal drug administration with depot devices." Curr Opin Ophthalmol; 1994 vol. 5 No. 3 pp. 21-29.

Meyer KB et al. "Intratracheal gene delivery to the mouse airway: characterization of plasmid DNA expression and pharmacokinetics," Gene Ther; 1995 vol. 2 pp. 450-460.

Milas M et al. "Isolated limb perfusion in the sarcoma-bearing rat: a novel preclinical gene delivery system," Clin Cancer Res; 1997 vol. 3 No. 12 Pt. 1, pp. 2197-2203.

Rekhter, Mark D. Md, Phd, Et al., "Graft Permeabilization Facilitates Gene Therapy of Transplant Arteriosclerosis in a Rabbit Model." Circulation; Sep. 29, 1998; vol. 98(13); pp. 1335-1341.

Rekhter, Mark D., Et al., "Gene Transfer Into Normal and Atherosclerotic Human Blood Vessels." Circ. Res.; 1998; vol. 82; pp. 1243-1252.

Riessen et al. "Arterial gene transfer using pure DNA applied directly to a hydrogel-coated angioplasty balloon," Human Gene Ther; 1993 vol. 4 pp. 749-758.

Ross, Gail, et al., "Gene Therapy in the United States: A Five-Year Status Report." Human Gene Therapy; Sep. 10, 1996; vol. 7; pp. 1781-1790.

Sikes M et al. "In vivo gene transfer into rabbit thyroid follicular cells by direct DNA injection," Hum. Gene Ther; 1994 vol. 5 p. 837-844.

Simari, Robert D., Et al., "Regulation of Cellular Proliferation and Intimal Formation Following Balloon Injury in Atherosclerotic Rabbit Arteries." Gene Therapy for Atherosclerotic Arteries; J. Clin. Invest.; Jul. 1996; vol. 98, No. 1; pp. 225-235.

Soriano P. et al. "Targeted and nontargeted liposomes for in vivo transfer to rat liver cells of a plasmid containing the preproinsulin i gene," PNAS; 1983 vol. 80 pp. 7128-7131.

Stratford-Perricaudet LD et al. "Evaluation of the transfer and expression in mice of an enzyme-encoding gene using a human adenovirus vector," Hum. Gene Ther; 1990 vol. 1 pp. 241-256.

Vile RG et al. "In vitro and in vivo targeting of gene expression to melanoma cells," Cancer Res; 1993 vol. 53 pp. 962-967.

Von Der Leyen, Heiko, E., Et al., "A Pressure-Mediatated Nonviral Method For Efficient Arterial Gene and Oligonucleotide Transfer." Human Gene Therapy 1999 vol. 10 pp. 2355-2364.

Wolff JA et al. "Direct gene transfer into mouse muscle in vivo," Science; 1990 vol. 247 pp. 1465-1468.

Wolff JA et al. "Expression of retrovirally transduced genes in primary cultures of adult rat hepatocytes," Proc Natl Acad Sci USA; 1987 vol. 84 pp. 3344-3348.

Zhang G et al. "Efficient Expression of Naked DNA Delivered Intraarterially to Limb Muscles of Nonhuman Primates." Hum Gene Ther; 2001 vol. 12 pp. 427-438.

Zhang G et al. "Expression of Naked Plasmid DNA Injected into the Afferent and Efferent Vessels of Rodent and Dog Livers." Human Gene Therapy; 1997 vol. 8 pp. 1763-1772.

Zhang G et al. "High Levels of Foreign Gene Expression in Hepatocytes after Tail Vein Injections of Naked Plasmid DNA." Hum Gene Ther; 1999 vol. 10 pp. 1735-1737.

Zhu N. et al. "Systemic Gene Expression After Intravenous DNA Delivery Into Adult Mice." Science; 1993 vol. 261 pp. 209-211.

Song J et al. "Influence of Injection Site, Microvascular Pressure and Ultrasound Variables on Microbubble-mediated Delivery of Microspheres to Muscle." J. Am. Coll. Cardiol. 2002 vol. 39 No. 4, pp. 726-731.

* cited by examiner

A.

B.

A.

B.

US 7,589,059 B2

DELIVERY OF MOLECULES AND COMPLEXES TO MAMMALIAN CELLS IN VIVO

CROSS-REFERENCE TO RELATED APPLICATIONS

This application claims the benefit of prior provisional application 60/398,762 filed on Jul. 26, 2002.

FIELD OF THE INVENTION

The invention relates to devices and processes for use in biological systems. More particularly, in vivo processes that provide for the delivery of compounds and complexes to extravascular mammalian cells are described.

BACKGROUND OF THE INVENTION

A basic challenge for drug delivery is to develop approaches for delivering molecules or complexes to cells of a patient in a way that is efficient and safe. To this end, a variety of methods and routes of administration have been developed to deliver pharmaceuticals that include small molecular drugs and biologically active compounds such as peptides, hormones, proteins, and enzymes to their site of action. Parenteral routes of administration include intravascular (intravenous, intra-arterial), intramuscular, intraparenchymal, intradermal, subdermal, subcutaneous, intratumor, intraperitoneal, and intralymphatic injections that use a syringe and a needle or catheter. The blood circulatory system, while providing systemic spread of a pharmaceutical, doesn't readily enable delivery of many molecules or complexes to parenchymal cells outside the blood vessels.

The controlled release of pharmaceuticals after their administration is also under intensive development. Polyethylene glycol and other hydrophilic polymers have provided protection of pharmaceuticals in the blood stream by preventing interaction with blood components, opsonization, phagocytosis and uptake by the reticuloendothelial system, thereby increasing the circulation time of the pharmaceutical. For example, the enzyme adenosine deaminase has been covalently modified with polyethylene glycol to increase its circulatory time and persistence in the treatment of patients with adenosine deaminase deficiency. Pharmaceuticals have also been complexed with a variety of biologically-labile polymers to delay their release from depots. Typical examples of biodegradable and non-degradable sustained release systems included copolymers of, respectively, poly(lactic/glycolic) acid (PLGA; Jain et al. 1998) and ethylvinyl acetate/ polyvinyl alcohol (Metrikin & Anand 1994).

Transdermal routes of administration have been effected by patches and ionotophoresis. 5 Other epithelial administration routes include oral, nasal, respiratory, and vaginal. These routes have attracted interest for the delivery of peptides, proteins, hormones, and cytokines, which are typically administered parenterally using needles. For example, the delivery of insulin via oral or nasal routes is attractive for patients with diabetes mellitus. Capsules and pH-sensitive hydrogels have been developed for oral delivery (Hu et al. 1999, Lowman et al. 1999).

Liposomes are also used as drug delivery vehicles for low molecular weight drugs such as adriamycin, an anticancer agent, and amphotericin B for systemic fungal infections. pH-sensitive polymers have been used in conjunction with liposomes for the triggered release of an encapsulated drug. For example, hydrophobically modified N-isopropylacrylamide-methacrylic acid copolymer can render regular egg phosphatidyl chloline liposomes pH-sensitive due to pH-dependent interaction of grafted aliphatic chains with lipid bilayers (Meyer et al. 1998).

A number of techniques have also been explored for delivery of DNA encoding therapeutic genes to cells in mammals, a process called gene therapy. These techniques include direct injection of naked DNA into tissue, especially muscle, the "gene gun", electroporation, the use of viral vectors, and cationic liposome and polymers. These techniques however, suffer from delivery to too few cells and/or toxicity. While highly effective in vitro, cationic DNA-containing complexes generally have been of limited success in vivo becuase their large size and positive charge has an adverse influence on biodistribution of the complexes.

SUMMARY OF THE INVENTION

We describe devices, processes and compositions for intravascular delivery of molecules and complexes to parenchymal cells of post-embryonic mammals. The invention provides improved in vivo delivery of a wide range of biologically active compounds. The efficiency of delivery is enhanced by injecting a sufficient volume at an appropriate rate into the lumen of a vessel thereby increasing movement of the molecule or complex out of the vessel and into extravascular parenchymal cells.

In a preferred embodiment, we describe an in vivo process for the delivery of molecules or complexes to parenchymal cells in a mammal comprising: injecting the molecules or complexes in a solution into a vessel, wherein the volume and rate of the injection results in increasing permeability of the vessel and transiently increasing the volume of extravascular fluid in the target tissue causing tissue swelling to provide for delivery of the molecules or complexes to cells outside the vessel. Increasing vessel permeability and increasing the volume of extravascular fluid in the target tissue may further comprise blocking the flow of fluid through vessels into and/ or out of a target tissue or area. A complex comprises: amphipathic compounds, polymers, viral and non-viral vectors and biologically active compounds The solution may contain a compound or compounds which may or may not associate with the molecule or complex and may aid in delivery.

In a preferred embodiment, processes are described for increasing the transit of a molecule or complex out of a vessel and into a surrounding tissue in a mammal in vivo comprising: injecting a sufficient volume of injection solution containing the molecule or complex into an afferent or efferent vessel of the target tissue, thus forcing fluid out of the vasculature into the extravascular space, transiently increasing the volume of extravascular fluid in the target tissue. For injection into an artery, the target tissue is the tissue that the artery supplies with blood. For injection into a vein, the target tissue is the tissue from which the vein drains blood. For injection into bile duct, the target tissue is the liver. The injection solution may further contain a compound or compounds which may aid in delivery and may or may not associate with the molecule or complex.

In a preferred embodiment, in vivo processes are described for delivering a molecule or complex to a mammalian cell comprising: inserting the molecule or complex in a solution into a vessel while impeding or occluding fluid flow through one or more vessels proximal to the point of injection and the target tissue. The occlusion may occur naturally in the mammal, or it may be artificial. The process includes impeding fluid flow through afferent and efferent vessels of the target tissue by applying external compression against mammalian skin. This compression includes applying a cuff over the skin, such as a sphygmomanometer or a tourniquet. Fluid flow through a vessel may also be impeded by clamping the vessel or by a balloon catheter placed within the vessel. The vessels are occluded for a period of time necessary to deliver the molecule or complex without causing ischemic damage to the tissue.

In a preferred embodiment, we describe a noninvasive device for enhancing intravascular delivery of molecules and complexes to mammalian cells comprising: an external cuff that applies compression to internal vessels thereby impeding fluid flow through the vessels in an area beneath the cuff. A cuff can be selected from the group consisting of: a sphygmomanometer and a tourniquet. The cuff impedes fluid flow out of an area or tissue when a solution is injected into a vessel at a point distal to the cuff resulting in increased permeability of the vessel to molecules or complexes present in the injection solution and increasing the volume of extravascular fluid in the tissue.

In a preferred embodiment, the molecule can be a macromolecule. The macromolecule may be selected from the list comprising: nucleic acid, protein and therapeutic compound. In another preferred embodiment, the molecule or complex can be neutral, cationic or anionic. In another preferred embodiment, the molecule or complex can have a zeta potential or surface charge that is neutral, cationic or anionic. Delivery of the molecule or complex may alter the endogenous properties of the cell. The molecule or complex may be delivered to a cell in order to produce a cellular change that is therapeutic. For example, the molecule or complex may be delivered to the mammalian cell for the treatment of a disease or infection.

In a preferred embodiment, the molecule or complex may be injected in a solution that contains low salt. Low-salt injections solutions provide better delivery of some molecules and complexes such as cationic molecules and complexes held together by electrostatic interactions. In another preferred embodiment, the molecule or complex may be injected in a solution that contains zwitterions. In another preferred embodiment, the injected solution may hypertonic or hypotonic.

In a preferred embodiment, the permeability of the vessel may be further increased by delivering to the mammal a compound which is known in the art to increase vessel permeability. Such compounds may be selected from the list comprising: histamine, vascular permeability factor, calcium channel blockers, beta-blockers, phorbol esters, ethylene-diaminetetraacetic acid, adenosine, papaverine, atropine, nifedipine, and hypertonic solutions.

In a preferred embodiment, we describe in vivo processes to deliver macromolecules to the liver. More specifically, we describe processes to deliver macromolecules to hepatocytes comprising: injection into portal vein, injection into hepatic vein, injection into inferior vena cava and injection into bile duct. Transient clamping of the hepatic vein/inferior vena cava and portal vein increase delivery efficiency. Injection solutions may be hypertonic.

In a preferred embodiment, the described devices and processes can be used to deliver a biologically active compound to a mammalian cell for the purpose of altering the endogenous properties of the cell. Altering the endogenous properties of the cell may be for therapeutic purposes, for facilitating pharmaceutical drug discovery, for facilitating drug target validation or for research. The mammal can be selected from the group comprising: mouse, rat, rabbit, dog, primate and human. The cell may be selected from the group comprising parenchymal cell, liver cell, spleen cell, heart cell, kidney cell, lung cell, skeletal muscle cell, diaphragm cell, prostate cell, skin cell, testis cell, fat cell, bladder cell, brain cell, pancreas cell, and thymus cell.

Panel D shows the merged pictures. Streptavidin-NLS is shown in black, actin and nuclei are shown in gray.

G. Distribution of β-galactosidase in mouse liver 60 minutes after delivery via injection into tail vein. β-galactosidase is shown in black, other cell features shown in gray and white.

H. Distribution of 20 nm polystyrene beads in mouse liver 60 minutes after delivery via injection into tail vein. Left panel (A) show beads only. Right panel (B) shows beads and actin. Beads are shown in black, actin and nuclei are shown in gray.

I. Distribution of 500 nm polystyrene beads in mouse liver 60 minutes after delivery via injection into tail vein. Beads are shown in darker gray, actin and nuclei are shown in lighter gray.

J. Distribution of BOBO-3 nucleic acid stain in mouse liver 60 minutes after insertion of injection solution into tail vein. Top panel (A) shows distribution of BOBO-3 following injection of dye in 2.5 ml Ringer's solution. Bottom panel (B) shows distribution of BOBO-3 following injection of dye in 0.25 ml Ringer's solution.

K. Distribution of Cy3-labeled SV40 NLS-peptide in mouse liver 60 minutes after delivery via injection into tail vein. Peptide is shown in black, actin and nuclei are shown in gray.

L. Distribution of FITC-labeled anti-NUP62 monoclonal antibody in mouse liver, 1 hour after injection of 2.5 ml solution containing 20 μg antibody into tail vein. FITC-IgG shown in black. Actin and DNA are shown in gray.

M. Distribution of T7 phage clone 20-6 particles in mouse liver 5 minutes after delivery via injection into tail vein. Panel A shows T7 20-6 phage injected in 2.5 ml injection volume. Panel B shows T7 20-6 phage injected in 0.25 ml injection volume. Phage, detected by indirect immuno-histochemistry, is shown in black, actin and nuclei are shown in gray.

Figure 7:
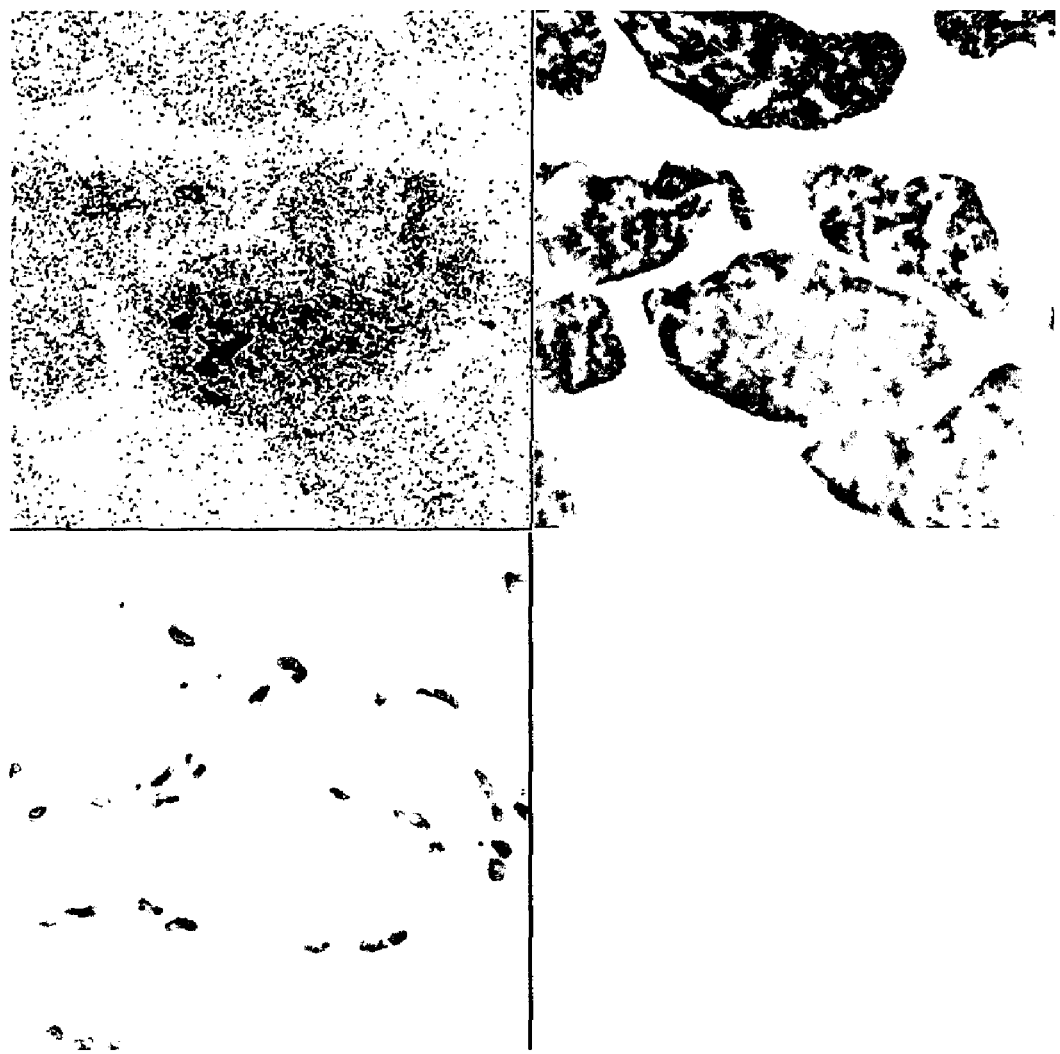

FIG. 7 Delivery of rhodamine-labeled dextran to limb skeletal muscle cells following venous injection. Top left panel shows rhodamine fluorescence. Top right panel shows autofluorescence to indicate cell location. Bottom left panel shows location of nuclei.

Figure 8A:
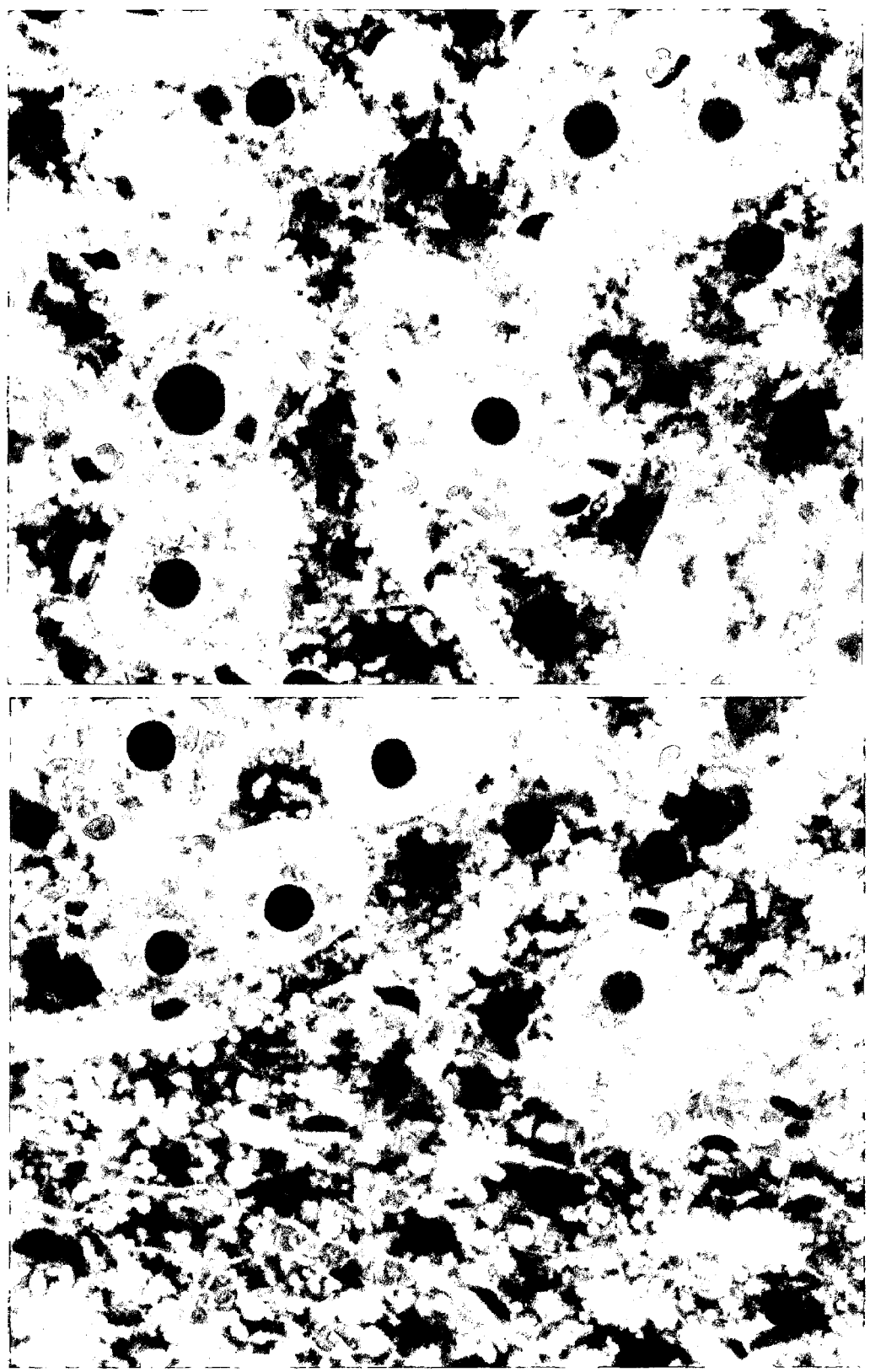
Figure 8B:
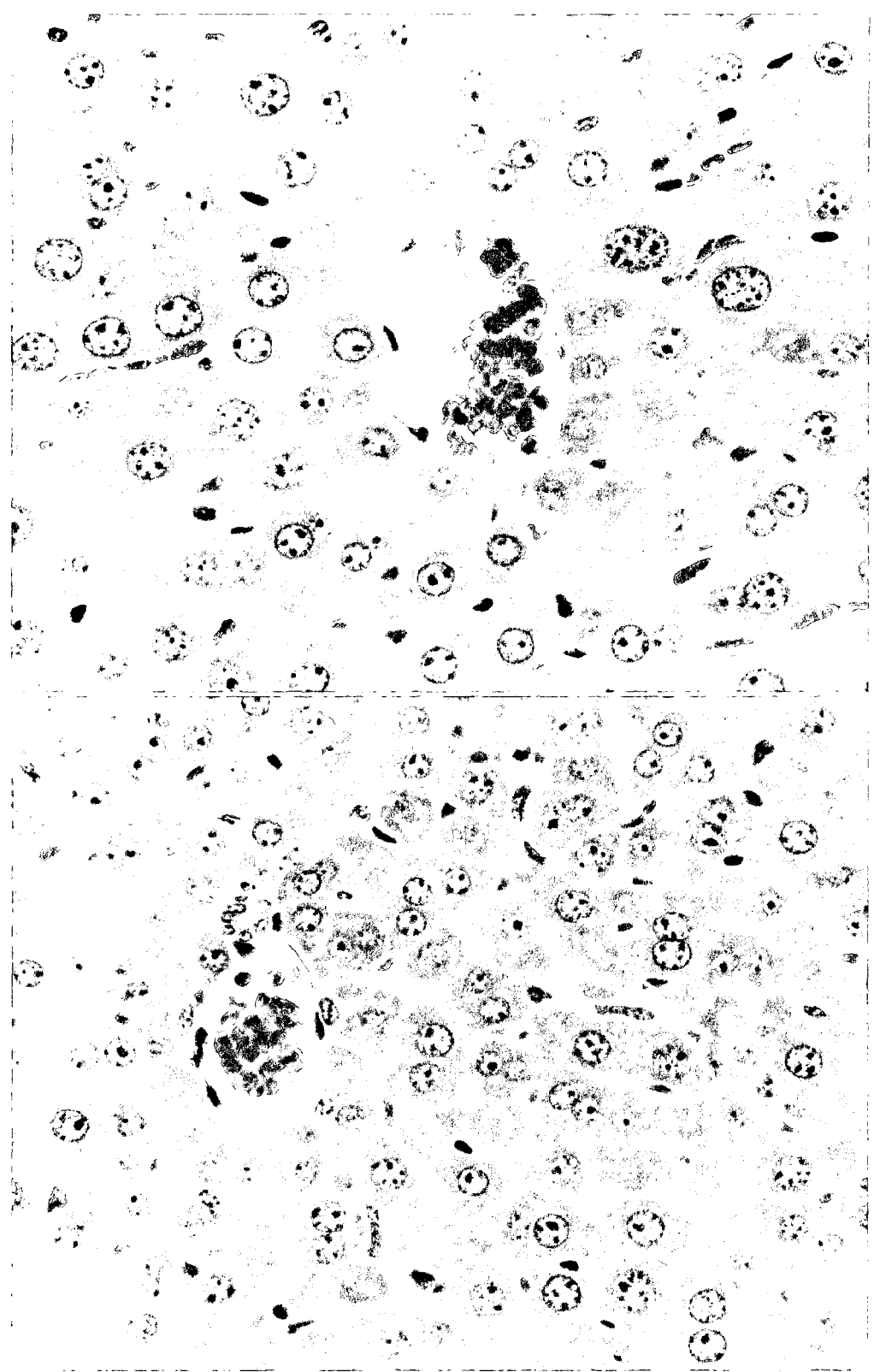

FIGS. 8A-8B.
A. Liver morphology immediately following injection of 2.5 ml Ringer's solution into tail vein of 25 g mice.
B. Liver morphology for control mouse that did not receive a tail vein injection.

Figure 9A:
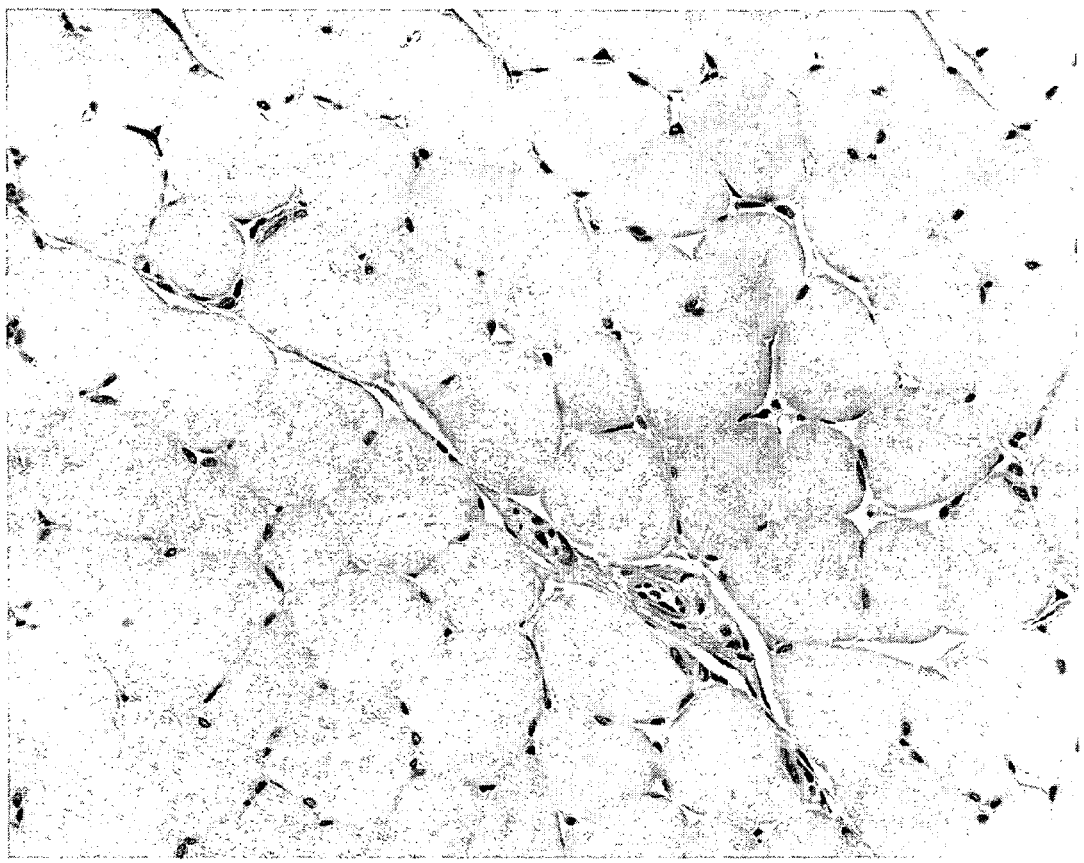
Figure 9B:
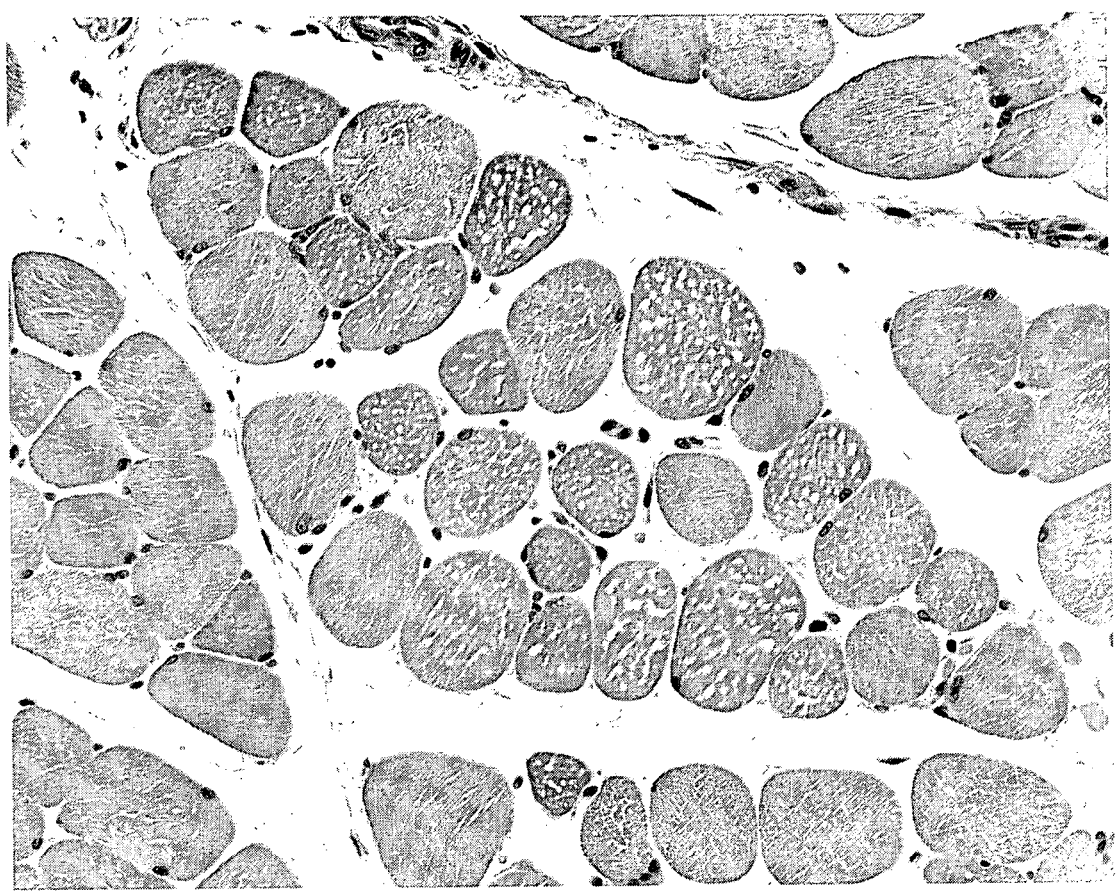
Figure 9C:
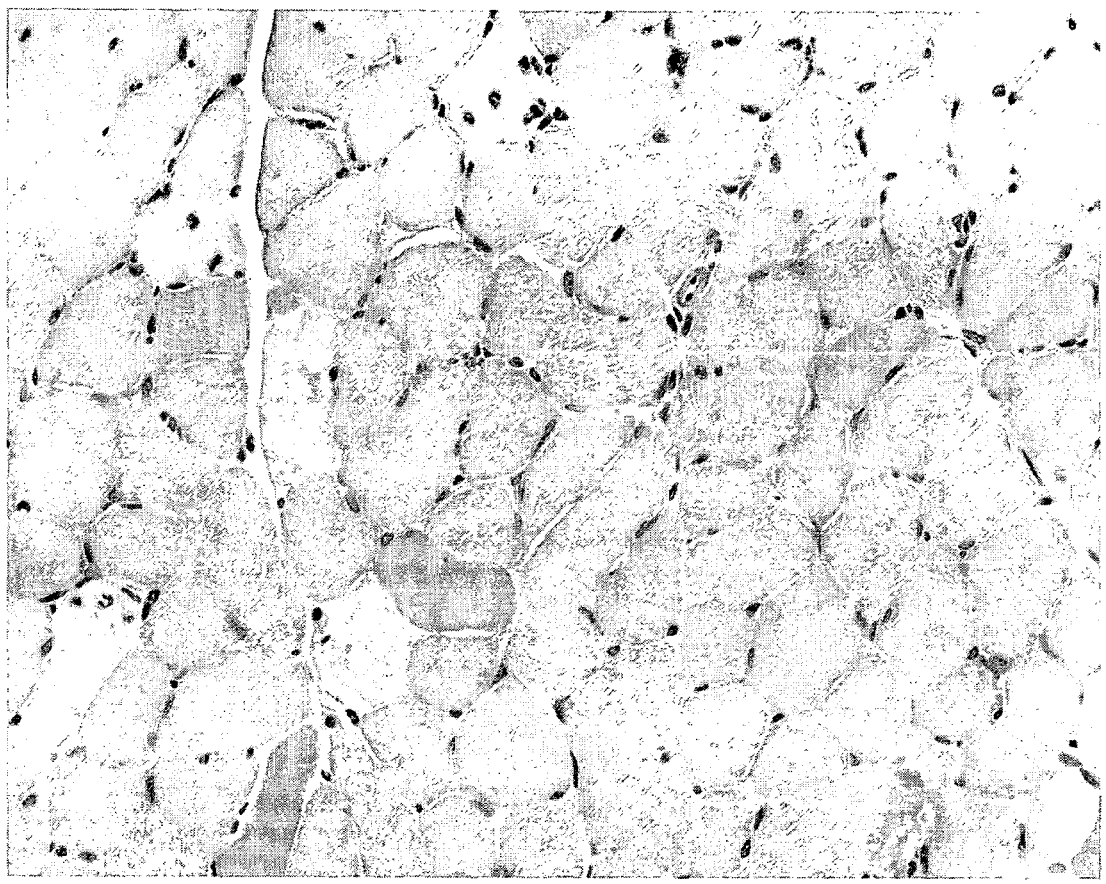

FIGS. 9A-9C.
A. Normal rat leg muscle.
B. Rat muscle 5 min after injection of 10 ml Ringer's solution into the Iliac artery.
C. Rat muscle 6 h after injection of 10 ml Ringer's solution into the Iliac artery.

DETAILED DESCRIPTION OF THE INVENTION

We have developed an intravascular process for the delivery of biologically active compounds to extravascular parenchymal cells. A key advancement is the enhanced delivery to a larger and more even distribution of cells than is achieved by direct parenchymal injections. Furthermore, using this process, we show delivery of cationic, anionic and charge neutral macromolecules and complexes to tissue cells outside a vessel following injection into the lumen of the vessel. More efficient delivery is achieved by increasing permeability of vessels and increasing the volume of extravascular fluid in a target area. Vessel permeability and extravascular fluid volume is increased by one or more of the following: using a sufficient volume of an appropriate injection solution, injecting the solution at an appropriate rate, impeding fluid flow into and out of the target tissue during the process, and increasing permeability of the vessel wall.

Many blood vessels naturally contain pores or fenestrae to allow passage of nutrients, etc. However, in most tissues these pores are too small-about 4 nm diameter-to allow extravasation of many potentially therapeutic molecules. In addition, potentially therapeutic cationic molecules have poor biodistribution because of electrostatic interactions with negatively charged serum components. Using the described processes, extravasation of fluid and molecules out of vessels and delivery to cells of the surrounding parenchyma is increased. We demonstrate increased delivery to many organs including: liver, kidney, heart, lung, skeletal muscle, prostrate, spleen, and diaphragm.

The term deliver means that the molecule or complex becomes associated with the cell thereby altering the endogenous properties of the cell. The molecule or complex can be on the membrane of the cell or inside the cytoplasm, nucleus, or other organelle of the cell. Other terms sometimes used interchangeably with deliver include transfect, transfer, or transform. In vivo delivery of a molecule or complex means to transfer the it from a container outside a mammal to near or within the outer cell membrane of a cell in the mammal. The delivery of a biologically active compound is commonly known as "drug delivery". A delivery system is the means by which a biologically active compound becomes delivered. The term encompasses all compounds, including the biologically active compound itself, and all processes required for delivery including the form and method of administration.

The described delivery system comprises an intravascular administration route. Vessels comprise internal hollow tubular structures connected to a tissue or organ within the body of an animal, including a mammal. Bodily fluid flows to or from the body part within the lumen of the tubular structure. Examples of bodily fluid include blood, lymphatic fluid, or bile. Vessels comprise: arteries, arterioles, capillaries, venules, sinusoids, veins, lymphatics, and bile ducts. Afferent vessels are directed towards the organ or tissue and in which fluid flows towards the organ or tissue under normal physiological conditions. Conversely, efferent vessels are directed away from the organ or tissue and in which fluid flows away from the organ or tissue under normal physiological conditions. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver. A vascular network consists of the directly connecting vessels supplying and/or draining fluid in a target organ or tissue.

A needle or catheter is used to inject the compound or complex into the vascular system. A catheter can be inserted at a distant site and threaded through the lumen of a vessel so that it resides in a vascular system that connects with a target tissue. The injection can also be performed using a needle that traverses the intact skin and enters the lumen of a vessel. For some target tissues, the injection solution can be injected into either an afferent vessel or an efferent vessel. For example, for delivery to the liver, the injection solution can be inserted into the hepatic artery or the portal vein or via retrograde injection into the hepatic vein. Similarly, for delivery to heart muscle cells, the injection solution can be inserted into either arteries or veins.

Efficient delivery via intravascular administration primarily depends on the volume of the injection solution and the injection rate. Vessel occlusion is also an important factor for delivery to many tissues. The composition of the injection solution can depend on the nature of the molecule or complex that is to be delivered. We have observed that certain complexes may be delivered more efficiently using low salt injection solutions. The use or hypertonic or hypotonic injection solutions or the use of vasodilators in the injection solution may further enhance delivery.

The choice of injection volume and rate are dependent upon: the size of the animal, the size of the vessel into with the solution is injected, the size and or volume of the target tissue, the bed volume of the target tissue vasculature, and the nature of the target tissue or vessels supplying the target tissue. For example, delivery to liver may require less volume because of the porous nature of the liver vasculature. The precise volume and rate of injection into a particular vessel, for delivery to a particular target tissue, may be determined empirically. Larger injection volumes and/or higher injection rates are typically required for a larger vessels, target sizes, etc. For example, efficient delivery to mouse liver may require injection of as little as 1 ml or less (animal weight ~25 g). In comparison, efficient delivery to dog or nonhuman primate limb muscle may require as much as 60-500 ml or more (animal weight 3-14 kg). Injection rates can vary from 0.5 ml/sec or lower to 4 ml/sec or higher, depending on animal size, vessel size, etc. Occlusion of vessels, by balloon catheters, clamps, cuffs, natural occlusion, etc, can limit or define the vascular network size or target area.

Because vasculature may not be identical from one individual to another, methods may be employed to predict or control appropriate injection volume and rate. Injection of iodinated contrast dye detected by fluoroscopy can aid in determining vascular bed size. Also, an automatic injection system can be used such that the injection solution is delivered at a preset pressure. For such a system, pressure may be measured in the injection apparatus, in the vessel into which the solution is injected, in a branch vessel within the target tissue, or within an efferent or afferent vessel within the target tissue.

Injecting into a vessel an appropriate volume at an appropriate rate increases permeability of the vessel to the injection solution and the molecules or complexes therein and increases the volume of extravascular fluid in the target tissue. Permeability can be further increased by occluding outflow of fluid (both bodily fluid and injection solution) from the tissue or local vascular network. For example, a solution is rapidly injected into an afferent vessel supplying an organ while the efferent vessel(s) draining the tissue is transiently occluded. Branching vessels may also be occluded. Natural occlusions may also be used. The afferent vessel is also transiently occluded proximal to the injection site. The vessels are partially or totally occluded for a period of time sufficient to allow delivery of a molecule or complex present in the injection solution. The occlusion may be released immediately after injection or may be released only after a determined length of time which does not result in tissue damage due to ischemia. Permeability is defined herein as the propensity for macromolecules to move out of a vessel and enter the extravascular space. One measure of permeability is the rate at which macromolecules move through the vessel wall and out of the vessel. Another measure of permeability is the lack of force that resists the movement of fluid or macromolecules through the vessel wall and out of the vessel. Endothelial cells lining the interior of blood vessels and connective material (e.g., collagen) both functional to limit permeability of blood vessels to macromolecules.

One method for occluding fluid flow is the application of an external cuff. The term cuff means a device for impeding fluid flow through mammalian vessels, particularly blood vessels. More specifically, a cuff refers to a device applied exterior to the mammal's skin and touches the skin in a non-invasive manner. The cuff applies external compression against the skin such that vessel walls, in an area underneath the cuff, are forced to constrict an amount sufficient to impede fluid from flowing through the vessels at a normal rate. Impeding fluid flow into and out of an area such as a limb, combined with injection of a solution distal to the cuff, causes vessel permeability and extravascular fluid volume to increase in the area. One example of a cuff is a sphygmomanometer which is normally used to measure blood pressure. Another example is a tourniquet. An exterior cuff may be applied prior to insertion of the injection solution, subsequent to insertion, or concurrent with insertion.

The described intra-arterial and intravenous processes require that blood flow be impeded for substantially less time than in required to cause tissue damage by ischemia. In fact, a common anesthesia for human limb surgery (e.g., carpal tunnel repair) involves the blockage of blood flow for more than one hour. We have not observed any widespread histological evidence of ischemic muscle damage in mice, rats, dogs, or primates following the described processes. The minimal elevations of muscle-derived enzymes found in serum provide significant evidence against any consequential muscle damage.

These techniques may be combined with other agents known in the art for increasing vascular permeability, including drugs or chemicals and hypertonic solutions. Drugs or chemicals can increase the permeability of the vessel by causing a change in function, activity, or shape of cells within the vessel wall; typically interacting with a specific receptor, enzyme or protein of the vascular cell. Other agents can increase permeability by changing the extracellular connective material. Examples of drugs or chemicals that may be used to increase vessel permeability include histamine, vascular permeability factor (VPF, which is also known as vascular endothelial growth factor, VEGF), calcium channel blockers (e.g., verapamil, nicardipine, diltiazem), beta-blockers (e.g., lisinopril), phorbol esters (e.g., PKC), ethylenediaminetetraacetic acid (EDTA), adenosine, papaverine, atropine, and nifedipine. Hypertonic solutions have increased osmolarity compared to the osmolarity of blood thus increasing osmotic pressure and causing cells to shrink. Typically, hypertonic solutions containing salts such as NaCl or sugars or polyols such as mannitol are used.

Molecules and complexes can be efficiently delivered into skeletal muscle cells in vivo via intravascular delivery. For example, up to 21% of all muscle cells in rat hind limbs express β-galactosidase after injection of 500 µg pCI-LacZ plasmid DNA in 10 ml saline into the iliac artery (Zhang et al. Human Gene Therapy 2001). Similar experiments in pig heart demonstrated that cardiac tissue can be efficiently transfected following injection of 1.5 mg plasmid DNA in 30 ml saline. Delivery of plasmid DNA to heart muscle cells, as determined by luciferase expression, is equally efficient following injection into coronary arteries or veins.

In the heart, efficient delivery through a coronary vein does not require occluding free blood flow through the corresponding artery. In this case, the microcapillary bed generates sufficient resistance to increase vessel permeability following solution injection. In ischemic heart, blocked arteries may help to increase delivery by occluding fluid flow through the artery. For insertion of the injection solution, percutaneous transluminal coronary angioplasty (PTCA) catheters may be advanced into the coronary venous system from a peripheral vein. Double lumen balloon catheters may be used to both insert the solution and occlude the vessel.

Delivery to the liver by injection into the hepatic vein is an example of retrograde delivery. As demonstrated in the examples that follow, injections are directed into the inferior cava which is clamped both proximally and distally to the entry of the hepatic vein into the inferior vena cava. Specifically, the downstream inferior vena cava clamp is placed between the diaphragm and the entry point of the hepatic vein. The upstream inferior vena cava clamp is placed just upstream of the entry point of the renal veins. The hepatic artery, mesenteric artery, renal vein and portal vein can also be occluded (i.e., clamped).

In the examples, we demonstrate the effectiveness of the described processes in delivering molecules to hepatocytes. Furthermore, we demonstrate successful delivery to hepatocytes via both blood vessel and bile duct administration routes. Hepatocytes are functionally polarized cells in which the basal and apical membranes have different exocytic, endocytic and transcytotic functions. Nevertheless, delivery to both the basal (sinusoidal) and apical (bile canalicular) sides was successful.

It may be beneficial for multiple vessels connecting to a single target tissue to be injected, either simultaneously or sequentially. For example, for delivery to liver, injections solutions may be inserted into both the bile duct and the portal vein.

It is envisioned that the described processes may be used repetitively in a single mammal. Multiple injections may be used to provide delivery to additional tissues, to increase delivery to a single tissue, or where multiple treatments are indicated.

The processes are shown to be effective in mice, rats, dogs, pig, and non-human primates. That delivery is observed in each of these animals strongly suggests that the processes are generally applicable to all mammals. In particular, the effectiveness of the processes in delivering molecules and complexes to nonhuman primates indicates that the processes will also be successful in humans.

The described processes may be combined with other delivery vehicles or vectors or other delivery enhancing groups. Such delivery vehicles and groups comprise: transfection reagents, viral vectors, non-viral vectors, lipids, polymers, polycations, amphipathic compounds, targeting signals, nuclear targeting signals, and membrane active compounds.

Delivery may also by improved by the use of targeting signals; enhance binding to receptors, cytoplasmic transport to the nucleus and nuclear entry (nuclear localizing signals) or release from endosomes or other intracellular vesicles. Cellular receptor signals are any signal that enhances the association of the gene with a cell, including ligands and non-specific cell binding. A targeting signal can be a protein, peptide, lipid, steroid, sugar, carbohydrate, nucleic acid or synthetic compound.

definitions

Biologically active compound: A biologically active compound is a compound having the potential to react with biological components. More particularly, biologically active compounds utilized in this specification are designed to change an endogenous property associated with a living cell. For purposes of this specification, an endogenous property is a property that is associated with a cell before delivery of the biologically active compound. In this specification, the cellular production of, or inhibition of a material, such as a protein, caused by a human assisting a molecule to an in vivo cell is an example of a delivered biologically active compound. Biologically active compounds may be selected from the list comprising: pharmaceuticals, proteins, peptides, polypeptides, enzyme inhibitors, hormones, cytokines, antigens, viruses, oligonucleotides, enzymes and nucleic acids.

Complex: Two molecules are combined to form a complex—through a process called complexation or complex formation—if they are in contact with one another through noncovalent interactions such as electrostatic interactions, hydrogen bonding interactions, and hydrophobic interactions. An interpolyelectrolyte complex is a noncovalent interaction between polyelectrolytes of opposite charge.

Parenchymal Cells: Parenchymal cells are the distinguishing cells of a gland, organ or tissue contained in and supported by the connective tissue framework. The parenchymal cells typically perform a function that is unique to the particular organ. The term "parenchymal" often excludes cells that are common to many organs and tissues such as fibroblasts and endothelial cells within the blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that present at least one side to a hepatic sinusoid and an apposed side to a bile canaliculus. Cells in the liver that are not parenchymal cells include the endothelial cells or fibroblast cells within the blood vessels.

In striated muscle, the parenchymal cells include myoblasts, satellite cells, myotubules, and myofibers. In cardiac muscle, the parenchymal cells include the myocardium (also known as cardiac muscle fibers or cardiac muscle cells) and the cells of the impulse connecting system such as those that constitute the sinoatrial node, atrioventricular node, and atrioventricular bundle.

In a pancreas, the parenchymal cells include cells within the acini such as zymogenic cells, centroacinar cells, basal or basket cells and cells within the islets of Langerhans such as alpha and beta cells.

In spleen, thymus, lymph nodes and bone marrow, the parenchymal cells include reticular cells and blood cells (or precursors to blood cells) such as lymphocytes, monocytes, plasma cells and macrophages.

In the nervous system which includes the central nervous system (the brain and spinal cord) peripheral nerves, and ganglia, the parenchymal cells include neurons, glial cells, microglial cells, oligodendrocytes, Schwann cells, and epithelial cells of the choroid plexus.

In a kidney, parenchymal cells include cells of collecting tubules and the proximal and distal tubular cells.

In the prostate, the parenchyma includes epithelial cells.

In glandular tissues and organs, the parenchymal cells include cells that produce hormones. In the parathyroid glands, the parenchymal cells include the principal cells (chief cells) and oxyphilic cells. In a thyroid gland, the parenchymal cells include follicular epithelial cells and parafollicular cells. In adrenal glands, the parenchymal cells include the epithelial cells within the adrenal cortex and the polyhedral cells within the adrenal medulla.

In the gastrointestinal tract, including the esophagus, stomach, and intestines, the parenchymal cells include epithelial cells, glandular cells, basal, and goblet cells.

In a lung, the parenchymal cells include the epithelial cells, mucus cells, goblet cells, and alveolar cells.

In fat tissue, the parenchymal cells include adipose cells or adipocytes.

In skin, the parenchymal cells include the epithelial cells of the epidermis, melanocytes, cells of the sweat glands, and cells of the hair root.

In cartilage, the parenchyma includes chondrocytes. In bone, the parenchyma includes osteoblasts, osteocytes, and osteoclasts.

Transfection Reagent: A transfection reagent or delivery vehicle is a compound or compounds that bind(s) to or complex(es) with oligonucleotides, polynucleotides, or other desired compounds and mediates their entry into cells. Examples of transfection reagents include, but are not limited to, cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents. Typically, the transfection reagent has a component with a net positive charge that binds to the oligonucleotide's or polynucleotide's negative charge. The transfection reagent may mediate binding of oligonucleotides and polynucleotides to cells via positive charge or via ligands that bind to receptors in the cell. For example, cationic liposomes or polylysine complexes have net positive charges that enable them to bind to nucleic acid.

Distal and proximal: For efferent vessels, distal is defined as upstream relative to the normal direction of fluid flow (i.e. the direction of increased branching, or toward the capillaries for blood vessels). For efferent vessels, proximal is defined as downstream relative to the normal direction of fluid flow. For afferent vessels, distal is defined as downstream relative to the normal direction of fluid flow (i.e. the direction of increased branching, or toward the capillaries for blood vessels). For afferent vessels, proximal is defined as upstream relative to the normal direction of fluid flow.

Cell targeting signals are any signals that enhance the association of the biologically active compound with a cell. These signals can modify a biologically active compound such as drug or nucleic acid and can direct it to a cell location (such as tissue) or location in a cell (such as the nucleus) either in culture or in a whole organism. The signal may increase binding of the compound to the cell surface and/or its association with an intracellular compartment. By modifying the cellular or tissue location of the foreign gene, the function of the biologically active compound can be enhanced. The cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. A variety of ligands have been used to target drugs and genes to cells and to specific cellular receptors. The ligand may seek a target within the cell membrane, on the cell membrane or near a cell. Binding of ligands to receptors typically initiates endocytosis. Ligands include agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and oth-er vitamins can also be used for targeting. Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active compound to certain parts of the cell.

Nuclear localizing signals enhance the targeting of the pharmaceutical into proximity of the nucleus and/or its entry into the nucleus during interphase of the cell cycle. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. Other NLS peptides have been derived from the hnRNP A1 protein, nucleoplasmin, c-myc, etc.

Many biologically active compounds, in particular large and/or charged compounds, are incapable of crossing biological membranes. In order for these compounds to enter cells, the cells must either take them up by endocytosis, i.e., into endosomes, or there must be a disruption of the cellular membrane to allow the compound to cross. In the case of endosomal entry, the endosomal membrane must be disrupted to allow for movement out of the endosome and into the cytoplasm. Either entry pathway into the cell requires a disruption of the cellular membrane. Compounds that disrupt membranes or promote membrane fusion are called membrane active compounds. These membrane active compounds, or releasing signals, enhance release of endocytosed material from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides. The control of when and where the membrane active compound is active is crucial to effective transport. If the membrane active agent is operative in a certain time and place it would facilitate the transport of the biologically active compound across the biological membrane. If the membrane active compound is too active or active at the wrong time, then no transport occurs or transport is associated with cell rupture and cell death. Nature has evolved various strategies to allow for membrane transport of biologically active compounds including membrane fusion and the use of membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Another functional group comprises compounds, interaction modifiers, change the way that a molecule interacts with itself or other molecules, relative to molecule containing no interaction modifier. The result of this modification is that self-interactions or interactions with other molecules are either increased or decreased. Polyethylene glycol is an interaction modifier that decreases interactions between molecules and themselves and with other molecules. Dimethyl maleic anhydride modification or carboxy dimethylmaleic anhydride modification are other examples of interaction modifiers. Such groups can be useful in limiting interactions such as between serum factors and the molecule or complex to be delivered. They may also reversibly inhibit or mask an activity or function of a compound.

A salt is any compound containing ionic bonds, (i.e., bonds in which one or more electrons are transferred completely from one atom to another). Salts are ionic compounds that dissociate into cations and anions when dissolved in solution and thus increase the ionic strength of a solution. Pharmaceutically acceptable salt means both acid and base addition salts.

Pharmaceutically acceptable acid addition salts are those salts which retain the biological effectiveness and properties of the free bases, and are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, ftimaric acid, tartaric acid, citric acid, benzoic acid, mandelic acid, methanesulfonic acid, ethansulfonic acid, p-toluenesulfonic acid, salicylic acid, trifluoroacetic acid, and the like. Pharmaceutically acceptable base addition salts are those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

EXAMPLES

1. Delivery of Plasmid DNA and Complexes using Different Injection Solutions:

A. Delivery of pDNA, Polycation/pDNA, and Polycation/Lipid/pDNA Complexes in a Glucose Solution via Mouse Tail Vein Injection. An injection solution was prepared consisting of 290 mM glucose (Sigma Chemical Company), 5 mM Hepes (Sigma Chemical Company), adjusted to pH 7.5.

Complexes were prepared as follows:

Complex I. pDNA (30 µg, 15 µL of a 2 µg/µL solution in water) was added to 7.5 mL of injection solution.

Complex II. pDNA (30 µg, 15 µL of a 2 µg/µL solution in water) was added to 7.5 mL of injection solution. To this solution was added Histone H1 (180 µg, 18 µL of a 10 mg/mL solution in water, Sigma Chemical Company), and the sample was mixed.

Complex III. pDNA (30 µg, 15 µL of a 2 µg/µL solution in water) was added to 7.5 mL of injection solution. To this solution was added Histone H1 (180 µg, 18 µL of a 10 mg/mL solution in water), and the sample was mixed. To this sample was added lipid MC789 (285 µg, 2.8 µL of a 100 mg/mL solution in ethanol) and the sample was again mixed.

Complex IV. pDNA (30 µg, 15 µL of a 2 µg/µL solution in water) was added to 7.5 mL of injection solution. To this solution was added Histone Hi (180 µg, 18 µL of a 10 mg/mL solution in water), and the sample was mixed. To this sample was added lipid MC789 (285 µg, 2.8 µL of a 100 mg/mL solution in ethanol) and the sample was again mixed. To this sample was added polyanion MC757 (45 µg, 4.5 µL of a 10 mg/mL solution in water) and the sample was again mixed.

Complex V. pDNA (30 µg, 15 µL of a 2 µg/µL solution in water) was added to 7.5 mL of injection solution. To this solution was added Histone H1 (180 µg, 18 µL of a 10 mg/mL solution in water), and the sample was mixed. To this sample was added lipid MC775 (264 µg, 2.6 µL of a 100 mg/mL solution in ethanol) and the sample was again mixed.

Complex VI. pDNA (30 µg, 15 µL of a 2 µg/µL solution in water) was added to 7.5 mL of injection solution. To this solution was added Histone H1 (180 µg, 18 µL of a 10 mg/mL solution in water), and the sample was mixed. To this sample was added lipid MC775 (264 µg, 2.6 µL of a 100 mg/mL solution in ethanol) and the sample was again mixed. To this sample was added polyanion MC 757 (45 µg, 4.5 µL of a 10 mg/mL solution in water) and the sample was again mixed.

Tail vein injections of 1.0 mL per 10 g body weight were preformed on ICR mice (n=2) using a 30 gauge, 0.5 inch needle. Injections were done manually with injection times of 4-5 sec [Zhang et al. 1999; Liu et al. 1999]. One day after injection, the livers were harvested and homogenized in lysis buffer (0.1% Triton X-100, 0.1 M K-phosphate, 1 mM DTT, pH 7.8). Insoluble material was cleared by centrifugation and 10 pl of the cellular extract or extract diluted 10× was analyzed for luciferase activity as previously reported [Wolff et al 1990]. The results indicate that cationic DNA-containing complexes as well as naked DNA are able to be delivered to the liver when injected in 290 mM glucose/5 mM Hepes (Table 1).

TABLE 1

| Complex | Luciferase Activity (RLUs) | |
|---|---|---|
| | n1 | n2 |
| Complex I | 76,412,780 | 59,123,910 |
| Complex II | 97,134,700 | 113,727,530 |
| Complex III | 28,318,350 | |
| Complex IV | 8,585,370 | 492,640 |
| Complex V | 66,334,090 | 81,762,590 |
| Complex VI | 2,895,850 | 1,372,190 |

B. Delivery of Fresh and Aged Cationic Polymer/pDNA Complexes via Mouse Tail Vein Injection Using a Glucose Solution. An injection solution was prepared consisting of 290 mM glucose, 5 mM Hepes, adjusted to pH 7.5.

Complexes were prepared as follows:

Complex I. pDNA (45 µg, 22.5 µL of a 2 µg/µL solution in water) was added to 11.25 mL of injection solution.

Complex II. pDNA (45 µg, 22.5 µL of a 2 µg/µL solution in water) was added to 11.25 mL of injection solution. To this solution was added Histone H1 (270 µg, 27 µL of a 10 mg/mL solution in water), and the sample was mixed.

Complex III. pDNA (45 µg, 22.5 µL of a 2 µg/µL solution in water) was added to 11.25 mL of injection solution. To this solution was added Histone H1 (270 µg, 27 µL of a 10 mg/mL solution in water), and the sample was mixed. The sample was kept at room temperature for 4 hours.

Complex IV. pDNA (45 µg, 22.5 µL of a 2 µg/µL solution in water) was added to 11.25 mL of injection solution. To this solution was added poly-L-lysine (144 µg, 14.4 µL of a 10 mg/mL solution in water, 30,000 MW, Sigma Chemical Company), and the sample was mixed.

Complex V. pDNA (45 µg, 22.5 µL of a 2 µg/µL solution in water) was added to 11.25 mL of injection solution. To this solution was added poly-L-lysine (144 µg, 14.4 µL of a 10 mg/mL solution in water, 30,000 MW), and the sample was mixed. The sample was kept at room temperature for 4 hours.

Complex V. pDNA (45 μg, 22.5 μL of a 2 μg/μL solution in water) was added to 11.25 mL of injection solution. To this solution was added Histone H1 (270 μg, 27 μL of a 10 mg/mL solution in water), and the sample was mixed. To this sample was added lipid MC789 (90 μg, 9 μL of a 10 mg/mL solution in ethanol) and the sample was again mixed.

Injections and liver luciferase expression were determined as describe above. The results indicate that both the fresh and the aged cationic polymer/DNA complexes can be delivered to the liver and the encoded luciferase gene is expressed (Table 2).

TABLE 2

| Complex | Luciferase Activity (RLUs) | | | |
|---|---|---|---|---|
| | n1 | n2 | n3 | n4 |
| Complex I | 844,151,800 | 1,898,668,800 | 836,979,800 | 1,235,543,400 |
| Complex II | 656,230,300 | 303,325,400 | 652,809,400 | 731,561,800 |
| Complex III | 439,707,500 | 385,641,500 | 932,924,700 | 483,757,500 |
| Complex IV | 655,707,600 | 492,613,700 | 681,753,300 | 532,753,000 |
| Complex V | 414,040,500 | 989,403,700 | 1,344,203,700 | 699,971,800 |
| Complex VI | 5,806,569 | 7,983,796 | 907,608,800 | |

C. Delivery of a Variety of Cationic Polymer/pDNA Complexes via Mouse Tail Vein Injection Using a Glucose Solution. An injection Solution was prepared consisting of 290 mM glucose, 5 mM Hepes, adjusted to pH 7.5.

Complexes were prepared as follows:

Complex I. pDNA (45 μg, 22.5 μL of a 2 μg/μL solution in water) was added to 11.25 mL of injection solution.

Complex II. pDNA (45 μg, 22.5 μL of a 2 gg/gL solution in water) was added to 11.25 mL of injection solution. To this solution was added Histone H1 (270 μg, 27 μL of a 10 mg/mL solution in water), and the sample was mixed.

Complex III. pDNA (45 μg, 22.5 μL of a 2 μg/μL solution in water) was added to 11.25 mL of injection solution. To this solution was added Histone H1 (50 μg, 5 μL of a 10 mg/mL solution in water), and the sample was mixed.

Complex IV. pDNA (45 μg, 22.5 μL of a 2 μg/μL solution in water) was added to 11.25 mL of injection solution. To this solution was added poly-L-lysine (144 μg, 14.4 μL of a 10 mg/mL solution in water, 30,000 MW), and the sample was mixed.

Complex V. pDNA (45 μg, 22.5 μL of a 2 μg/μL solution in water) was added to 11.25 mL of injection solution. To this solution was added linear polyethylenimine (67.5 μg, 6.7 μL of a 10 mg/mL solution in water, 20,000 MW, PolySciences Incorporated), and the sample was mixed.

Complex VI. pDNA (45 μg, 22.5 μL of a 2 μg/μL solution in water) was added to 11.25 mL of injection solution. To this solution was added branched polyethylenimine (67.5 μg, 6.7 μL of a 10 mg/mL solution in water, 25,000 MW, Aldrich Chemical Company), and the sample was mixed.

Complex VII. pDNA (45 μg, 22.5 μL of a 2 μg/μL solution in water) was added to 11.25 mL of injection solution. To this solution was added polycation L-cystine-1,4-bis(3-aminopropyl)piperazine copolymer (MC66; 210 μg, 21 μL of a 10 mg/mL solution in water), and the sample was mixed.

Synthesis of MC66 polymer: To a solution of N,N'-Bis(t-BOC)-L-cystine (85 mg, 0.15 mmol) in ethyl acetate (20 ml) was added N,N'-dicyclohexylcarbodiimide (108 mg, 0.5 mmol) and N-hyroxysuccinimide (60 mg, 0.5 mmol). After 2 h, the solution was filtered through a cotton plug and 1,4-bis(3-aminopropyl)piperazine (54 μL, 0.25 mmol) was added. The reaction was allowed to stir at room temperature for 16 h. The ethyl acetate was then removed by rotary evaporation and the resulting solid was dissolved in trifluoroacetic acid (9.5 ml), water (0.5 ml) and triisopropylsilane (0.5 ml). After 2 h, the trifluoroacetic acid was removed by rotary evaporation and the aqueous solution was dialyzed in a 15,000 MW cutoff tubing against water (2×2 L) for 24 h. The solution was then removed from dialysis tubing, filtered through 5 μM nylon syringe filter and then dried by lyophilization to yield 30 mg of polymer.

Injections and liver luciferase expression were determined as describe above. Luciferase expression in lung was determined similarly to liver expression. The results indicate that DNA complexes made with a variety of cationic polymers are able to be delivered to the liver and the encoded luciferase gene is expressed (Table 3). Delivery to and expression in the lung is also demonstrated (Table 4).

TABLE 3

Delivery to liver.

| Complex | Luciferase Activity (RLUs) | | | |
|---|---|---|---|---|
| | n1 | n2 | n3 | n4 |
| Complex I | 255,304,300 | 255,698,840 | 239,435,240 | 287,890,620 |
| Complex II | 141,548,520 | 220,373,240 | 120,569,430 | 76,730,000 |
| Complex III | 176,320,600 | 154,003,260 | 217,461,000 | 129,708,420 |
| Complex IV | 207,910,540 | 70,787,650 | 134,026,010 | 14,734,578 |
| Complex V | 215,938,580 | 160,859,660 | 47,298,530 | 221,795,440 |
| Complex VI | 188,847,920 | 257,840,960 | | |
| Complex VII | 29,321,620 | 12,751,690 | 20,745,930 | 32,821,050 |

TABLE 4

Delivery to lung.

| Complex | Luciferase Activity (RLUs) | | | |
|---|---|---|---|---|
| | n1 | n2 | n3 | n4 |
| Complex I | 407,752 | 986,658 | 530,070 | 501,991 |
| Complex II | 277,897 | 161,810 | 101,566 | 115,227 |
| Complex III | 1,387,668 | 406,831 | 276,389 | 166,063 |
| Complex IV | 159,589 | 72,023 | 119,674 | 92,204 |
| Complex V | 1,092,245 | 588,622 | 482,355 | 1,040,256 |
| Complex VI | 1,779,630 | 288,898 | | |
| Complex VII | 179,003 | 259,388 | 78,325 | 88,841 |

D. Comparison of Ringer's and low-salt Glucose Injection Solutions for Complex Delivery by Mouse Tail Vein Injections. Two solutions were used in this experiment. Solution A was prepared consisting of 290 mM glucose, 5 mM Hepes, adjusted to pH 7.5. Solution B was Ringer's.

Complexes were prepared as follows:

Complex I. pDNA (45 µg, 22.5 µL of a 2 µg/µL solution in water) was added to 11.25 mL of Solution A.

Complex II. pDNA (45 µg, 22.5 µL of a 2 µg/µL solution in water) was added to 11.25 mL of Solution A. To this solution was added Histone H1 (270 µg, 27 µL of a 10 mg/mL solution in water), and the sample was mixed.

Complex III. pDNA (45 µg, 22.5 µL of a 2 µg/µL solution in water) was added to 11.25 mL of Solution A. To this solution was added Histone H1 (50 µg, 5 ptL of a 10 mg/mL solution in water), and the sample was mixed.

Complex IV. pDNA (45 µg, 22.5 µL of a 2 µg/µL solution in water) was added to 11.25 mL of Solution A. To this solution was added Histone H1 (36 ptg, 3.6 µL of a 10 mg/mL solution in water), and the sample was mixed.

Complex V. pDNA (45 µg, 22.5 µL of a 2 µg/µL solution in water) was added to 11.25 mL of Solution B.

Complex VI. pDNA (45 µg, 22.5 µL of a 2 µg/µL solution in water) was added to 11.25 mL of Solution B. To this solution was added Histone H1 (270 µg, 27 µL of a 10 mg/mL solution in water), and the sample was mixed.

Complex VII. pDNA (45 µg, 22.5 µL of a 2 µg/µL solution in water) was added to 11.25 mL of Solution B. To this solution was added Histone H1 (50 µg, 5 µL of a 10 mg/mL solution in water), and the sample was mixed.

Complex VIII. pDNA (45 µg, 22.5 µL of a 2 µg/µL solution in water) was added to 11.25 mL of Solution B. To this solution was added Histone H I(36 µg, 3.6 ilL of a 10 mg/mL solution in water), and the sample was mixed.

Complex IX. The lipid DOTAP-Chloride (225 µg, 9 µL of a 25 mg/mL solution in chloroform, Avanti Polar Lipids) and the lipid DOPE (225 µg, 9 µL of a 25 mg/mL solution in chloroform, Avanti Polar Lipids) were added to 500 µL of chloroform. The solution was concentrated under a stream of $N_2$ into a film, and dried for 16 hrs under vacuum. The film was hydrated with 11.25 mL of Solution A for 5 min, and sonicated for 20 min. pDNA (45 µg, 22.5 µL of a 2 µg/µL solution in water) was added to the mixture, and the sample was mixed for 5 min on a vortexer.

Complex X. The lipid DOTAP-Chloride (225 µg, 9 µL of a 25 mg/mL solution in chloroform, Avanti Polar Lipids) and the lipid DOPE (225 µg, 9 µL of a 25 mg/mL solution in chloroform, Avanti Polar Lipids) were added to 500 µL of chloroform. The solution was concentrated under a stream of $N_2$ into a film, and dried for 16 hrs under vacuum. The film was hydrated with 11.25 mL of Solution B for 5 min, and sonicated for 20 min. pDNA (45 µg, 22.5 µL of a 2 µg/µL solution in water) was added to the mixture, and the sample was mixed for 5 min on a vortexer.

Injections and luciferase expression were determined as describe above. The results show that cationic polymer/DNA complexes were more efficiently delivered to liver cells when the complexes are injected in Solution A, relative to Solution B. Conversely, anionic polymer/pDNA complexes were more efficiently delivered to liver cells when the complexes are injected in Solution B, relative to Solution A. Cationic liposomes with pDNA were more efficiently delivered to liver cells when injected with Solution A relative to Solution B (Table 5).

TABLE 5

Nucleic acid delivery to liver.

| | Luciferase Activity (RLUs) | | | |
|---|---|---|---|---|
| Complex | n1 | n2 | n3 | n4 |
| Complex I | 250,254,200 | 1,911,573,000 | 1,315,766,100 | |
| Complex II | 1,294,448,100 | 1,304,320,300 | 15,330,902 | 1,713,994,600 |
| Complex III | 1,040,996,600 | 221,108,100 | 1,399,596,800 | |
| Complex IV | 612,352,500 | 505,715,400 | 325,778,000 | 667,218,300 |
| Complex V | 2,043,992,000 | 1,073,708,500 | 349,158,900 | 776,722,000 |
| Complex VI | 95,870,500 | 10,643,600 | 578,100 | 1,930,400 |
| Complex VII | 49,343,900 | 38,798,800 | 29,196,500 | 16,183,100 |
| Complex VIII | 1,992,733,600 | 585,884,300 | 1,339,022,600 | 1,395,211,400 |
| Complex IX | 408,356,100 | 1,708,282,800 | 1,396,587,200 | 1,853,258,400 |
| Complex X | 7,042,300 | 1,085,700 | 632,200 | 2,852,900 |

The results show that cationic polymer/DNA complexes were more efficiently delivered to lung cells when the complexes are injected in Solution A, relative to Solution B. Conversely, anionic polymer/pDNA complexes were more efficiently delivered to lung cells when the complexes are injected in Solution B, relative to Solution A. Cationic liposomes with pDNA were more efficiently delivered to lung cells when injected with Solution A relative to Solution B (Table 6).

TABLE 6

Nucleic acid delivery to lung.

| | Luciferase Activity (RLUs) | | | |
|---|---|---|---|---|
| Complex | n1 | n2 | n3 | n4 |
| Complex I | 377,114 | 897,605 | 427,658 | |
| Complex II | 2,565,810 | 607,075 | 1,722,082 | 528,407 |
| Complex III | 200,972 | 194,889 | 627,672 | |
| Complex IV | 107,896 | 121,428 | 206,011 | 128,814 |
| Complex V | 1,371,267 | 501,363 | 414,898 | 584,481 |
| Complex VI | 16,255 | 13,738 | 4,507 | 1,656 |
| Complex VII | 21,337 | 27,919 | 11,106 | 9,861 |
| Complex VIII | 137,644 | 100,675 | 473,943 | 623,084 |
| Complex IX | 163,558 | 612,049 | 408,195 | 1,071,426 |
| Complex X | 177,901 | 32,619 | 20,326 | 3,120 |

E. Mouse Tail Vein Injections of pDNA and Polycation/pDNA Complexes in Different Solutions. Several solutions were prepared for use as injection solutions. Solution A was prepared consisting of 290 mM glucose, 5 mM Hepes, adjusted to pH 7.5. Solution B was Ringer's. Solution C was 2.6 % Glycerol (Sigma Chemical Company). Solution D was 2.19% Glycine (Aldrich Chemical Company).

Complexes were prepared as follows:
Complex I. pDNA (45 µg, 22.5 µL of a 2 µg/µL solution in water) was added to 11.25 mL of Solution B.
Complex II. pDNA (45 µg, 22.5 µL of a 2 µg/µL solution in water) was added to 11.25 mL of Solution A.
Complex III. pDNA (45 µg, 22.5 gL of a 2 µg/µL solution in water) was added to 11.25 mL of Solution C.
Complex IV. pDNA (45 µg, 22.5 µL of a 2 µg/µL solution in water) was added to 11.25 mL of Solution D.
Complex V. pDNA (45 µg, 22.5 µL of a 2 µg/µL solution in water) was added to 11.25 mL of Solution A. To this solution was added Histone H1 (270 µg, 27 µL of a 10 mg/mL solution in water), and the sample was mixed.
Complex VI. pDNA (45 µg, 22.5 µL of a 2 µg/µL solution in water) was added to 11.25 mL of Solution C. To this solution was added Histone H1 (270 µg, 27 µL of a 10 mg/mL solution in water), and the sample was mixed.
Complex VII. pDNA (45 µg, 22.5 µL of a 2 µg/µL solution in water) was added to 11.25 mL of Solution D. To this solution was added Histone H1 (270 ug, 27 IL of a 10 mg/mL solution in water), and the sample was mixed.

Injections and luciferase expression were determined as describe above. The results indicate that injection in solutions A, B, C, and D results in effective delivery of nucleic acid to liver cells. The results also indicate that pDNA/polycation complexes are able to be delivered to liver and liver cells and expressed using a variety of low-salt solutions (Tables 7 and 8).

Complex I. pDNA (50 µg, 255 µL of a 2 µg/µL solution in water) was added to 12.5 mL of Solution A. To this solution was added Histone H1 (300 µg, 30 µL of a 10 mg/mL solution in water), and the sample was mixed.
Complex II. pDNA (50 µg, 255 µL of a 2 µg/µL solution in water) was added to 12.5 mL of Solution B. To this solution was added Histone H1 (300 µg, 30 µL of a 10 mg/mL solution in water), and the sample was mixed.

Injections and liver luciferase expression were determined as describe above. Luciferase expression in spleen, heart, and kidney was determined similarly to liver expression. Results indicate that tail vein injection of polycation/DNA complexes in 290 mM glucose/5 mM Hepes or 8.79% glucose enables delivery of expressible DNA to a variety of tissues—including liver, spleen, lung, heart and kidney (Table 9a-9e).

TABLE 7

Liver

Luciferase Activity (RLUs)

| Complex | n1 | n2 | n3 | n4 |
|---|---|---|---|---|
| Complex I | 675,151,700 | 1,200,913,300 | 1,187,502,400 | 590,617,700 |
| Complex II | 610,335,900 | 822,375,900 | 636,497,700 | 1,247,489,200 |
| Complex III | 93,460,300 | 30,277,700 | 207,443,600 | |
| Complex IV | 1,327,374,100 | 1,391,409,600 | 464,197,400 | 720,158,600 |
| Complex V | 327,850,100 | 319,533,200 | 486,881,200 | 253,500,300 |
| Complex VI | 183,430,200 | 96,904,200 | | |
| Complex VII | 266,323,500 | 722,151,300 | 339,682,400 | 277,427,200 |

TABLE 8

Lung

Luciferase Activity (RLUs)

| Complex | n1 | n2 | n3 | n4 |
|---|---|---|---|---|
| Complex I | 858,267 | 268,512 | 215,034 | 164,993 |
| Complex II | 1,071,714 | 978,088 | 498,480 | 798,461 |
| Complex III | 339,159 | 157,493 | 258,775 | |
| Complex IV | 3,608,237 | 429,987 | 357,840 | 179,288 |
| Complex V | 769,816 | 472,389 | 198,794 | 162,666 |
| Complex VI | 246,191 | 219,022 | | |
| Complex VII | 683,793 | 289,933 | 352,693 | 207,757 |

F. Delivery of Polycation/pDNA Complexes via Mouse Tail Vein Injections in isotonic and hypertonic injection solutions. Two solutions were prepared for use as injection solutions. Solution A was prepared consisting of 290 mM glucose, 5 mM Hepes, adjusted to pH 7.5. Solution B was hypertonic and prepared consisting of 8.79% glucose in water. Complexes were prepared as follows:

TABLE 9a

Liver

Luciferase Activity (RLUs)

| Complex | n1 | n2 | n3 | n4 |
|---|---|---|---|---|
| Complex I | 111,543,340 | 118,545,220 | 34,611,130 | 196,298,240 |
| Complex II | 101,105,730 | 56,172,710 | 123,733,880 | |

TABLE 9b

Spleen

Luciferase Activity (RLUs)

| Complex | n1 | n2 | n3 | n4 |
|---|---|---|---|---|
| Complex I | 1,129,731 | 273,898 | 18,190 | 48,308 |
| Complex II | 164,826 | 42,731 | 133,207 | |

TABLE 9c

Lung

Luciferase Activity (RLUs)

| Complex | n1 | n2 | n3 | n4 |
|---|---|---|---|---|
| Complex I | 780,416 | 102,143 | 167,605 | 55,330 |
| Complex II | 156,814 | 57,281 | 113,495 | |

TABLE 9d

| | Heart | | | |
|---|---|---|---|---|
| | Luciferase Activity (RLUs) | | | |
| Complex | n1 | n2 | n3 | n4 |
| Complex I | 136,593 | 27,966 | 19,797 | 13,209 |
| Complex II | 46,367 | 12,281 | 40,528 | |

TABLE 9e

| | Kidney | | | |
|---|---|---|---|---|
| | Luciferase Activity (RLUs) | | | |
| Complex | n1 | n2 | n3 | n4 |
| Complex I | 207,078 | 47,894 | 57,887 | 66,362 |
| Complex II | 94,278 | 20,112 | 82,799 | |

G. Mouse Tail Vein Injections of pDNA in Ringer's and Mannitol Injection Solutions. Two solutions were prepared for use as injection solutions. Solution A was Ringer's. Solution B was 5.07% mannitol (Sigma Chemical Company).

Complexes were prepared as follows:

Complex I. pDNA (50 μg, 25 μL of a 2 μg/μL solution in water) was added to 12.5 mL of Solution A.

Complex II. pDNA (50 μg, 255 μL of a 2 μg/μL solution in water) was added to 12.5 mL of Solution B.

Injections and luciferase expression were determined as describe above. The results indicate that the mannitol injection solution is more effective for the delivery of pDNA to the liver than Ringer's injection solution (Table 10).

TABLE 10

| | Nucleic acid delivery to liver cells in vivo. | | | |
|---|---|---|---|---|
| | Luciferase Activity (RLUs) | | | |
| Complex | n1 | n2 | n3 | n4 |
| Complex I | 224,690,400 | 249,641,200 | 179,375,300 | 133,608,000 |
| Complex II | 442,422,000 | 573,437,100 | 505,887,400 | 587,261,400 |

H. Effect of the Speed of Injection for Mouse Tail Vein Injections. Two injection solutions were used in this experiment. Solution A was prepared consisting of 290 mM glucose, 5 mM Hepes, adjusted to pH 7.5. Solution B was Ringer's.

Complexes were prepared as follows:

Complex I. pDNA (45 μg, 22.5 μL of a 2 μg/μL solution in water) was added to 11.25 mL of Solution B.

Complex II. pDNA (45 μg, 22.5 μL of a 2 μg/μL solution in water) was added to 11.25 mL of Solution A Complex III pDNA (45 μg, 22.5 μL of a 2 μg/μL solution in water) was added to 11.25 mL of Solution A. To this solution was added Histone Hl (270 μg, 27 μL of a 10 mg/mL solution in water), and the sample was mixed.

Injections and luciferase expression were determined as described above except that injection was done by a Harvard Apparatus PHD 2000 programmable pump with varying solution delivery times. For injections in under 5 sec delivery time, injections were done by hand. The results indicate increased delivery of the complexes to liver and lung as the injection time is decreased. Expression was slightly higher for the two-minute injection than for the one-minute injection (Table 11).

TABLE 11

| | | Liver | | | |
|---|---|---|---|---|---|
| | Injection | Luciferase Activity (RLUs) | | | |
| Complex | Time | n1 | n2 | n3 | n4 |
| Complex I | <5 sec | 785,052,500 | 950,625,100 | 708,296,900 | 670,048,200 |
| Complex II | <5 sec | 1,050,727,300 | 2,669,898,600 | 1,253,517,100 | 332,099,500 |
| Complex III | <5 sec | 840,101,200 | 394,642,700 | 678,283,200 | |
| | 5 sec | 330,553,100 | 212,748,600 | 180,455,300 | |
| | 10 sec | 99,517,000 | 240,308,900 | 212,794,700 | |
| | 15 sec | 65,041,000 | 48,198,200 | 92,092,600 | 14,146,900 |
| | 30 sec | 6,310,700 | 152,300 | 3,388,400 | 711,700 |
| | 60 sec | 455,200 | 127,500 | 151,300 | 120,100 |
| | 120 sec | 1,499,500 | 1,426,500 | 810,200 | 589,200 |

TABLE 11b

| | | Lung | | | |
|---|---|---|---|---|---|
| | Injection | Luciferase Activity (RLUs) | | | |
| Complex | Time | n1 | n2 | n3 | n4 |
| Complex I | <5 sec | 1,467,887 | 1,169,557 | 983,087 | 282,830 |
| Complex II | <5 sec | 2,000,448 | 1,006,577 | 709,969 | 305,448 |
| Complex III | <5 sec | 1,424,305 | 328,739 | 709,669 | |
| | 5 sec | 279,350 | 115,252 | 70,416 | |
| | 10 sec | 271,528 | 92,553 | 45,079 | |
| | 15 sec | 91,152 | 119,980 | 180,660 | 94,151 |
| | 30 sec | 32,971 | 39,468 | 14,183 | 8,402 |
| | 60 sec | 14,579 | 8,963 | 7,887 | 2,583 |
| | 120 sec | 88,508 | 132,603 | 63,122 | 45,572 |

I. Delivery of pDNA and pDNA/Detergent complexes via Injection in Glucose Solution into Tail Vein. An injection solution was prepared comprising 290 mM glucose (Sigma Chemical Company), 5 mM Hepes (Sigma Chemical Company), adjusted to pH 7.5.

pDNA—detergent complexes are prepared by diluting the pDNA to a concentration of approximately 1 mg/mL in water, and adding 2 molar equivalents of the detergent as a solution in water. The complex is then mixed and lyophilized until dry. The resulting solid is resuspended in an organic solvent— such as ethanol, chloroform, or DMF. MC 909 is the amide derived from N-acetyl, S-oleoyl cysteine and N,N-diaminopropylamine.

Several complexes were prepared as follows:

Complex I. pDNA (30 µg, 15 µL of a 2 µg/µL solution in water) was added to 6.9 mL of the injection solution, and the injection was mixed.

Complex II. pDNA—dodecylamine hydrochloride (30 µg, 15 µL of a 2 µg/µL solution in DMF) was added to the injection solution, and the solution was mixed.

Complex III. pDNA—MC909 (30 µg, 15 µL of a 2 µg/µL solution in DMF) was added to the injection solution, and the solution was mixed.

Injections and luciferase expression were determined as describe above. The results indicate that the mannitol injection solution is more effective for the delivery of pDNA to the liver than Ringer's injection solution (Table 12). The results indicate that the described process is effective for delivering functional DNA/detergent complexes to the liver in vivo.

TABLE 12

Results from liver assay (RLU), n = 2.

| Complex Number | n1 | n2 |
|---|---|---|
| Complex I | 1,226,128,400 | 620,800,400 |
| Complex II | 897,920,800 | 415,377,300 |
| Complex III | 133,628,300 | 137,486,200 |

2. Delivery of Plasmid DNA and DNA Complexes to Liver in Rat via Portal Vein Injections:

Two solutions were prepared for use as injection solutions. Solution A was Ringer's. Solution B consisted of 290 mM glucose, 5 mM Hepes, adjusted to pH 7.5.

Complexes were prepared as follows:

Complex I. pDNA (220 µg, 110 µL of a 2 µg/µL solution in water) was added to 24.2 mL of solution A.

Complex II. pDNA (220 µg, 110 µL of a 2 µg/µL solution in water) was added to 24.2 mL of solution B.

Complex III. pDNA (220 µg, 110 µL of a 2 µg/µL solution in water) was added to 24.2 mL of solution A. To this solution was added Histone H1 (1320 µg, 132 µL of a 10 mg/mL solution in water), and the sample was mixed.

Complex IV. pDNA (220 µg, 110 µL of a 2 µg/µL solution in water) was added to 24.2 mL of solution B. To this solution was added Histone H1 (1320 µg, 132 µL of a 10 mg/mL solution in water), and the sample was mixed.

Complex V. pDNA (220 µg, 110 µL of a 2 µg/µL solution in water) was added to 24.2 mL of solution A. To this solution was added poly-L-lysine (704 µg, 70.4 µL of a 10 mg/mL solution in water, 30,000 MW), and the sample was mixed.

Complex VI. pDNA (220 µg, 110 µL of a 2 µg/µL solution in water) was added to 24.2 mL of solution B. To this solution was added poly-L-lysine (704 µg, 70.4 µL of a 10 mg/mL solution in water, 30,000 MW), and the sample was mixed.

Livers were exposed through a ventral midline incision, and the complexes, in 10 ml injection solution, were manually injected over approximately 20-30 sec into the portal vein using a 30-gauge, ½-inch needle and 1-ml syringe. A 3 cm microvascular clamp (Edward Weck, Inc., Research Triangle Park, N.C.) was applied during the injection at the junction of the hepatic vein and caudal vena cava. Anesthesia was obtained from intramuscular injection of 70 mg/kg ketamine-HCl (Parke-Davis, Morris Plains, N.J.) in 1 ml of normal saline and from inhalation of methoxyflurane (Pitman-Moore, Mudelein, IL. USA) as needed. One day after injection, the animals were sacrificed, and luciferase expression was assayed from both liver and lung tissue (Table 13 and 14).

TABLE 13

Liver

| | Luciferase Activity (RLUs) | |
|---|---|---|
| Complex | n1 | n2 |
| Complex I | 2,335,040 | 2,546,944 |
| Complex II | 4,484,908 | 15,997,978 |
| Complex III | 7,085 | 3,522 |
| Complex IV | 3,659,565 | 14,016,174 |
| Complex V | 737 | 2,618 |
| Complex VI | 320,306 | 1,256,867 |

The results indicate that pDNA delivery to liver tissue is better when injected in solution B as compared to solution A. Additionally, the results indicate that polycation/pDNA complexes can be delivered to liver cells, and the pDNA is expressible, when the complexes are injected in solution B.

TABLE 14

Lung

| | Luciferase Activity (RLUs) | |
|---|---|---|
| Complex | n1 | n2 |
| Complex I | 7,304 | 2,411 |
| Complex II | 3,618 | 11,885 |
| Complex III | 1,227 | 657 |
| Complex IV | 4,145 | 589 |
| Complex V | 289 | 347 |
| Complex VI | 547 | 1,478 |

The results indicate that the pDNA can be delivered to lung cells, and the pDNA is expressible, with both solution A and solution B. The results also indicate that polycation/pDNA complexes are more effectively delivered to the lung cells with solution B.

These experiments demonstrate effective delivery of DNA to hepatic cells via injection into an afferent vessel of the liver. In similar experiments, the hepatic vein was occluded during the procedure resulting in up to three-fold higher expression. Sectioning of the liver showed even distribution of delivery throughout the liver, with similar luciferase expression in the right, left, and medial lobes of the liver. Similar results were also observed when DNA-containing solution were injected into the hepatic vein, an efferent vessel of the liver. For delivery via hepatic vein, the injections were directed into the inferior cava which was clamped in two locations; proximal and distal (i.e. downstream and upstream) to the entry of the hepatic vein into the inferior vena cava. Specifically, the downstream inferior vena cava clamp was placed between the diaphragm and the entry point of the hepatic vein. The upstream inferior vena cava clamp was placed just downstream of the entry point of the renal veins. Therefore, the 1 ml of the injection fluid entered the hepatic vein and the liver. Since the veins of other organs such as the renal veins enter the inferior vena cava at this location, not all of the 1 ml of injection fluid goes into the liver. In some of the animals that received retrograde injections in the inferior vena cava, the hepatic artery, mesenteric artery, and portal vein were clamped (occluded) for approximately five minutes immediately before and then after the injections. Specifically, the order of placing the clamps were as follows: first on hepatic artery, then portal vein, then downstream vena cava, and then upstream vena cava. It took about three minutes to place all these clamps and then the injections were done. The clamps were left in place for an additional two minutes from the time that the last clamp (upstream vena cava clamp) was placed.

3. Delivery to Rat Skeletal Muscle Cells In Vivo Using Intra-iliac Injection.

A. Delivery of DNA and polycation/DNA to skeletal muscle via Iliac injection in Rat: Solution A was prepared consisting of 290 mM glucose, 5 mM Hepes, adjusted to pH 7.5.

Complexes were prepared as follows:

Complex I. pDNA (250 µg, 125 µL of a 2 µg/µL solution in water) was added to 40 mL of Solution A.

Complex II. pDNA (250 µg, 125 µL of a 2 µg/µL solution in water) was added to 40 mL of Solution A. To this solution was added Histone H1 (1500 µg, 150 µL of a 10 mg/mL solution in water), and the sample was mixed.

Solutions were injected into iliac artery of rats using a Harvard Apparatus PHD 2000 programmable syringe pump. Specifically, animals were anesthetized and the surgical field shaved and prepped with an antiseptic. The animals were placed on a heating pad to prevent loss of body heat during the surgical procedure. A midline abdominal incision was be made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins to block both outflow and inflow of the blood to the leg. An efflux enhancer solution (e.g., 0.5 mg papaverine in 3 ml saline) was pre-injected into the external iliac artery though a 25 g needle. Ten min later, 12 mL injection solution containing the indicated complexes was injected in approximately 10 seconds. The microvessel clips were removed 2 minutes after the injection and bleeding was controlled with pressure and gel foam. The abdominal muscles and skin were closed with 4-0 dexon suture. Seven days after injection, the animals were sacrificed, and a luciferase assays were conducted on leg muscles. Luciferase expression was determined as previously reported [Wolff et al. 1990] The results indicate that pDNA is delivered and expressed in muscle following iliac injection in solution A. Polycation/pDNA complexes were delivered less efficiently than pDNA alone (Table 15).

TABLE 15A

| Complex | Muscle Group | Tissue Volume | Luciferase Activity (RLUs) | |
| --- | --- | --- | --- | --- |
| | | | n1 | n2 |
| Complex I | Quadriceps | 15 mL | 425,647 | 131,010 |
| | Biceps | 15 mL | 157,149 | 88,373 |
| | Hamstring | 15 mL | 351,731 | 83,312 |
| | Gastrocnemius | 15 mL | 376,354 | 245,395 |
| | Lower shin | 5 mL | 124,372 | 72,920 |
| | Foot | 2 mL | 1,159 | 634 |
| Complex II | Quadriceps | 15 mL | 2,541 | 2,364 |
| | Biceps | 15 mL | 1,831 | 1,623 |
| | Hamstring | 15 mL | 10,495 | 2,190 |
| | Gastrocnemius | 15 mL | 6,624 | 265 |
| | Lower shin | 5 mL | 449 | 7,163 |
| | Foot | 2 mL | 451 | 147 |

250 µg pCI-Luc plasmid DNA in 10 ml Ringer's injection solution was injected into iliac artery of rats using a Harvard Apparatus PHD 2000 programmable syringe pump as described above, except that varying injection rates were used. Results show that efficiency of delivery is affected by the rate of solution injection.

TABLE 15B

Luciferase expression (ng Luciferase) after delivery of plasmid DNA to muscle via iliac administration route.

| | Injection Rate | | | |
| --- | --- | --- | --- | --- |
| muscle | 0.83 ml/sec n = 2 | 0.56 ml/sec n = 4 | 0.42 ml/sec n = 3 | 0.33 ml/sec n = 3 |
| quad | 1109 ± 1183 | 384 ± 386 | 733 ± 154 | 221 ± 246 |
| biceps | 1476 ± 1138 | 276 ± 185 | 604 ± 122 | 83 ± 37 |
| hamstring | 2413 ± 1045 | 2071 ± 942 | 1635 ± 643 | 706 ± 384 |
| gastrocnemius | 1852 ± 1316 | 2274 ± 673 | 2088 ± 329 | 1078 ± 372 |
| shin | 774 ± 610 | 367 ± 361 | 289 ± 274 | 189 ± 63 |
| foot | 6 ± 5.5 | 8.9 ± 10.7 | 4.3 ± 2.2 | 0.9 ± 0.2 |
| total | 7397 ± 4456 | 7389 ± 2062 | 6664 ± 1001 | 3338 ± 1762 |

B. Rat Iliac Injections of pDNA and pDNA/Polycation/Polyanion Complexes in Different Solutions: Solution A was normal saline. Solution B was prepared consisting of 290 mM glucose (Sigma Chemical Company), 5 mM Hepes (Sigma Chemical Company), adjusted to pH7.5.

Several complexes were prepared as follows:

Complex I. pDNA (250 µg, 125 µL of a 2 µg/µL solution in water) was added to 25 mL of Solution A.

Complex II. pDNA (250 µg, 125 µL of a 2 µg/µL solution in water) was added to 25 mL of Solution B.

Complex III. pDNA (250 µg, 125 µL of a 2 µg/µL solution in water) was added to 25 mL of Solution A. To this solution was added Poly-L-Lysine Hydrobromide (473 µg, 47.3 RL of a 10 mg/mL solution in water, Sigma Chemical Company), and the sample was mixed. To this solution was added Succinylated Poly-L-Lysine (1721 µg, 34.4 µL of a 50 mg/mL solution in water, Sigma Chemical Company), and the sample was mixed.

Complex IV. pDNA (250 µg, 125 µL of a 2 µg/µL solution in water) was added to 25 mL of Solution B. To this solution was added Poly-L-Lysine Hydrobromide (473 µg, 47.3 µL of a 10 mg/mL solution in water, Sigma Chemical Company), and the sample was mixed. To this solution was added Succinylated Poly-L-Lysine (1721 µg, 34.4 µL of a 50 mg/mL solution in water, Sigma Chemical Company), and the sample was mixed.

Rat iliac injections of 10 mL of solution (n=2) were conducted as previously described. Seven days after injection, the animal was sacrificed, and a luciferase assay was conducted on the leg muscles.

TABLE 16

Results of iliac injection.

| Complex Number | Muscle Group | Tissue Volume | n1 | n2 |
| --- | --- | --- | --- | --- |
| Complex I | Quadriceps | 15 mL | 12,514,072 | 16,227,067 |
| | Bisceps | 15 mL | 9,586,089 | 19,093,910 |
| | Hamstring | 15 mL | 16,854,596 | 17,801,864 |
| | Gastrocnemius | 15 mL | 21,112,660 | 23,629,012 |
| | Lower shin | 5 mL | 6,996,074 | 4,859,628 |
| | Foot | 2 mL | 664,633 | 492,209 |
| Complex II | Quadriceps | 15 mL | 9,152,141 | 7,472,630 |
| | Bisceps | 15 mL | 6,685,673 | 10,358,753 |
| | Hamstring | 15 mL | 13,285,607 | 10,120,048 |
| | Gastrocnemius | 15 mL | 15,893,838 | 15,643,649 |
| | Lower shin | 5 mL | 5,244,860 | 4,040,980 |
| | Foot | 2 mL | 1,053,676 | 1,805,209 |

TABLE 16-continued

Results of iliac injection.

| Complex Number | Muscle Group | Tissue Volume | n1 | n2 |
|---|---|---|---|---|
| Complex III | Quadriceps | 15 mL | 13,681 | 4,519 |
| | Bisceps | 15 mL | 5,910 | 2,344 |
| | Hamstring | 15 mL | 7,471 | 2,593 |
| | Gastrocmemius | 15 mL | 3,402 | 3,106 |
| | Lower shin | 5 mL | 3,605 | 3,602 |
| | Foot | 2 mL | 320 | 4,144 |
| Complex IV | Quadriceps | 15 mL | 25,892 | 31,365 |
| | Bisceps | 15 mL | 8,404 | 10,196 |
| | Hamstring | 15 mL | 14,034 | 15,501 |
| | Gastrocmemius | 15 mL | 9,545 | 22,867 |
| | Lower shin | 5 mL | 24,146 | 10,229 |
| | Foot | 2 mL | 16,121 | 19,215 |

The results indicate that plasmid is delivered and expressed in muscle following iliac injection in solution A and solution B. pDNA/Polycation/Polyanion complexes were delivered more efficiently with solution B than with solution A.

C. Delivery of negatively charged PEI/DNA and histone H1/DNA complexes to skeletal muscles in rat via a single injection into the iliac artery: PEI/DNA and histone H1/DNA particles were injected into rat leg muscle by a single intra-arterial injection into the external iliac. Female Harlan Sprague Dawley rats, approximately 150 g, each received complexes containing 100 μg plasmid DNA encoding the luciferase gene under control of the CMV enhancer/promoter (pCI-Luc) [Zhang et al. 1997]. Rat iliac injections of 10 mL of solution (n=2) were conducted as previously described. Results of the rat injections are provided in relative light units (RLUs) and micrograms (μg) of luciferase produced. To determine RLUs, 10 μl of cell lysate were assayed luminometer and total muscle RLUs were determined by multiplying by the appropriate dilution factor. To determine the total amount of luciferase expressed per muscle we used a conversion equation that was determined in an earlier study [Zhang et al. 1997] [pg luciferase=RLUs$\times 5.1 \times 10^{-5}$].

TABLE 17

Luciferase expression in multiple muscles of the leg following injection of negatively charged DNA/PEI or DNA/Histone HI particles.

| Muscle Group | Total RLUs | Total Luciferase |
|---|---|---|
| DNA/PEI particles (1:0.5 charge ratio) | | |
| muscle group 1 (upper leg anterior) | $3.50 \times 10^9$ | 0.180 μg |
| muscle group 2 (upper leg posterior) | $3.96 \times 10^9$ | 0.202 μg |
| muscle group 3 (upper leg medial) | $7.20 \times 10^9$ | 0.368 μg |
| muscle group 4 (lower leg posterior) | $9.90 \times 10^9$ | 0.505 μg |
| muscle group 5 (lower leg anterior) | $9.47 \times 10^8$ | 0.048 μg |
| muscle group 6 (foot) | $6.72 \times 10^6$ | 0.0003 μg |
| DNA/histone H1 particles (1:0.5 charge ratio) | | |
| muscle group 1 (upper leg anterior) | $3.12 \times 10^9$ | 0.180 μg |
| muscle group 2 (upper leg posterior) | $9.13 \times 10^9$ | 0.202 μg |
| muscle group 3 (upper leg medial) | $1.23 \times 10^{10}$ | 0.368 μg |
| muscle group 4 (lower leg posterior) | $5.73 \times 10^9$ | 0.505 μg |
| muscle group 5 (lower leg anterior) | $4.81 \times 10^8$ | 0.048 μg |
| muscle group 6 (foot) | $6.49 \times 10^6$ | 0.0003 μg |

Results indicated delivery of the negatively charged complexes containing luciferase-expressing plasmid to muscles throughout the leg via injection into a afferent artery.

4. Delivery of Polynucleotides to Limb Skeletal Muscle in Mdx Mice: ICR or mdx mice, ~30 gram, were anesthetized by intramuscular injection of ketamine(80-100 mg/kg) and xylazine (2 mg/kg). Metofane was added through inhalation if necessary during the procedure. A median incision was made from the upper third of abdomen to the caudal edge of the abdominal and the right caudal part of abdominal cavity was exposed using retractors. The tissue in front of the right external iliac artery was cleaned by forceps and a cotton tipped applicator. The arteries and veins to be clamped were separated from surrounding tissue and the caudal epigratric artery and vein, internal iliac arteries and vein, gluteal artery and vein, the vessels of deferent duct and external iliac artery and vein were clamped. A 0.6 ml of papaverine solution (containing 0.1 mg of papaverine) was injected into external iliac artery distal to the clamp. 2.5-3 ml of DNA solution containing 100 1g plasmid DNA was injected into the external iliac artery distal to the clamp with pressure 5 minutes post papaverine injection. A piece of gelfoam was put on the injection site before withdrawal of the needle and pressure was kept on the gelfoam to prevent bleeding. The clamps are taken off 2 minutes after injection and the abdominal cavity was closed by suturing.

Muscle samples were taken 7-10 days after injection and 6 μm thickness cryostat sections were made. Endogenous peroxidase activities were blocked by incubating the sections in 0.3% hydrogen peroxide in PBS for 5-10 min after the sections were mounted on slides and dried. The sections were rinsed twice with PBS (2 min$\times$2) followed by Avidin/Biotin blocking by using Vector Avidin/Biotin Blocking Kit (Cat. No. SP-2001). The following steps were done according to the procedure of Vector M.O.M Immunodetection Kit (Cat. No. PK-2200). The immunofluorescent staining for human dystrophin in mouse muscle was done following the procedure of Vector M.O.M Immunodetection Kit (Cat. No. FMK-2201). For luciferase assays, 5 groups of muscle were taken from the whole injected leg according to their distribution, the anterior, posterior, medial, anterior of low leg and posterior of low leg. 2 ml of cold lysis buffer was added to each group of muscle followed by homogenization. Luciferase activity was measured by luminometer and the light units were converted to luciferase protein by using the converting rate of pg=light units$\times$solution volume/20$\times$2.05/100000

Figure 1:
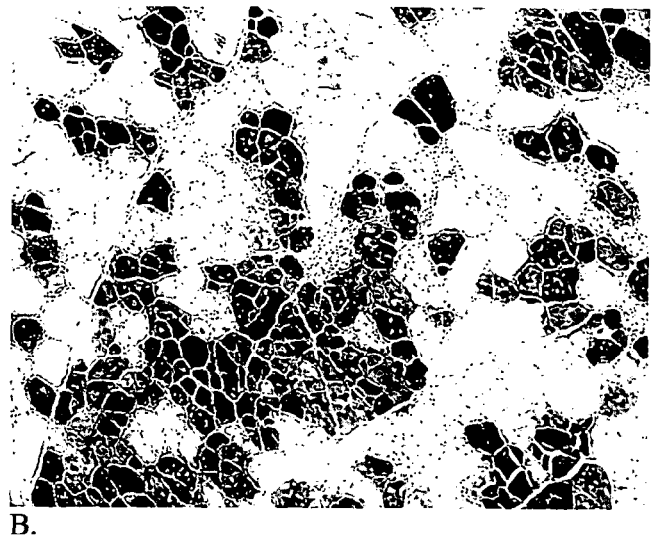
FIG. 1. LacZ or dystrophin expression in mouse skeletal muscle seven days following intra-arterial injections of 100 µg pCI-LacZ (A) or pMI-DYS (B and C) in dystrophic mdx mouse (A and B) or normal ICR mouse (C)
Figure 1:
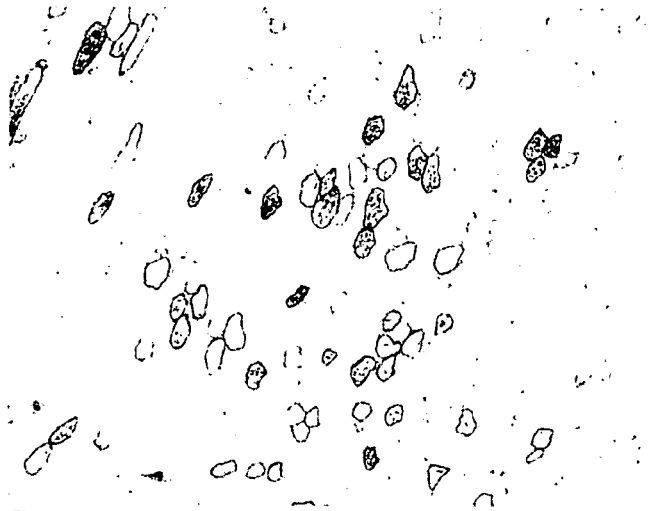
Figure 1:
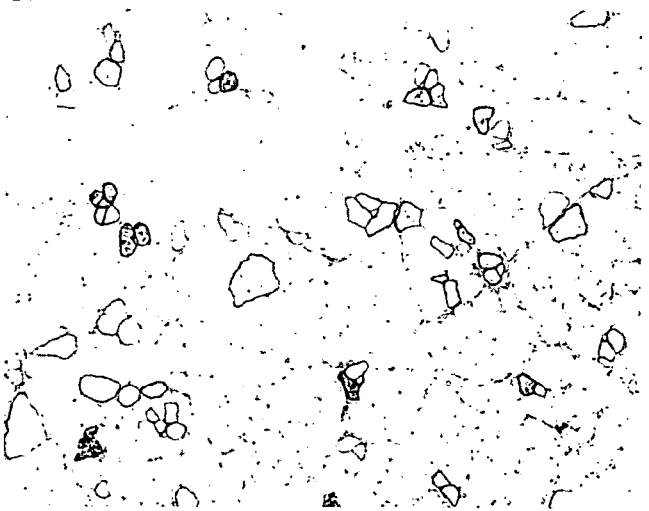

Results are shown in Table 18 and FIG. 1. FIG. 1A shows β-galactosidase expression in mdx dystrophic mouse. FIGS. 1B and C show human dystrophin expression in leg skeletal muscle in mdx and normal mouse, respectively. These results show the delivery and expression of β-galactosidase and dystrohpin in mouse skeletal muscle following delivery of plasmid DNA encoding the respective genes.

TABLE 18

Luciferase expression in Mdx mouse.

| animal # | total expression of whole leg (ng luciferase) | expression of per gram muscle (ng luciferase/gram muscle) |
|---|---|---|
| 134 | 1691 | 1271 |
| 135 | 1738 | 1307 |
| 137 | 1248 | 1177 |
| 138 | 869 | 643 |
| 140 | 1641 | 1357 |
| 141 | 881 | 663 |
| average | 1345 | 1070 |

5. Delivery of Polynucleotides to Limb Skeletal Muscles in Dystrophic Dow: Juvenile male Golden Retriever dogs of 3 to 12 kg body weight underwent intra-arterial injections in their limbs following anesthesia. Anesthesia was with intravascular injection of propofol followed by isoflurane inhalant. For forearm injections, the arm was put at the extension and external rotation position and a 3 cm incision was made at the conjunction of armpit and upper arm and near the inside edge of the brachial biceps. After separating the brachial artery from the brachial vein and median nerve, a catheter (3-4F) was inserted anterograde into the brachial artery until the tip of the catheter reached to the elbow and was fixed by ligation. In some cases the brachial vein was clamped. Blood circulation of the forelimb was further inhibited by using a tourniquet placed around the upper limb up to the elbow (10 minutes maximum). For whole hindleg injections, an incision was made through the midline of the abdomen one inch below the umbilicus to the pubis. Connective tissue was separated to expose the common iliac artery and vein, external iliac artery and vein, internal iliac artery and vein, inferior epigastric artery and vein, superficial epigastric artery and vein, and the superficial iliac circumflex artery and vein. Clamps were placed on the inferior epigastric artery and vein, superficial epigastric artery and vein, and the superficial iliac circumflex artery and vein. An catheter (F5) was placed into the distal part of the iliac artery to the femoral artery and secured by ligation at the beginning of the femoral artery. Clamps are then placed on the external iliac vein, internal iliac artery and vein, and the common iliac artery and vein.

A 17% papaverine/saline solution was injected to increase vessel dilation (10-50 ml depending on animal size). After 5 minutes a plasmid DNA/saline solution was injected using a nitrogen-pressurized cylinder set at 65 psi. For the forelimbs, the injection volume was 50-200 ml. For whole leg injections, the injection volume was 60-500 ml. Injection rates varied from 20 s to 120 s. Two min after injection, the clamps and tourniquet were released and the catheters were removed.

Figure 2:
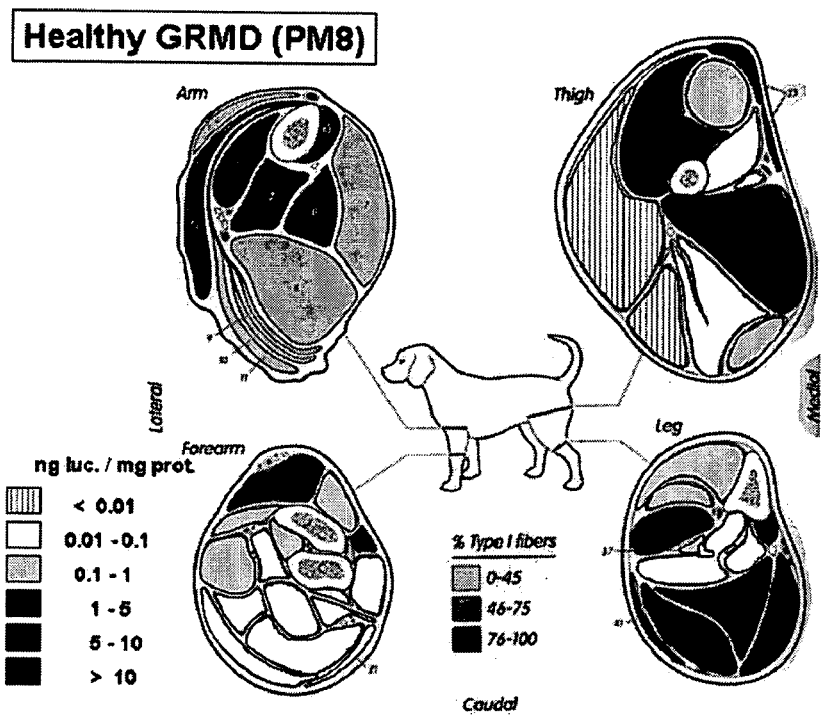
FIG. 2. Illustration of luciferase expression in leg muscles of dystrophic and normal dog after intra-arterial injection of pCI-Luc plasmid under elevated pressure. Panel A shows expression distribution in normal dog. Panel B shows expression distribution in dystrophic dog model.
Figure 2:
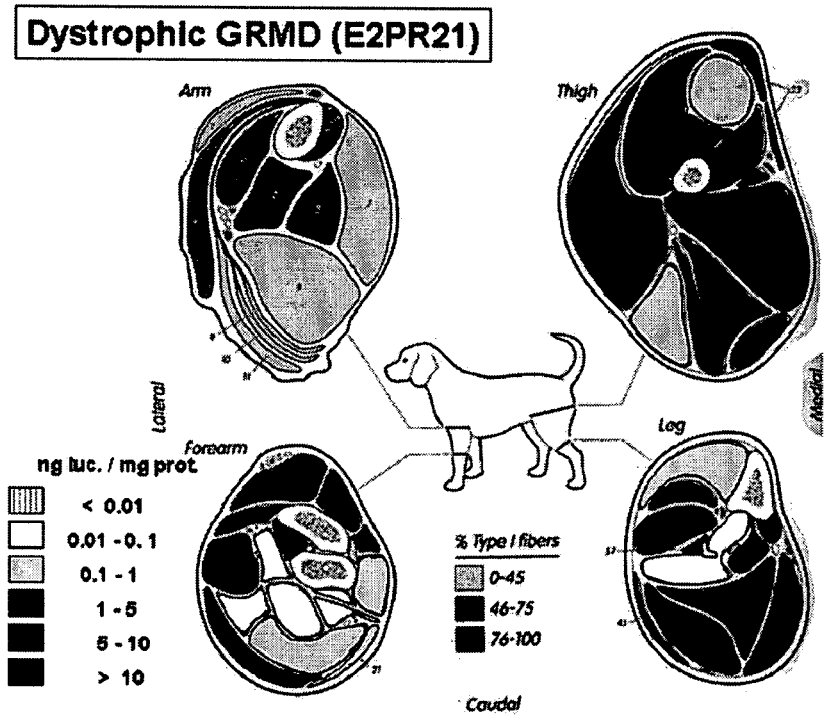

One forelimb and the opposite hindlimb or all four limbs were injected on day one with pMI-Luc+(20-50 mg) or the dystrophin plasmid (50-330 mg). In these vectors, the reporter genes are under transcriptional control of the muscle creatine kinase promoter, which has been shown to direct sustained, high level expression in muscle. The animals were sacrificed at 7 days and all muscles were analyzed for gene expression. Uninjected limbs or limbs injected with saline were used to test for revertants. Results are shown in Table 19 and graphically summarized in FIG. 2. FIG. 2A illustrates the distribution of luciferase expression in normal dog. FIG. 2B illustrates the distribution of luciferase expression in the dystrophic dog model.

TABLE 19

Luciferase expression after of delivery pCI-Luc polynucleotide in dog skeletal muscle cells. Numbers given in pg Luciferase per mg total protein.

| | | GRMD dog | | healthy dog | |
|---|---|---|---|---|---|
| | | left | right | left | right |
| antebrachial muscles | | | | | |
| dorsolateral | extensor carpi radialis | | 0.8 | | 633 |
| | extensor digitorum communis | 5 | 1570 | | 299 |
| | extensor digitorum lateralis | | 7915 | | 438.5 |
| | extensor carpi ulnaris | | 671 | | 21.5 |
| | extensor pollicis longus et indicis | | | | 2456.7 |

TABLE 19-continued

Luciferase expression after of delivery pCI-Luc polynucleotide in dog skeletal muscle cells. Numbers given in pg Luciferase per mg total protein.

| | | GRMD dog | | healthy dog | |
|---|---|---|---|---|---|
| | | left | right | left | right |
| | proprius | | 6763 | | |
| | | | 1672 | | |
| | abductor pollicis longus | | 4 | | 292.4 |
| | | | 1439 | | 1920.8 |
| | supinator | 9 | 5 | 3.3 | |
| caudal | flexor carpi radialis | 3 | 828 | 1.5 | 116.2 |
| | flexor carpi ulnaris | | 270 | | 6.1 |
| | flexor digitorum superficialis | | 2017 | | 43.5 |
| | flexor digitorum profundus | | 49 | | 11.3 |
| | pronator teres | | 9231 | 5.2 | 270.6 |
| | | | | | 1048.7 |
| forepaw | forepaw | 10 | 958 | 2 | |
| other | brachi radialis | | | | 545.1 |
| muscles of the crus | | | | | |
| craniolateral | tibialis cranialis | 980 | 1.4 | 1.7 | |
| | extensor digitorum longus | 992 | 0.3 | | |
| | peroneus longus | 4116 | 0.3 | 127.8 | |
| | peroneus brevis | | | 6.2 | |
| | extensor digitorum lateralis | | 0.2 | | |
| caudal | gastrocnemius | 4365 | 0.1 | 3 | 0.1 |
| | flexor digitorum profundus | 1912 | 1.9 | 3 | |
| | tibialis caudalis | | 0.4 | | |
| | popliteus | 9821 | 0.3 | | |
| other | Testes | 0.1 | | | |
| | Liver #1 | | 0.3 | | |
| muscles of the pelvic limb | | | | | |
| thigh | gluteus superficialis | | 1.4 | 4.9 | |
| | gluteus medius | 4 | 0.2 | 0.1 | |
| | sartorius | | | 661.2 | |
| | tensor fasciae latae | | 0.5 | 369.7 | |
| | | 1031 | | | |
| | biceps femoris | 2 | 1.1 | 0.1 | |
| | | | | 0.6 | |
| | semimembranosus | 5988 | 1.7 | 49.8 | |
| | semitendinosus | 432 | 1.1 | 0.1 | |
| | abductor magnus brevis | 4103 | 2 | 3644.8 | |
| | sartorius cranial part | 4664 | 0.9 | | |
| | rectus femoris | 396 | 0.1 | 179.9 | |
| | vastus medialis | 2588 | 0.5 | 7.4 | |
| | | | | 12448.7 | |
| | vastus intermedius | 4469 | 3.2 | | |
| | vastus lateralis | 2102 | 1 | 2927.8 | |
| | pectineus | 737 | 0.1 | 11.9 | |
| | gracilis | 1826 | 0.5 | 146 | |
| gluteal region and hip joint | piriformis | 14 | 1.2 | | |
| | gemellus | | 3 | | |
| | quadratus femoris | 911 | 0.1 | 1 | |
| | gluteus profundus | | 0 | 1.8 | |
| | obturator externus | | | 1.8 | |
| | biceps brachialis | | | | 0.1 |

6. Delivery of plasmid DNA to skeletal muscle in dog limb: Anesthesia was induced by injecting sodium thiopental (12.5 mg/kg IV) into the cephalic vein of the forepaw. Animals were intubated and anesthesia was maintained with isoflurane (1-2%)

Brachial Artery—The forelimb of the dog was rotated in a posterior position. The surgical field was prepped aseptically and draped. A 5 cm incision was made about 3-4cm above the elbow on the inside of the upperlimb. Connective tissue was separated to expose a 3 cm section of the brachial artery and vein. 3-0 silk ties were then placed around the proximal and distal ends of the exposed artery. A vascular clamp was placed on the proximal end of the brachial artery and adventitia was removed from the vessel surface. A small arteriotomy was made and a 4 French (modified angiography catheter—Cordis) was inserted a premeasured distance so that the tip of the catheter was 1-2 cm past (distal to) the tourniquet. The catheter was then secured in place with the 3-0 silk tie and flushed with heparinized saline. A vascular clamp was then placed on the brachial vein to prevent outflow and the tourniquet was tightened securely. A 17% papaverine /saline solution (30-50 ml depending on body weight) to increase vessel dilation was then injected by hand with a 50 cc syringe over 10 to 20 seconds. After 5 minutes, the catheter was connected to the infusion pump and the plasmid DNA/saline solution was injected (100-250 ml over approximately 20-60 seconds) After 2 minutes the tourniquet was released and the venous clamp was removed. The brachial artery catheter was then removed, the artery was repaired with 6-0 prolene suture and bleeding controlled with a hemostatic sponge. The subcutanous layers and skin were closed with appropriate suture.

Femoral Artery—The animal was positioned on the operating table in a dorsal recumbent position, prepped aseptically and draped for surgery. An incision was made in the upper leg to expose a 3-4 cm segment of the femoral artery. Connective tissue was removed from the femoral artery and vein and 3-0 silk ties were place around the proximal and distal ends of the artery. A vascular clamp was placed on the proximal end of the femoral artery and adventitia was removed from the vessel surface. A small arteriotomy was made and a 4 French (modified angiography catheter—Cordis) was inserted a premeasured distance so that the tip of the catheter was 1-2 cm past the tourniquet. The catheter was then secured in place with the 3-0 silk tie and flushed with heparinized saline. A vascular clamp was then placed on the brachial vein to prevent outflow and the tourniquet was tightened securely to further prevent fluid from leaving the limb. A 17% papaverine/saline solution (30-50 ml depending on body weight) to increase vessel dilation was then injected by hand with a 50cc syringe over 10 to 20 seconds. After 5 minutes, the catheter was connected to the infusion pump and plasmid DNA/saline solution was injected (100-250 ml over approximately 20-60 seconds). After 2 minutes the tourniquet was released and the venous clamp was removed. The femoral artery catheter was then removed, the artery was repaired with 6-0 prolene suture and bleeding controlled with a hemostatic sponge. The subcutaneous layers and skin were closed with appropriate suture.

Iliac Injection—The animal was positioned on the operating table in a dorsal recumbent position, prepped aseptically and draped for surgery. An incision was made through the midline of the abdomen 3 cm below the umbilicus to the pubis. A retractor was positioned inside the abdomen to hold the intestines and connective tissue was separated to expose the common iliac and femoral vessels. Connective tissue and adventitia were removed from a 3 cm segment of the iliac artery and 3-0 silk ties were passed around the proximal and distal ends. A vascular clamp was placed on the proximal end of the iliac artery, a small arteriotomy was made and a 4 French catheter (modified angiography catheter- Cordis) was advanced from the iliac artery into the external femoral artery. The catheter was secured with the 3-0 silk tie and flushed with heparinized saline. Vascular clamps to prevent outflow from the limb were placed on the iliac vein, external femoral vein, internal femoral artery and vein, epigastric trunk vessels and the superficial circumflex vessels. A 17% papaverine /saline solution (40 to 50 ml depending on body weight), to increase vessel dilation, was then injected by hand with a 50 cc syringe over 10 to 20 seconds. After 5 minutes, the catheter was connected to the infusion pump and a plasmid DNA/saline solution was injected (150-300 ml over approximately 20-60 seconds). After 2 minutes the clamps were removed and the injection catheter was removed. The iliac artery was repaired with 6-0 prolene suture and bleeding controlled with a hemostatic sponge. The abdominal wall and the skin were closed with appropriate suture.

At the completion of surgery animals were given antibiotics(pennicilin 300,000 units IM) and analgesics(banamine 16 mg IM). Anesthesia was turned off and the endotrachial tube was removed once the animal had regained a swallowing reflex. The animals were monitored continuously until they could maintain a sternal recumbent.

TABLE 20

|  | animal | | | | | |
| --- | --- | --- | --- | --- | --- | --- |
|  | 1 | 2 | 3 | 4 | 5 | 6 |
|  | | | animal weight (kg) | | | |
|  | 11.9 | 12.7 | 9.9 | 4.2 | 3.8 | 3.8 |
| Front Limb | blood pressure cuff | | | tourniquet | | |
| DNA (µg/ml) | 10 | 10 | 50 | 100 | 83 | 83 |
| volume (ml) | 50 | 100 | 120 | 100 | 120 | 120 |
| ml/g of muscle | 0.74 | 1.55 | 2.47 | 3.88 | 5.85 | 5.59 |
| ml/kg of body weight | 4.2 | 7.9 | 12.1 | 23.8 | 31.6 | 31.6 |
| injection rate (ml/sec) | 2.9 | 1.3 | 8.0 | 8.3 | 5.7 | 10.0 |
| luciferase total ng/g | 15 | 101 | 159 | 350 | 3921 | 7659 |
| Hind Limb | blood pressure cuff | | | tourniquet | clamps | |
| DNA (µg/ml) | 10 | 10 | 50 | 100 | 50 | 44.4 |
| volume (ml) | 75 | 150 | 180 | 100 | 200 | 225 |
| ml/g of muscle | 0.86 | 1.58 | 2.79 | 2.59 | 2.25 | 2.02 |
| ml/kg of body weight | 6.3 | 11.8 | 18.2 | 23.8 | 52.6 | 59.2 |
| injection rate ml/sec | 2.1 | 5.0 | 4.5 | 12.5 | 6.7 | 15.0 |
| luciferase total ng/g | 1 | 110 | 30 | 284 | 1180 | 18296 | to 20 seconds. After 5 minutes, the catheter was connected to the infusion pump and plasmid DNA/saline solution was 7. Polynucleotide Delivery to Limb Skeletal Muscle Cells in Monkeys: Seven Rhesus macaque monkeys (5 males; 2 females) of 6 to 13.7 kg body weight underwent intra-arterial injections in their limbs following anesthesia with ketamine and halothane. For the forearm injections, a longitudinal incision, 3 cm in length, was made on the skin along the inside edge of the biceps brachii and 2 cm above the elbow. After separating the artery from surrounding tissues and veins, a 20 g catheter was inserted into the brachial artery anterogradely and ligated in place. For the lower leg injections, the procedure was essentially the same as that used in the arm, but the incision was located on the upper edge of the popliteal fossae and the 20 g catheter was inserted into the popliteal artery.

For both the arm and leg injections, blood flow was impeded by a sphygmomanometer cuff surrounding the arm or leg proximal to the injection site. After the sphygmomanometer was inflated to more than 300 mmHg air pressure, the catheterized vessels were injected with 30 ml of normal saline containing 5 mg papaverine (Sigma Co.). Five min. later, a saline solution containing 100 μg pDNA/ml solution was rapidly injected within 30 to 45 sec. For the arms, the volume of each injection was 75 ml and 90 ml in the first two animals and 120 ml thereafter. The injection volume was 180 ml for the lower legs. The DNA solutions were injected using a nitrogen-pressurized cylinder. Two min after injection, the catheters were removed and the sphygmomanometer deflated.

The procedure was initially done on four monkeys in which one arm and leg was injected and muscle biopsies were taken at one (#1-3) or two weeks (#4). Monkey #2 had to be sacrificed at two weeks after injection because of an eye infection (unrelated to our procedure). Three more monkeys (#5-7) received an injection in all four extremities (one arm and leg on one day and the other two extremities two days later). Muscle biopsies were obtained at one week and the animals were sacrificed at two weeks after the injections. In monkeys #6 and #7, an arm and leg were injected with pCI-LacZ; all other injections were with pCI-Luc$^+$.

Luciferase assays were performed on muscle biopsies, entire muscles and various tissues. The relative light units (RLU) were converted to nanograms of luciferase by using luciferase standards (Molecular Probes, Eugene, OR) and a standard curve in which luciferase protein (pg)=RLU×5.1×$10^{-5}$. For the β-galactosidase assays, muscle samples were taken from the proximal, middle, and distal positions of each muscle, cut into small pieces, frozen in cold isopentane, and stored at $-80°$ C. Muscle pieces were randomly chosen from each muscle sample (for every position) and 10 μm-thick cryostat sections were made. Every tenth section, for a total of 20 sections, was stained and analyzed. The sections were incubated in X-gal staining solution (5 mM potassium ferricyanide, 5 mM potassium ferrocyanide, 1 mM magnesium chloride, 1 mM X-gal in 0.1 M PBS, pH 7.6) for 4-8 h at RT and counterstained with hematoxylin and eosin. Three sections were selected randomly from the 20 sections of each position (usually the 4th, 11th and 17th sections, but an adjacent section was used if these sections were not intact). As previously described, the number of β-galactosidase-positive and total cells were determined within a cross area in each section by moving the counter grid from the top edge of the section to the bottom and from the left edge to the right. The percentage of β-galactosidase-positive cells for each muscle was gotten from the result of positive number divided by total cell number. A weighted average for the percent of transfected cells for each extremity muscle was determined as follows: (ZAi*Mi)/M where Ai is percent of transfected cells for one muscle, Mi—weight of that muscle and M—whole weight of all muscles. For the co-localization of β-galactosidase and GFP expression, 10 μm-thick cryostat sections were fixed with 4% formaldehyde for 5-10 min. Mouse-anti-β-galactosidase antibody and TRITC—labeled goat-anti-mouse IgG (Sigma) were used as primary and secondary antibodies, respectively. Using a Nikon Optiphot epifluorescence microscope with a SenSys CCD Camera (Photometrics, Tucson, Ariz.), two images were collected from the same view for TRITC-labeled β-galactosidase and for GFP and merged together using the program Adobe Photoshop 4.0.

All seven monkeys tolerated the procedure well and had full function of their arms, hands, legs and feet following the procedure. In particular, there was no indication of damage to the radial nerve, which could have been sensitive to the inflated sphygmomanometer surrounding the upper arm. Swelling in the target limbs, a putative correlate of successful gene transfer, was noted afterwards but completely subsided within one day. When the monkeys awakened from the anesthesia, 15 to 30 min after the procedure, they did not appear to be in any discomfort beyond that of normal surgical recovery. Occasionally, the skin in the target limb had some spots of hemorrhage which resolved within several days.

Four of the monkeys were sacrificed at 14 to 16 days after injection and all the target muscles of their limbs were assayed for either luciferase or β-galactosidase expression. These results indicate that the intra-arterial injection of pCI-Luc$^+$ DNA yielded levels of luciferase expression in all muscles of forearm, hand, lower leg and foot, ranging from 345 to 7332 ng/g muscle (Table 21). The variability in luciferase expression in arm muscles for different animals appears dependent upon whether the tip of the catheter was positioned in the radial or ulnar artery. The average luciferase expression levels in the limb muscles were 991.5±187 ng/g for the arm and 1186±673 ng/g for the leg.

Figure 3:
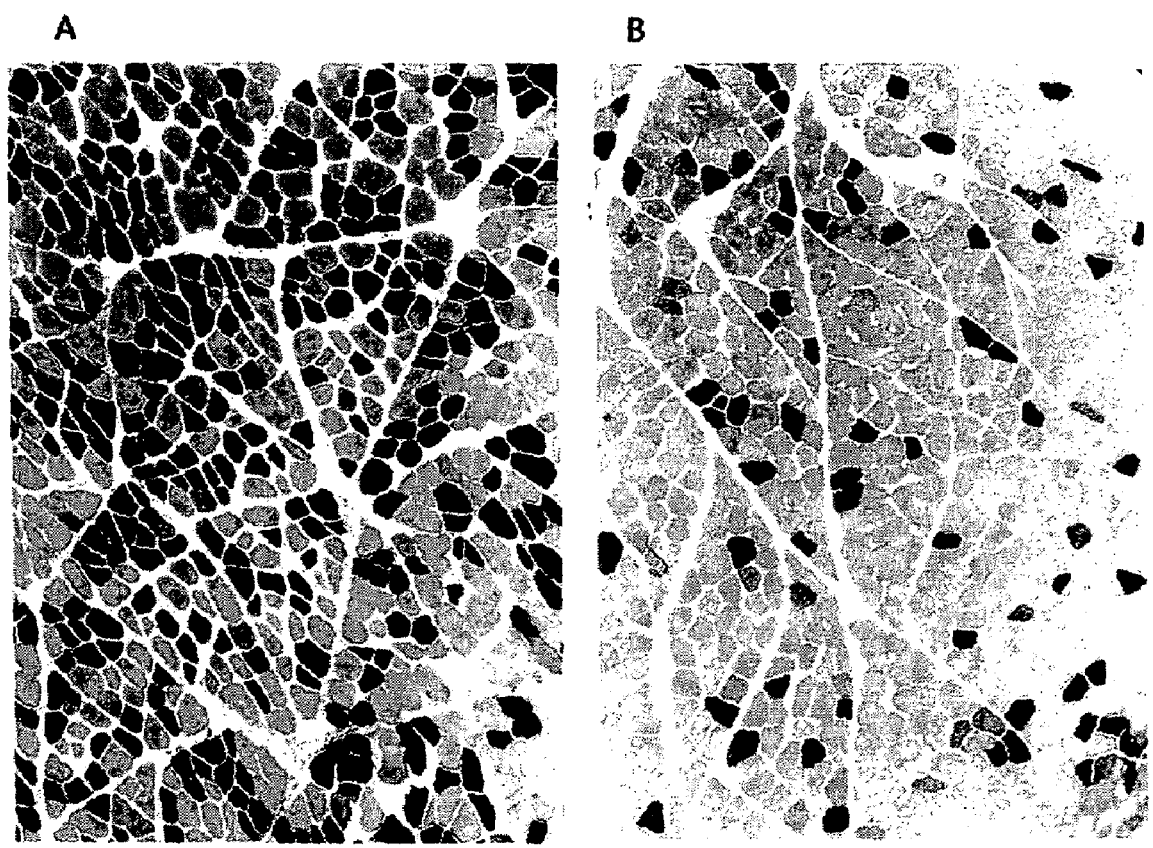
FIG. 3. Photomicrographs of muscle sections histochemically stained for β-galactosidase expression. Panel A represents a muscle (pronator teres) with a high level of expression; Panel B represents a muscle (abductor pollicis longus) with an average level of expression. Magnification: 160×.
Figure 4:
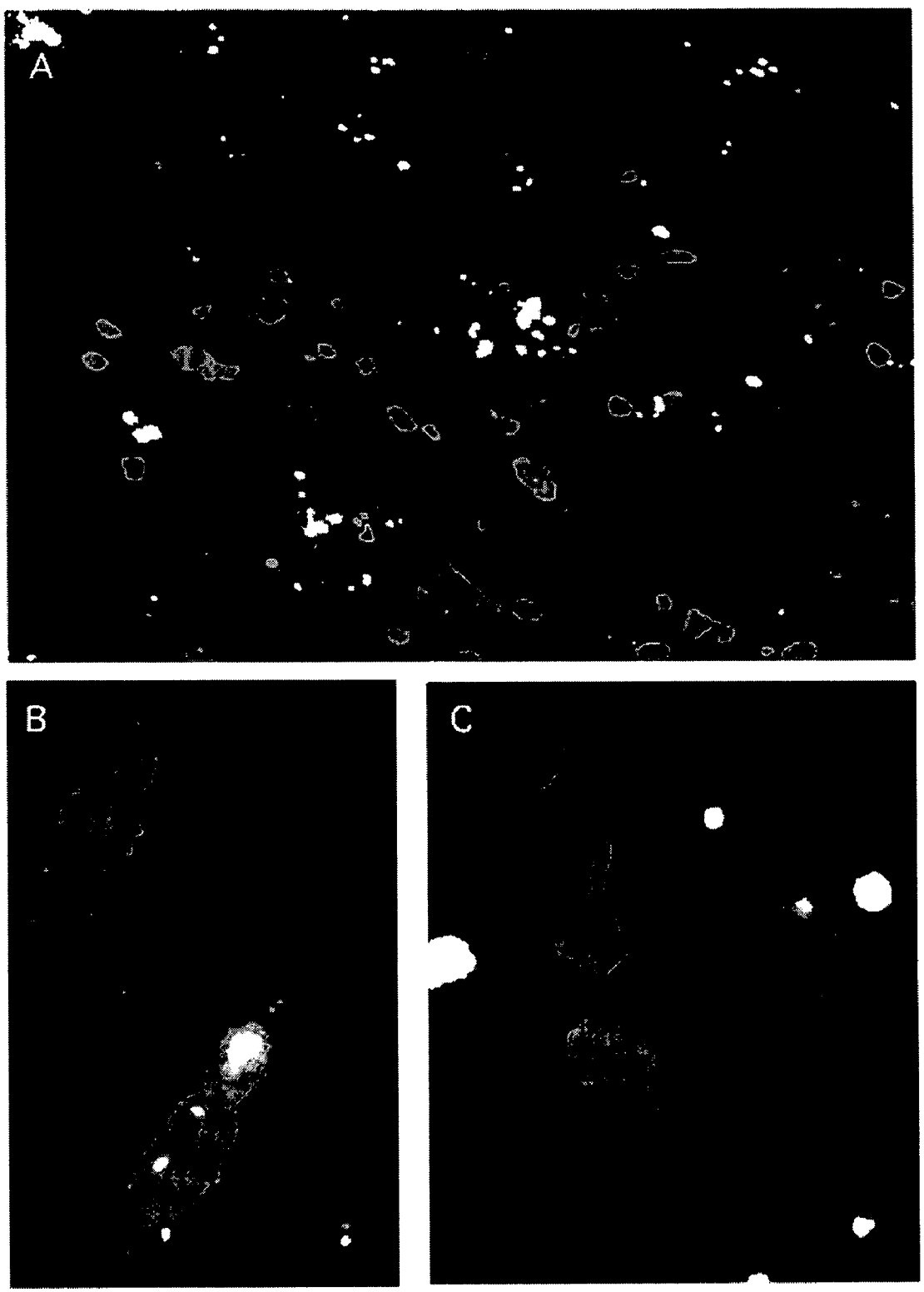
FIG. 4 Expression of β-galactosidase (light grey) and GFP (white) in rat muscle injected intra-arterially at different times with the respective expression pDNAs. Panel A (640× magnification) is a low-power field illustrating that expression of β-galactosidase and GFP were typically not co-localized. Panels B and C are high power fields (1600× magnification) that show an example of co-localization (B) and separate expression (C)

After intra-arterial injection of pCI-LacZ DNA, β-galactosidase expression was found in myofibers. Large numbers of β-galactosidase-positive myofibers were found in both leg and arm muscles, ranging from less than 1% to more than 30% in different muscles (Table 21 and FIG. 3). The average percentage for all four limbs injected was 7.4%, ranging from 6.3% to 9.9% for each of the limbs. The β-galactosidase percentages for specific muscle groups positively correlated with the luciferase levels in the same muscles (r=0.79).

TABLE 21

Mean muscle β-galactosidase or luciferase expression in four muscles from monkeys sacrificed two weeks after injection of pCI-LacZ or pCI-Luc$^+$. "±" indicates standard error; n indicates the number of limbs assayed.

| Arm Muscles | | | β-galactosidase (% positive) (n = 2) | Luciferase (ng/g muscle) (n = 5) |
|---|---|---|---|---|
| Anterior group | Superficial group | palmaris longus | 5.9 ± 0.9 | 2368 ± 1309 |
| | | pronator teres | 19.9 ± 9.4 | 1818 ± 336 |

TABLE 21-continued

Mean muscle β-galactosidase or luciferase expression in four
muscles from monkeys sacrificed two weeks after injection
of pCI-LacZ or pCI-Luc⁺. "±" indicates
standard error; n indicates the number of limbs assayed.

|  |  |  |  |  |
|---|---|---|---|---|
| Posterior group | Deep group | flexor carpi radialis | 7.8 ± 0.7 | 1885 ± 762 |
|  |  | flexor carpi ulnaris | 3.8 ± 3.0 | 852 ± 314 |
|  |  | flexor digitorum superficialis | 7.7 ± 1.2 | 1009 ± 189 |
|  |  | flexor digitorum profundus | 1.0 ± 0.5 | 544 ± 360 |
|  |  | pronator quadratus | 14.3 ± 11.1 | 1884 ± 331 |
|  | Superficial group | brachioradialis | 9.0 ± 8.7 | 1148 ± 942 |
|  |  | extensor carpi radialis longus | 6.6 ± 6.3 | 1179 ± 584 |
|  |  | extensor carpi radialis brevis | 9.4 ± 4.5 | 1118 ± 325 |
|  |  | extensor digitorum | 6.2 ± 5.4 | 1184 ± 94 |
|  |  | anconeus | 2.0 ± 0.3 | 1744 ± 372 |
|  |  | extensor carpi ulnaris | 0.6 ± 0.4 | 371 ± 86 |
|  |  | extensor pollicis longus | 6.9 ± 4.3 | 927 ± 228 |
|  | Deep group | supinator | 15.1 ± 9.3 | 2398 ± 748 |
|  |  | abductor pollicis longus | 6.2 ± 3.8 | 927 ± 228 |
|  |  | extensor digiti secund et teriti | 6.0 ± 5.5 | 642 ± 168 |
|  |  | extensor digiti quart et minimi | 4.0 ± 3.5 | 593 ± 140 |
| Muscles of hand |  | muscle of thumb | 15.7 ± 0.5 | 904 ± 494 |
|  |  | interosseus | 17.3 ± 4.3 | 1974 ± 185 |
| Weighted Average |  |  | 6.3 ± 0.04 | 991 ± 187 |

|  |  | Leg Muscles | β-galactosidase (% positive) (n = 2) | Luciferase (ng/g muscle) (n = 2) |
|---|---|---|---|---|
| Posterior group | Superficial group | gastrocnemius | 3.0 ± 2.5 | 743 ± 33 |
|  |  | soleus | 21.2 ± 1.4 | 2888 ± 2151 |
|  | Deep group | popliteus | 37.1 ± 0.5 | 4423 ± 2657 |
|  |  | flexor digitorum longus | 8.9 ± 2.4 | 3504 ± 2151 |
|  |  | flexor hallucis longus | 9.7 ± 2.4 | 1355 ± 1224 |
|  |  | tibialis posterior | 28.7 ± 4.3 | 7332 ± 5117 |
| Anterior group |  | tibialis anterior | 2.8 ± 0.2 | 716 ± 162 |
|  |  | extensor hallucis longus | 4.2 ± 1.4 | 810 ± 497 |
|  |  | extensor digitorum longus | 10.9 ± 1.0 | 3187 ± 1166 |
|  |  | abductor hallucis longus | 2.2 ± 0.2 | 345 ± 104 |
| Internal group |  | peronaus longus | 6.3 ± 2.5 | 626 ± 383 |
|  |  | peronaus brevis | 8.9 ± 1.3 | 1300 ± 23 |
| Muscles of foot |  | extensor digitorum brevis | 6.2 ± 5.0 | 672 ± 607 |
|  |  | extensor hallucis brevis | 2.4 ± 1.8 | 672 ± 607 |
| LEG MUSCLES Weighted Average |  |  | 7.3 ± 0.1 | 1692 ± 768 |

While it was possible that this large amount of fluid might adversely affect the animal's cardiovascular or hemodynamic status, no adverse effects on the animals were observed. Serum chemical and histological analyses were performed to determine if the procedure caused any adverse effects in the monkeys. The serum levels of creatine phosphate kinase (CK), alanine aminotransferase, aspartate aminotransferase (AST) and lactate dehydrogenase (LDH) after surgery were several times higher than before surgery. Levels peaked at 48 hours post-injection and returning to normal within several days. Other serum enzymes such as γ-glutamyltransferase (GGT) and alkaline phosphatase, hematological assays (hematocrit and RBC indices, platelets), serum electrolytes (Na, Cl, K), serum minerals (calcium, phosphate, iron), serum proteins (albumin, total protein), serum lipids (cholesterol, triglycerides), renal indices (urea, creatinine), and bilirubin were unaffected. Total WBC increased within the typical range post-surgery. Limb muscles were obtained 14 to 16 days after intra-arterial injection and examined histologically. The vast majority of muscle tissue was well preserved and did not show any sign of pathology. In a few sections, mononuclear cells were noted surrounding β-galactosidase positive myofibers, some of which were undergoing degeneration. Immunostaining for CD-markers indicated that the majority of infiltrating cells were CD3-positive (T lymphocytes) with only a few B cells.

8. Delivery of plasmid DNA to heart muscle cells via intravascular delivery: The hearts of 30-40 kg domestic pigs were accessed via a limited left thoracotomy through the fifth intercostal space. A 27-gauge needle was inserted into a left anterior descending (LAD, great cardiac) or right posterior descending (middle cardiac) vein or artery, and ligated in place. The ligation serves to keep the needle in place and to direct flow distal from the needle. The corresponding artery or vein was transiently occluded during the injection. A pre-injection into the coronary artery or vein of 6 ml papaverine solution (0.5 mg/ml) was given in 15-20 seconds. After 5 minutes, a solution of 50 μg/ml plasmid pCI-Luc⁺ in 20 ml saline with 15% mannitol (w/v) was injected in 20-30 seconds. pCI-Luc⁺ is a plasmid DNA expression vector in which an optimized version of the firefly luciferase gene (Promega, Madison, Wis.) is expressed under transcriptional control of the CMV promoter (basic expression vector is pCI, Promega, Madison, Wis.). Following injection, the ligation and needle were removed, bleeding stopped, and the pericardium and chest closed. In most pigs, the LAD bed and a site in the circumflex were injected. In two pigs, also direct interstitial injections were performed for comparison. Two days following injection, the animals were sacrificed and sections from the injection site were excised and assayed for reporter gene expression. Sections from the heart (ca. 1.5 gram each) were homogenized in a Triton X-100 lysis buffer. Luciferase activity was measured with an Analytical Luminescence Laboratories luminometer. Activity levels are expressed as the amount of luciferase protein per gram of heart tissue.

Luciferase expression in the area around the injection site averaged 26.2 ng/g tissue (range 2.3-61.8; n=5). Both arterial and venous delivery resulted in efficient luciferase expression. In one animal, we compared intravenous delivery while transiently occluding the corresponding artery with leaving arterial flow open. Luciferase expression levels were 7.22 vs. 7.76 ng/g, respectively. This suggests that the capillary bed itself accounts for sufficient resistance to retrograde flow to increase vascular permeability above the required threshold for efficient plasmid DNA extravasation.

Direct interstitial injection of 500 µg plasmid DNA in 500 µl saline resulted in an average expression level of 70.3 ng luciferase per gram tissue (range 9.6-115.2; n=3). Expression appeared far more limited to the area of injection. Analysis of tissues around the injected bed after intravascular delivery, showed lower levels of expression extending to relatively distant sites.

9. Plasmid DNA Delivery to Heart Muscle Cells via Catheter Mediate Coronary Vein Injection: 30-50 kg Yorkshire domestic swine (Sus scrofa) were sedated with telezol (20-30 mg IM), induced with pentobarbitol (250-500 mg IV), and endotracheally intubated. Anesthesia was maintained with inhaled isoflurane (0.5 -3%). The right carotid artery and internal jugular vein were exposed by surgical cutdown and coronary angiography was performed. Heparin (100 U/kg, IV) was administered. A 10 Fr guiding catheter was advanced to the coronary sinus, and a 7 Fr balloon-tipped triple lumen catheter was advanced over a 0.014 inch guidewire into the cardiac vein draining the left anterior descending (great cardiac vein) or right posterior descending (middle cardiac vein) territories. Injections of diluted iodinated contrast were used, in conjunction with the coronary angiogram, to delineate the myocardial territory drained by each vein.

The larger lumen of the balloon-tipped triple lumen catheter was used for fluid injection, while the smaller lumen was used to monitor cardiac vein pressures during plasmid DNA infusion. The third lumen was used to inflate and deflate the balloon. Following placement of the catheter, the balloon was inflated, and 6 ml saline or 6 ml saline with 3 mg papaverine was instilled through the large lumen (which opened distal to the balloon). The installation required 3-20 seconds and resulted in slightly increased venous pressure (10 - 350 mm Hg). After 5 minutes, the balloon was deflated for 20-30 seconds and then inflated again followed by injection solution delivery. A saline solution containing 100 µg/ml pCI-Luc+ was rapidly delivered through the main lumen. 25-30 ml injection solution was injected in 8-20 seconds. Intravenous pressure increased (120-500 mmHg). In some pigs, two sites were injected (one in the posterior descending, the other in the left anterior descending territory); in other pigs, only one site was injected (left anterior descending).

Two days following injection, the animals were sacrificed, the heart excised, divided in 1-2 gram sections, and assayed for reporter gene expression. Expression levels varied from 1.4 to 456.9 ng luciferase per gram of heart tissue (n=8).

10. Delivery of polynucleotide to the diaphragm in monkey: The monkey was anesthetized with ketamine followed by halothane inhalation. A 2 cm long incision was made in the upper thigh close to the inguinal ligament just in front of the femoral artery. Two clamps were placed around the femoral vein after separating the femoral vein from surrounding tissue. At an upstream location, the femoral vein was ligated by the clamp and a guide tube was inserted into the femoral vein anterogradely. A French 5 balloon catheter (D 1.66 mm) with guide wire was inserted into the inferior vena cava through the guide tube and an X-ray monitor was used for instructing the direction of guide wire. The guide wire was directed into the inferior phrenic vein. The catheter position in the inferior phrenic vein was checked by injecting iodine. The balloon was inflated to block blood flow through the inferior phrenic vein. 20 ml 0.017% papaverine in normal saline was injected. 5 minutes after papaverine injection, 40 ml of DNA solution (3 mg) was injected in 65 sec (0.615 ml/sec). 2 minutes after DNA injection, the balloon was released and the catheter was removed. The animal was sacrificed and the diaphragm was taken for luciferase assay 7 days after the procedure. The results indicate successful delivery of plasmid DNA to the portion of the diaphragm supplied by the injected vessel.

TABLE 22

Luciferase expression in diaphragm from monkey sacrificed 7 days after injection of pCI-Luc+.

| diaphragm section | total luciferase (ng) | ng luciferase/ gram if tissue |
|---|---|---|
| anterior part of left side | 0 | 0 |
| posterior part of left side | 0 | 0 |
| left conjunction area | 0 | 0 |
| anterior part of right side | 221.94 | 27.88 |
| posterior part of right side | 15.98 | 2.12 |
| right conjunction area | 34.21 | 17.82 |

11. Delivery of DNA/polycation complexes to prostate and testis via injection into dorsal vein of penis: DNA and L-cystine-1,4-bis(3-aminopropyl)piperazine cationic copolymer were mixed at a 1:1.7 wt:wt ratio in water, diluted to 2.5 ml with Ringers solution and injected rapidly into the dorsal vein of the penis (within 7 seconds). For directed delivery to the prostate, clamps were applied to the inferior vena cava and the anastomotic veins just prior to the injection and removed just after the injection (within 5 -10 seconds). Mice were sacrificed 24 h after injection and various organs were assayed for luciferase expression. The results, Table 23, show efficient and functional delivery of DNA containing complexes to prostate, testis and other tissues.

TABLE 23

Delivery of DNA containing plasmid to prostate and testis via injection in dorsal vein.

| Organ | Luciferase (RLUs) |
|---|---|
| Prostate | 129,982,450 |
| Testis | 4,229,000 |
| fat (around bladder) | 730,300 |
| bladder | 618,000 |

12. Delivery of plasmid DNA to liver cells via injection into the bile duct vessel: Retrograde injection was used to deliver nucleic acid expression cassettes to hepatocytes in mouse, rat, and dog. Repetitive injections of a therapeutic gene into the bile duct were also accomplished.

The pCILuc plasmid expresses a cytoplasmic luciferase from the human CMV immediately early (hCMV ID) promoter. pCILux expresses peroxisomal luciferase under control of the hCMV IE promoter. pCILacZ plasmid expressed the 0-galactosidase gene. The pCMVGH expresses human growth hormone.

Plasmid delivery into the hepatic vessels was performed in 6 week old ICR mice, 2.5 6.25 month old, 200-300 gram Sprague Dawley rats, and beagle dogs. Ventral midline incisions were performed to expose the liver and associated vessels. The mice were anesthetized with intramuscular injections of 1000 μg of ketamine HCl (Parke Davis, Morris Plains, N.J.) and by inhalation of methoxyflurane (Pitman Moore, Mudelein, Ill.) as needed. The rats were anesthetized with ether and the dogs were anesthetized with halothane by inhalation. Plasmids were injected in solutions containing 2.5 units/ml or heparin (Qian et al. 1991; Lypho Med, Inc., Chicago, Ill.) and either normal saline (0.9% NaCl) or 15% mannitol in normal saline (Sigma Chemical Co., St. Louis, Mo.).

Bile duct injections in mice were performed using manual injections with a 30-gauge, ½ inch needle and 1 ml syringe. A 5×1 mm, Kleinert Kutz microvessel clip was used to occlude the bile duct downstream from the point of injection in order to prevent flow to the duodenum and away from the liver. The gallbladder inlet was not occluded. In some of the bile duct injections, the junction of the hepatic vein and caudal vena cava clamped as above. In yet other injections, the portal vein and hepatic artery were clamped in addition to the occlusion of the hepatic vein. Repetitive injections into the bile duct were done by placing a polyethylene tube (I.D. 0.28 mm, O.D. 0.61 mm; Intramedic Clay Adams Brand, Becton Dickinson Co., Sparks, Md., USA) catheter into the bile duct after making a hole with a 27 gauge needle. The tubing was secured by a suture around the bile duct and tubing; thereby occluding the bite duct. The other end of the tubing was placed outside the skin of the animal's back so that surgery was not required for repeat injections. No blood vessel occlusions were done for these repetitive administrations. After completion of the studies, anatomical examination indicated that the catheter remained in the bile duct. In rats, bile duct injections were done as in mice. For the bile duct injections in dog, a suture was applied to transiently occlude the bile duct downstream from the point of injection. A DeBakey multipurpose vascular clamp was applied to the cystic duct during injection to prevent the injection solution from entering the gallbladder.

One day after injections, the animals were sacrificed and the rodent livers were divided into 6 sections composed of right lateral lobe, caudate lobe, two pieces of median lobe and two pieces of left lateral lobe. Mouse liver sections were added to 0.7 ml lysis buffer (0.1% Triton X-100, 0.1 M potassium phosphate, 1 mM DTF pH 7.8). For rats, liver sections were added to 4 ml lysis buffer. For the dog livers, approximately 10% of each lobe was divided into 5-20 pieces and placed into 2 ml lysis buffer. The samples were homogenized using a PRO 200 homogenizer (PRO Scientific Inc., Monroe, Conn.) and centrifuged at 4,000 rpm for 10 min at 4° C. 20 gl supernatant was analyzed for luciferase activity. Relative light units (RLU) were converted to pg of luciferase using standards from Analytic Luminescence Laboratories (ALL, San Diego, Calif.). Luciferase protein (pg)=$5.1 \times 10^5 \times$ RLU+3.683 ($r^2$=0.992).

For mouse bile ducts injected with 100 μg pCILuc in 1 ml 15% mannitol +2.5 units heparin/ml in normal saline solution, mean total luciferase protein/liver of 15.39 μg/liver was obtained when the hepatic vein was clamped. A mean total luciferase protein/liver of 1.33 μg/liver was obtained without occluding the hepatic vein. If mannitol was omitted then the bile duct injections without clamping any blood vessels yielded approximately 1 5-fold less luciferase (0.086 μg/liver+0.06, n=25). Clamping the hepatic artery and portal vein in addition to the hepatic vein did not improve expression beyond what was obtained when only the hepatic vein was clamped (data not shown). In rat, injections of 750 μg of pCILuc in 5-8 ml without any outflow obstruction yielded an average of 1.3 μg of luciferase/liver.

In dogs, 20 mg pCILux in 200 ml injection solution was injected at a rate of 66 ml/min into the bile duct without blocking outflow by occluding the IVC. Luciferase expression was found to be evenly distributed throughout the liver. Total LUX protein in the liver calculated to be 2.96 μg.

10 μm thick tissue sections were stained for β-galactosidase expression using 1-4 hour Xgal incubations (Budker, et al., 1996). Hematoxylin was used for the counterstain but the alkaline step was omitted so that the hematoxylin stain remained red. The percent of blue stained cells in the liver sections was determined by counting 3000 cells in three sections and averaging. Delivery of β-galactosidase expression vector was observed in 5-10% of hepatocytes. The percent of cells stained positive for β-galactosidase correlated with the levels of luciferase expression.

Serum ALT and GGT assays were performed on mice one and eight days after each of the above injections with pCILuc (4 mice for each condition). No increases in GOT were observed. Serum ALT levels increased to 200-400 U/L one day after bile duct injections. Eight days after injection, serum ALT levels decreased to baseline levels in all animals.

Repeat Bile Duct Injections: The bile ducts of mice were cannulated and 100 μg of pCMVhGH in 1 ml of 15% mannitol in normal saline were injected once a week. Serum levels of hGH increased one day after injection and then decreased to background levels by seven days after injection. One day after the second injection, hGH levels again increased and then were back to background levels by seven days after the second injection. Only minimal increases in hGH levels occurred after the third injection. Mice that had the highest levels after the first injection had the lowest levels after the second injection (mice 3 and 6) and vice versa (mice 1, 2, and 4). In another set of animals (4 mice), the bile duct injections were repeated four times with pCMVhGH and then pCILuc was injected. The first three pCMVhGH injections led to similar increases in hGH serum levels. Although there were only minimal raises in hGH serum levels following the fourth injection, injection of pCILuc yielded an average of 29.2 ng/liver (±7.1, n=3). The liver in one of the four mice was grossly yellow and scarred as a result of the bile duct ligation and did not express any luciferase. The decrease in hGH expression following repeat procedures is presumed to result from immune response since the same animals expressed luciferase following pCILuc delivery. These results demonstrate efficient plasmid delivery following injection of expression vector in solution into the bile duct in mice, rat and dog. Occlusion of other vessels to restrict outflow of the injection solutions enhanced but was not critical for efficient expression. Expression of luciferase or β-galactosidase was evenly distributed throughout the entire liver. Furthermore, these results demonstrate the utility of the invention for use in repeat delivery. High luciferase expression was observed after a fourth delivery procedure. Such repeat delivery procedure would be useful for the treatment of genetic disorders such as hemophilia. The bile duct could be accessed repeatedly by upper gastrointestinal endoscopy. Similarly, the hepatic vein could be non-invasively accessed via peripheral or central veins. In addition, gene transfer could be delivered to newborns via the umbilical cord vessels to get them over a newborn metabolic crisis as occurs in the organic acidunas and the urea cycle defects.

13. Repetitive Injections to Target a Larger Percentage of Myofibers: In order to explore the ability to access different populations of myofibers, the same leg in rats were injected with the 500 μg of the β-galactosidase plasmid (pCI-LacZ) and two days later with 500 μg of the nuclear GFP plasmid (pEBFP-N1). At two days after the last injection, the muscles were analyzed for expression of the two reporter genes. Expression of GFP and β-galactosidase was most often located in different myofibers (FIGS. 2A and C), but in some cells expression was coincident (FIG. 2B).

14. Adenoviral vectors can be delivered to muscle parenchymal cells by an intravascular route. An adenoviral vector CMVLacZ that expresses the E. coli β-galactosidase from the immediate early promoter of the human cytomegalovirus (CMV) was prepared as previously described (Yang et al. 1996) The rat iliac artery injection was performed as above. 0.5 mg of papaverine and 40 ng of collagenase in 3 ml saline was pre-injected while blocking the iliac artery and vein. $5\times^8$ particles of the adenoviral vector CMVLacZ in 10 ml of saline was injected in about 10 sec. After 2 minutes, the clamps were opened. Two days after injection, leg muscle cells were assayed for luciferase as above. Delivery was monitored be expression of luciferase encoded within the adenovirus genome. The results summarized in Table 24 demonstrate the delivery of Adenovirus to multiple muscle groups in the leg.

TABLE 24

Delivery of adenovirus expressing a luciferase gene to skeletal muscle via iliac injection.

| Muscle Group | Luciferase (ng) |
|---|---|
| Upper Leg Anterior | 59.04 |
| Upper Leg Posterior | 18.33 |
| Upper Leg Medial | 4.44 |
| Lower Leg Posterior | 11.04 |
| Lower Leg Anterior | 5.33 |
| Foot | 0.22 |
| Total | 98.40 |

15. Delivery of siRNA to muscle cells in rat via an intra-iliac administration route: 10 μg pGL3 control and 1 μg pRL-SV40 with 5.0 μg siRNA-luc+ or 5.0 siRNA-ori were injected into iliac artery of rats. Specifically, animals were anesthetized and the surgical field shaved and prepped with an antiseptic. The animals were placed on a heating pad to prevent loss of body heat during the surgical procedure. A midline abdominal incision was made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins to block both outflow and inflow of the blood to the leg. An efflux enhancer solution (e.g., 0.5 mg papaverine in 3 ml saline) was injected into the external iliac artery though a 25 g needle, followed by the plasmid DNA and siRNA containing solution (in 10 ml saline) 1-10 minutes later. The solution was injected in approximately 10 seconds. The microvessel clips were removed 2 minutes after the injection and bleeding was controlled with pressure and gel foam. The abdominal muscles and skin were closed with 4-0 dexon suture.

Four days after injection, rats were sacrificed and the quadriceps and gastrocnemius muscles were harvested and homogenized. Luc+ and Renilla Luc activities were assayed using the Dual Luciferase Reporter Assay System (Promega). Ratios of Luc+ to Renilla Luc were normalized to the siRNA-ori control. siRNA-Luc+ inhibited Luc+ expression in quadriceps and gastrocnemius by 85% and 92%, respectively, compared to the control siRNA-ori. Thus siRNA was effectively delivered to muscle cells in the leg using the delivery procedure.

Figure 5:
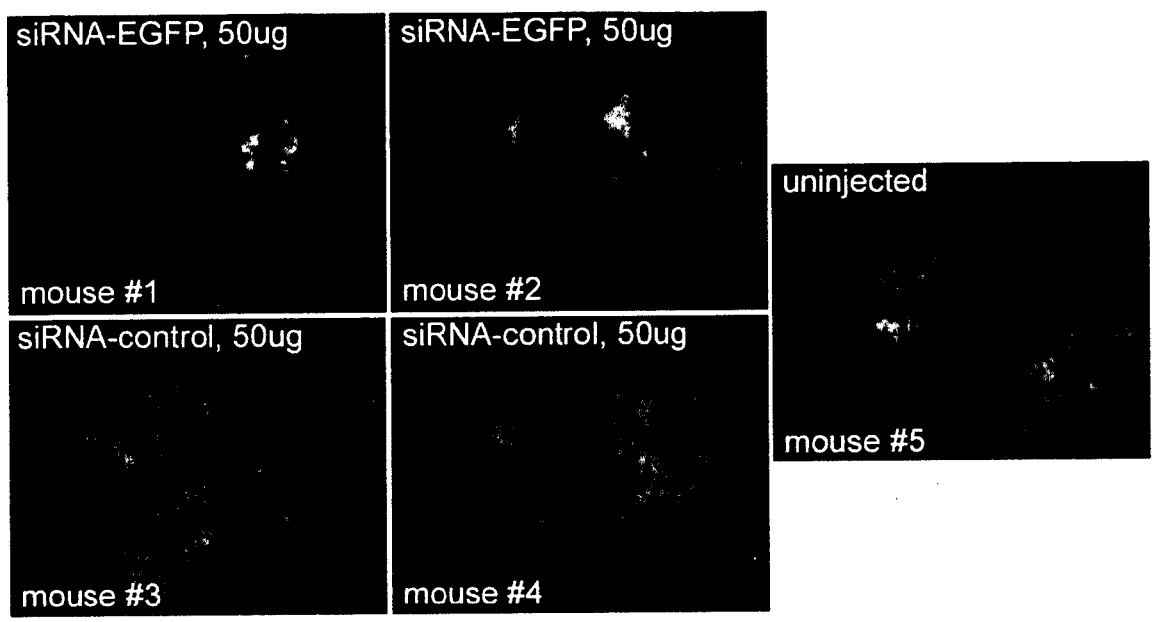
FIG. 5. Intravascular delivery of siRNA inhibits EGFP expression in the liver of transgenic GFP mice. Mice were injected with 50 µg siRNA, control siRNA or were not injected. Livers were harvested 30 h post-injection, sectioned, fixed, and counterstained with Alexa 568 phalloidin in order to visualize cell outlines. GFP and Alexa568 fluorescence was detected using a Zeiss Axioplan fluorescence microscope outfitted with a Zeiss AxioCam digital camera.

16. Delivery of siRNA to liver in mouse via tail vein injection. 10 week old, commercially available C57BL/6-TgN (ACThEGFP)10sb mice (The Jackson Laboratory) has been reported to express enhanced green fluorescent protein (EGFP) in all cell types except erythrocytes and hair. These mice were injected with EGFP specific siRNA (siRNA-EGFP) or control siRNA (siRNA-control) using the tail vein intravascular injection method described previously. 30 h post-injection, the animals were sacrificed and sections of the liver were prepared for fluorescence microscopy. Liver sections from animals injected with 50 μg siRNA-EGFP displayed a substantial decrease in the number of cells expressing EGFP compared to animals injected with siRNA-control or mock injected (FIG. 5). The data shown here demonstrate effective delivery of siRNA-EGFP to the liver. The delivered siRNA-EGFP then inhibited EGFP gene expression in the mice. We have therefore shown the ability of siRNA to inhibit the expression of an endogenous gene product in post-natal mammals. Cell outlines were visualized by counterstaining tissue sections with actin-binding Alexa568-phalloidin.

Figure 6A:
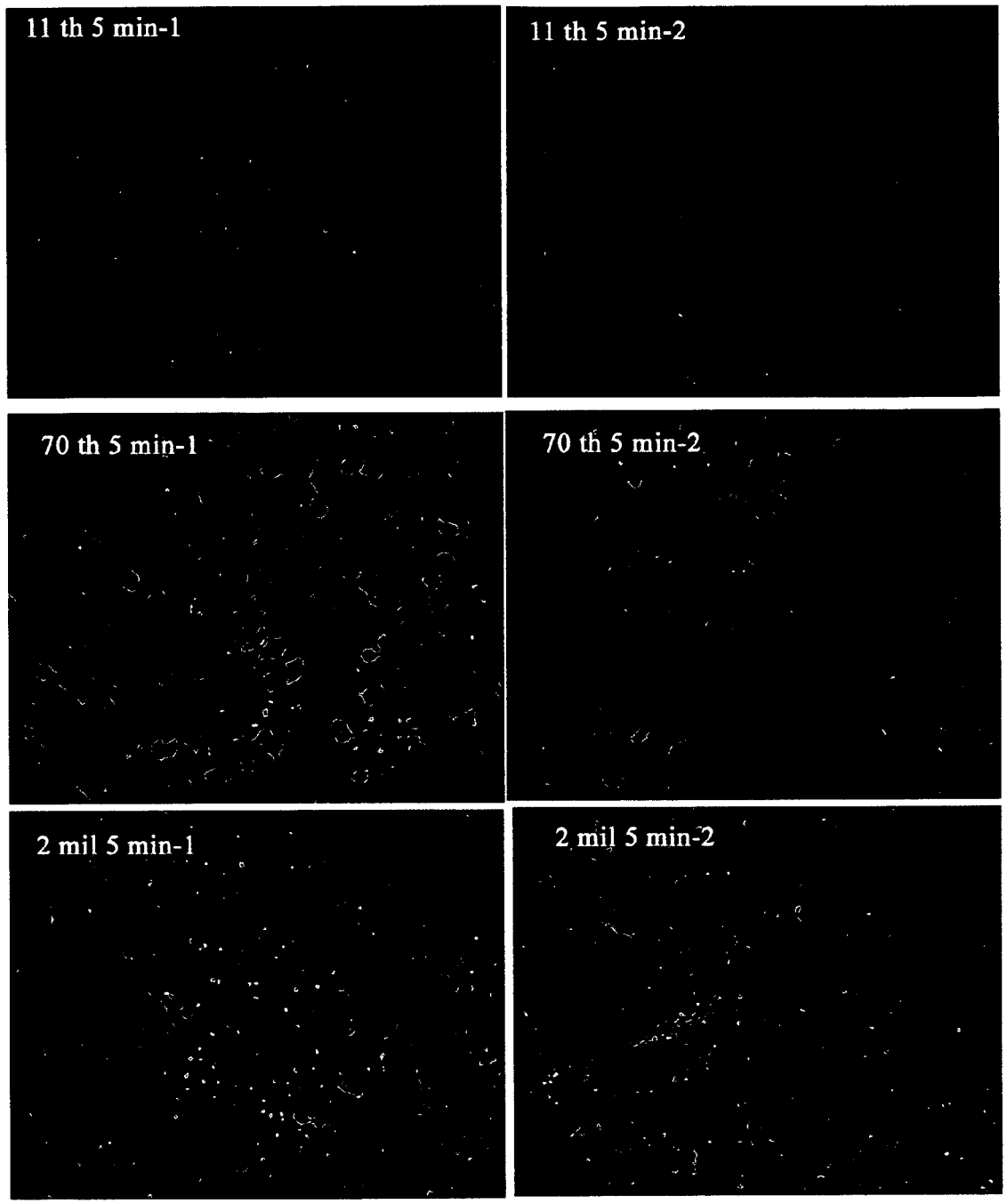
FIGS. 6A-6J.
  A. Distribution of rhodamine-labeled-dextran in mouse liver 5 min after delivery via injection into tail vein. Top panels show distribution of 11 kDa dextran. Middle panels show distribution of 70 kDa dextran. Bottom panels show distribution of 2,000 kDa dextran. Two representative pictures are shown for each dextran.
  B. Distribution of rhodamine-labeled-dextran in mouse liver 60 min after delivery via injection into tail vein. Top panels show distribution of 11 kDa dextran. Middle panels show distribution of 70 kDa dextran. Bottom panels show distribution of 2,000 kDa dextran. Two representative pictures are shown for each dextran.
  C. Distribution of rhodamine-labeled-dextran in mouse liver 60 min after direct injection into the liver. Top panels show control uninjected liver. Bottom panels show distribution of 70 kDa dextran. Two representative pictures are shown for each dextran.
  D. Distribution of Cy3-labeled bovine IgM in mouse liver 20 minutes after delivery via injection into tail vein. IgM is shown in black, actin and nuclei are shown in gray.
  E. Distribution of Streptavidin-NLS in mouse liver 5 minutes after delivery via injection into tail vein. Panel A shows actin staining. Panel B shows nuclei stained with ToPro3. Panel C shows Streptavidin-NLS localization. Panel D shows the merged pictures. Streptavidin-NLS is shown in black, actin and nuclei are shown in gray.
  F. Distribution of Streptavidin-NLS in mouse liver 60 minutes after delivery via injection into tail vein. Panel A shows actin staining. Panel B shows nuclei stained with ToPro3. Panel C shows Streptavidin-NLS localization.
Figure 6B:
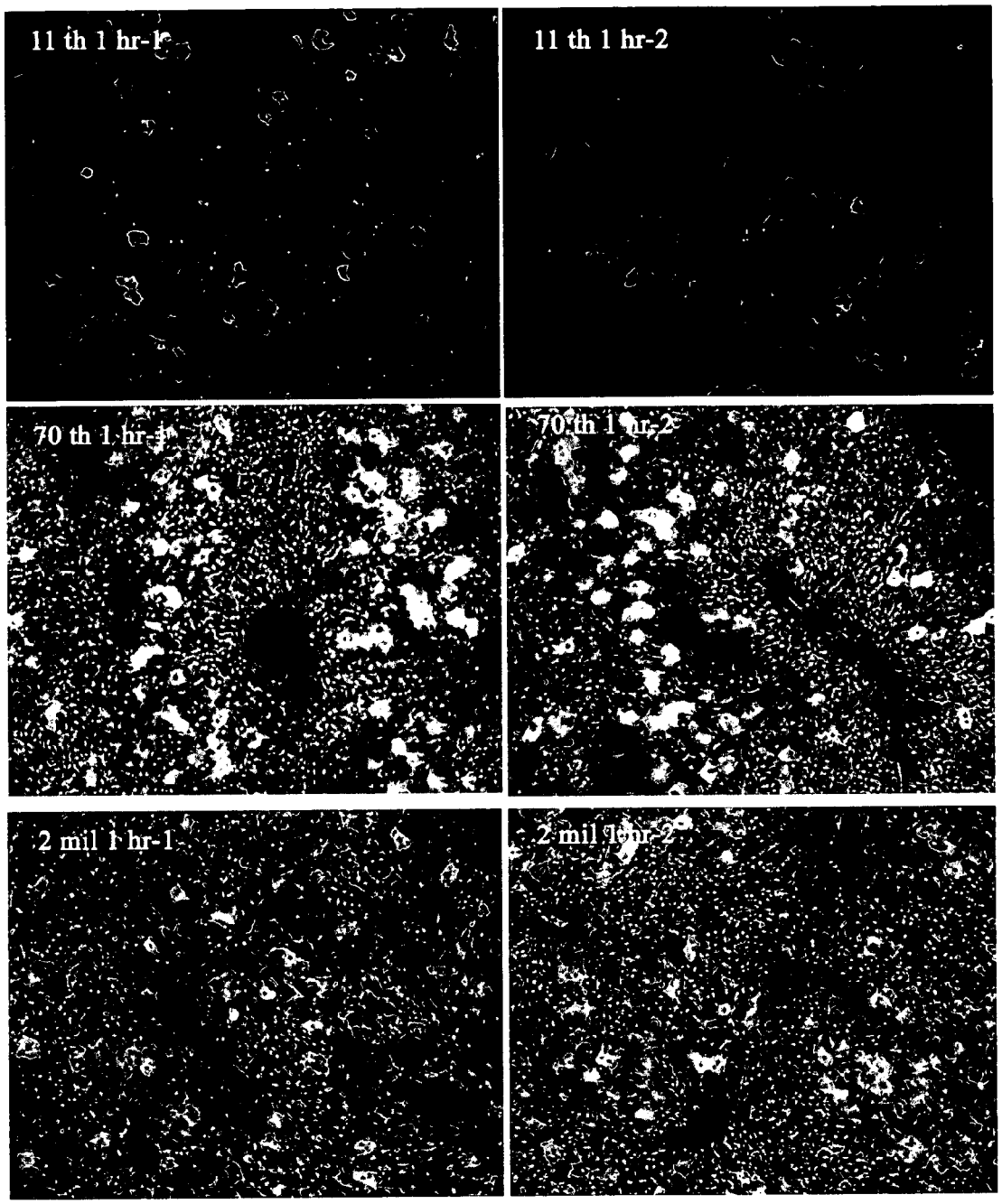
Figure 6C:
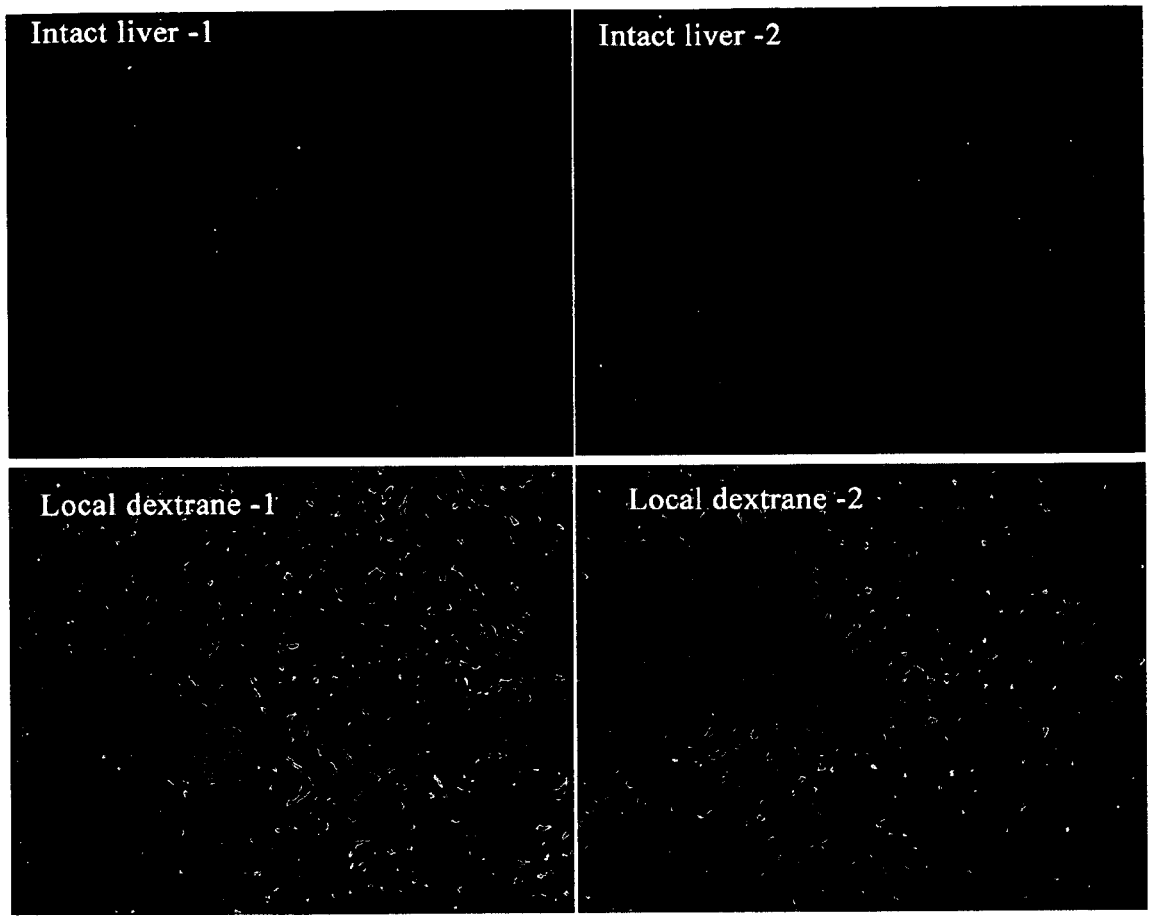
Figure 6D:
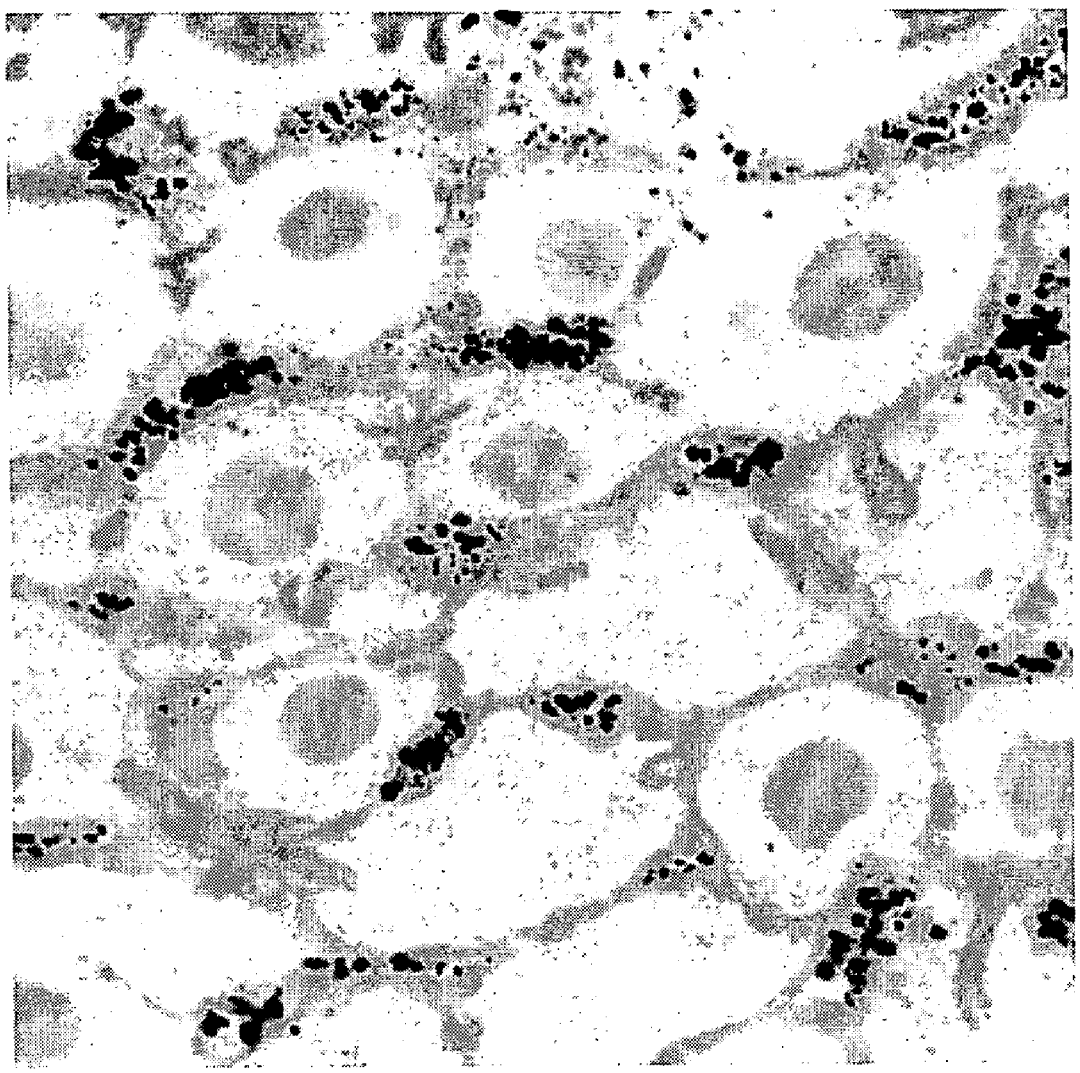
Figure 6E:
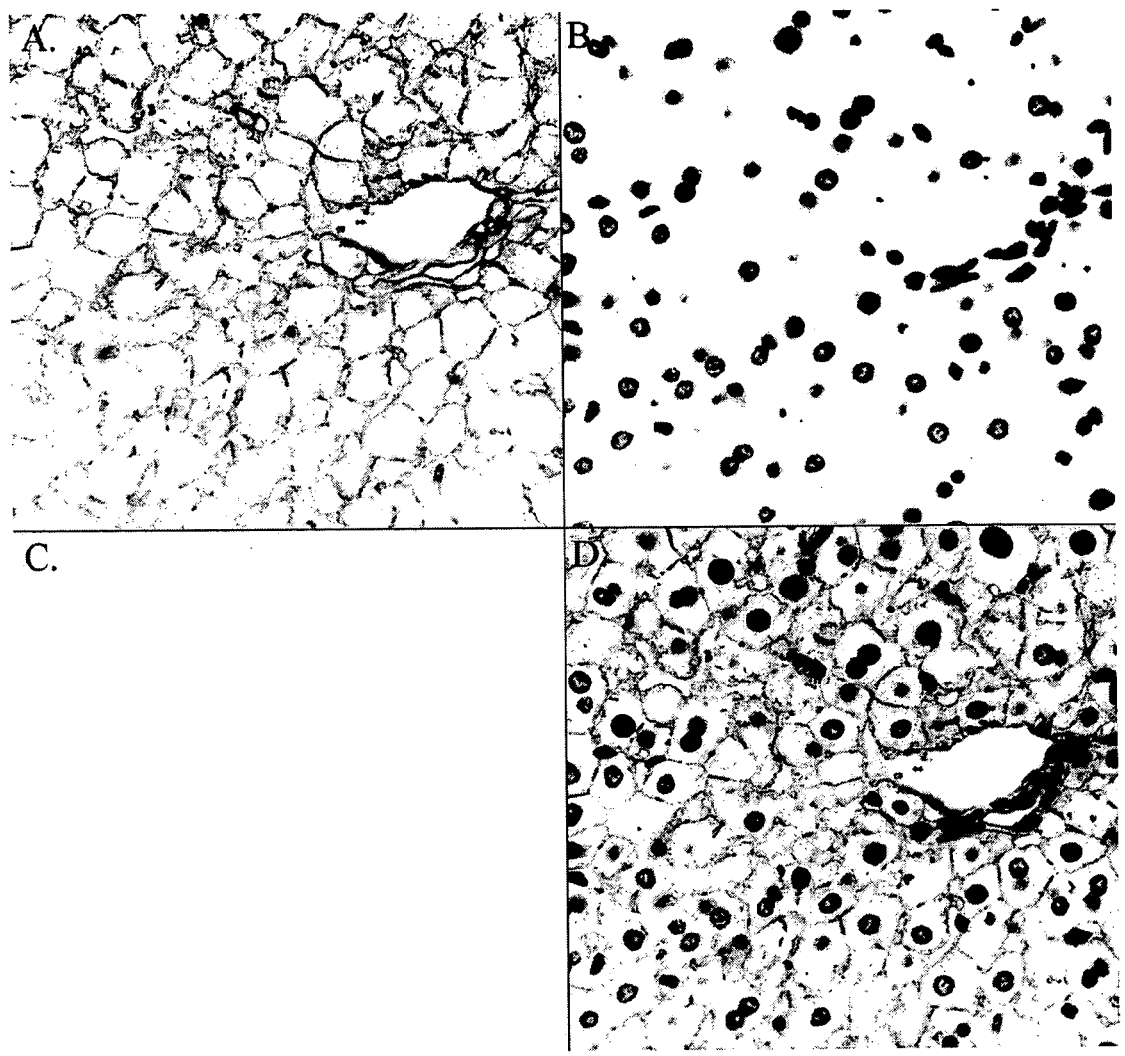
Figure 6F:
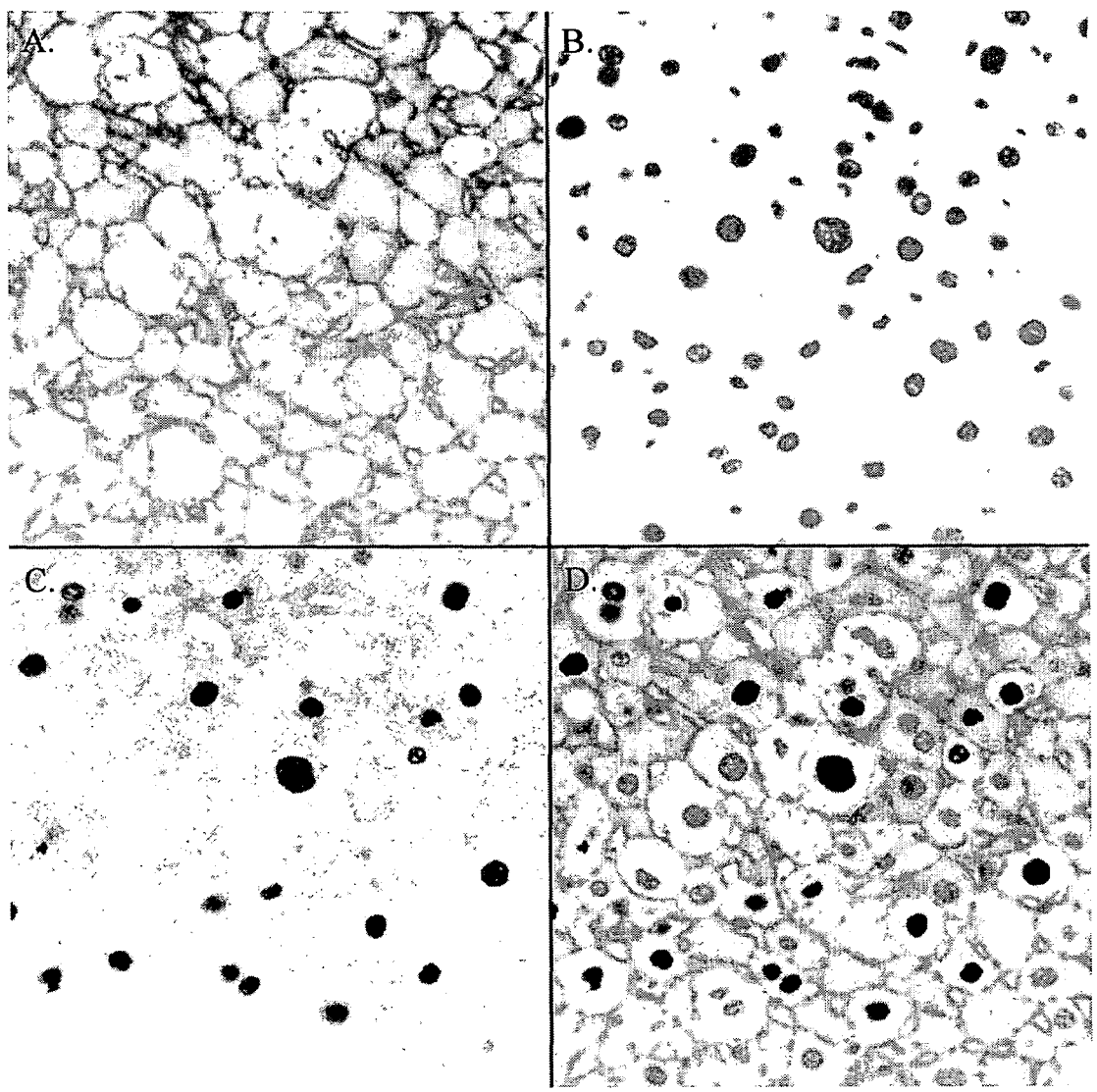
Figure 6G:
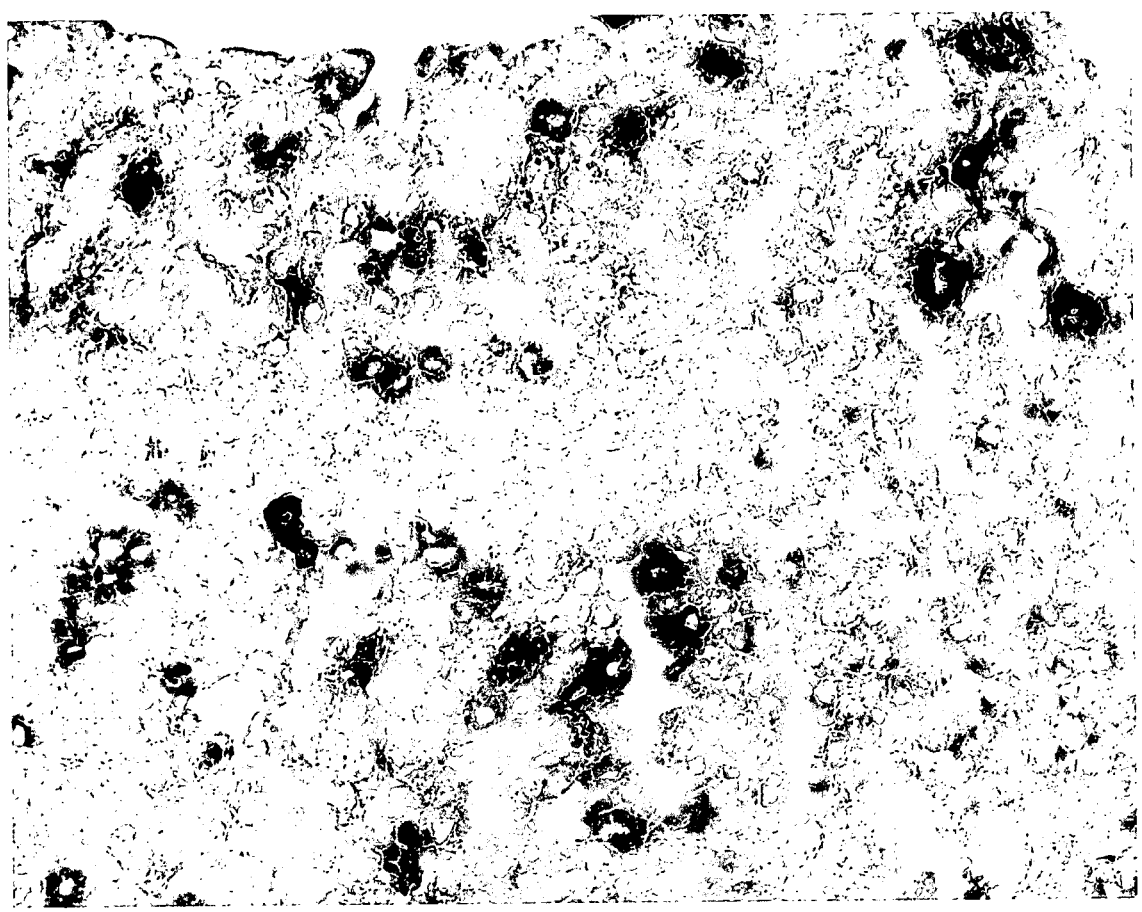
Figure 6H:
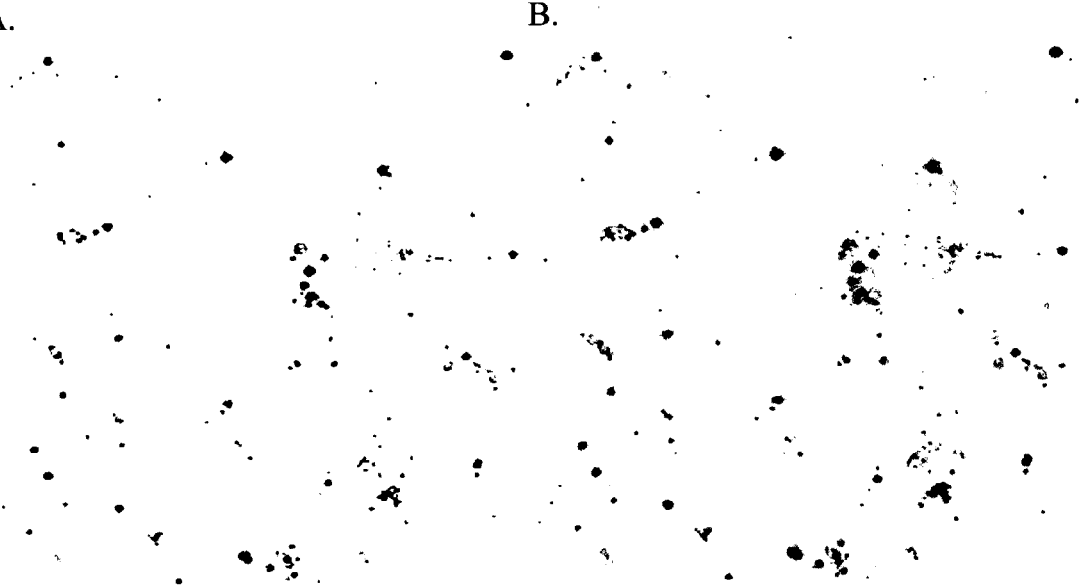
Figure 6I:
Figure 6J:
Figure 6K:
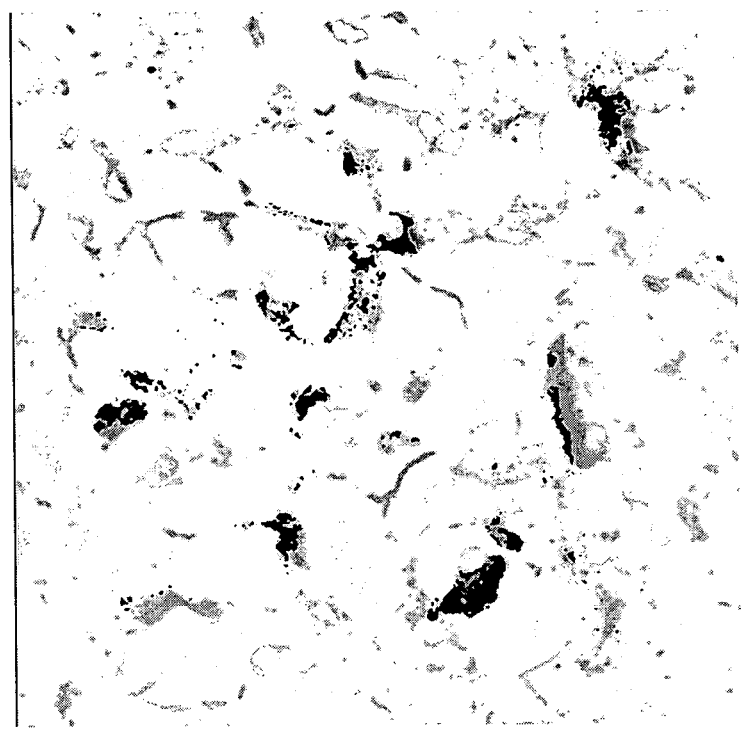
Figure 6L:
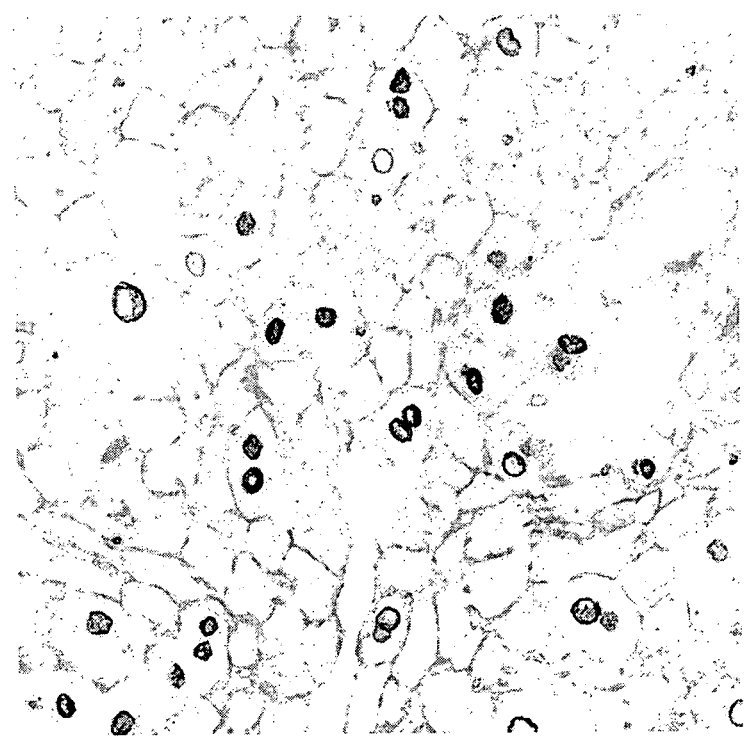
Figure 6M:
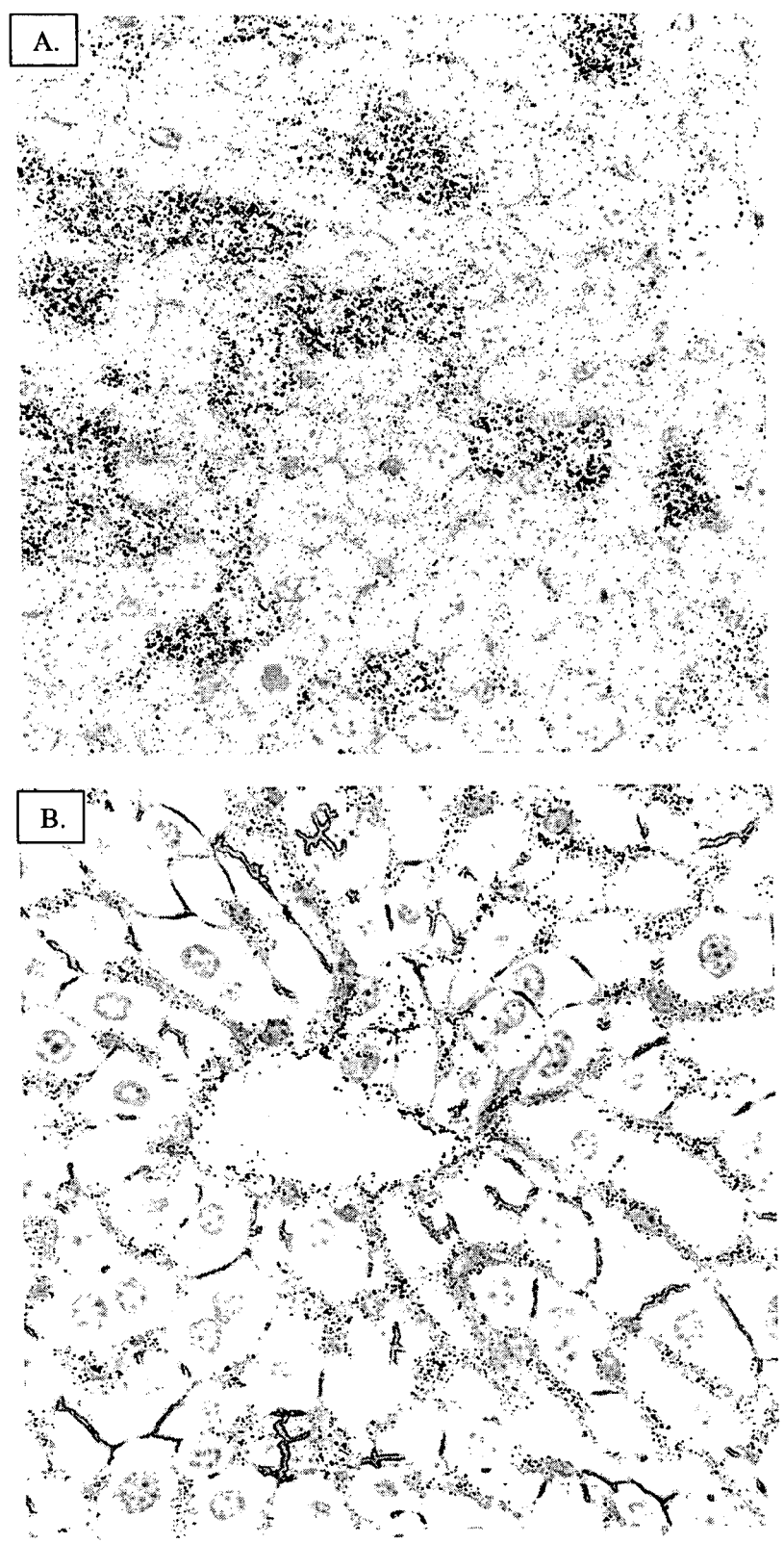

17. Delivery of small molecules and macromolecules to hepatocvtes via intravascular injection: ICR mice were injected with the following solutions:
1) 20 μg/ml fluorescently labeled Dextran (11K, 70K, or 2000K molecular weight) in Ringer's solution, (FIG. 6A and FIG. 6B).
2) 50 μg/ml pentameric Immunoglobulin M (ICN Biomedicals) labeled with Cy3-NHS ester (Amersham Pharmacia) in Ringer's solution, (FIG. 6D).
3) 4 μg/ml Streptavidin-NLS protein in Ringer's solution, (FIG. 6E and FIG. 6F).
4) 20 Rg/ml ,-galactosidase in Ringer's solution, (FIG. 6G).
5) 20 nm and 500 nm rhodamine-labeled polystyrene microspheres, (FIG. 6H and FIG. 6I).
6) 30 μl 1 mM BOBO-3 (Molecular Probes, Eugene, Ore.) nucleic acid stain in Ringer's solution. Control injection of 30 μl 1 mM BOBO in 0.25 mls, (FIG. 6J).
7) 20 μg Cy3-SV40 NLS peptide (SEQ ID #1: CKKKSSS-DDEATADSQHSTPPKKKRKVEDPKDFPSELLS) in Ringer's solution, (FIG. 6K).
8) 20 μg FITC-labeled anti-NUP62 monoclonal IgG (BD/Transduction Laboratories) Antibody binds to Nucleoporin 62, a protein component of nuclear pore complexes, (FIG. 6L).
9) $10^{11}$ pfu T7 20-6 phage in Ringer's solution. Control injections were in 0.25 ml Ringer's. T7 20-6 clone was selected for long circulation in the blood in vivo and has been shown to be resistant to complement inactivation and uptake by macrophages (REF). Phage was detected by immuno-histochemistry using purified IgG from a rabbit anti-T7 phage polyclonal serum and a Cy3-labeled anti-rabbit-IgG second antibody (Jackson ImmunoResearch Laboratories), (FIG. 6M).

Solutions containing the above listed molecules were injected into the tail vein of ICR mice using a 30 gauge, 0.5 inch needle. Injection volumes were 1 ml per 10 g animal body weight (~2.5 ml) unless otherwise stated. Injections were performed either manually or with a Harvard Apparatus Programmable Syringe Pump PHD 2000 with injection times of 3-5 sec. For comparison, BOBO-3 was also injected in a low volume, 0.25 ml. Five, 20, 60 or 120 min after injection, animals were sacrificed and livers were harvested for fluorescence microscopy analysis. 5 mm thick (approximate) sections of liver tissue were excised from the left lateral lobe and snap-frozen in O.C.T. compound. Liver sections (5-7 µm thick) were prepared using a Microm HM 505 N cryostat (Carl Zeiss), mounted on Superfrost Plus Fisher slides, air dried overnight and fixed in 4% formaldehyde for 20 min, followed by washing 3 times with PBS. Liver sections were examined using a Zeiss LSM 510 confocal microscope or an Axioplan-2 fluorescent microscope (Zeiss, Germany). Fluorescence was detected by using 560-615 nm BP, 505-550 nm BP and 650 nm LP filters. Some sections were counterstained with 16.5 nM Alexa546-Phalloidin, which binds to actin, and 13 nM ToPro3, which binds to DNA (both from Molecular Probes). These counter-stains were used to visualize cell peripheries and nuclei.

The results are shown in FIG. 6 The main target of these deliveries appeared to be hepatocytes, consistent with previous observations on reporter gene delivery. Delivery of small molecules (11 kDa dextran, BOBO3 and peptide), macromolecules (70 kDa dextran, 2000 kDa dextran, IgM, Streptavidin, β-galactosidase and) and even large supramolecular structures (20 nm & 500 nm polystyrene microspheres and T7 phage particles) demonstrates that a large number of molecules and complexes can be delivered using the described processes. Not only were the molecules delivered to the liver, they retained functional characteristics: streptavidin-NLS and BOBO-3 were transported to the nuclei of cells (FIG. 6C and 6G) and anti-NUP62 antibodies bound to endogenous NUP62 protein (FIG. 6I). Delivery of these compounds further demonstrates that the delivery of DNA and DNA complexes in the previous examples is indicative of the delivery one would expect for other molecules and complexes. Delivery via an intravascular route was unsuccessful if the volume of the injection solution was too low, as illustrated by the lack of delivery of either BOBO-3 or T7 phage clone 20-6 when injected in 0.25 mls (respectively, FIGS. 6G and 6J). Note that when T7 phage was injected in a low volume, phage was observed dispersed thoughout the liver, but there was little to no hepatocyte delivery. In contrast, when T7 phage was injected in 2.5 ml, extensive hepatocyte delivery was observed. FIG. 6C shows the distribution of 70 kDa dextran following direct injection into mouse liver, which resulted in little to no hepatocyte delivery 18. We show that Intravenous Injection Provides Effective Delivery of polynucleotide to Limb Skeletal Muscle.

A. lateral saphenous vein—120-140 g adult Sprague-Dawley rats were anesthetized with 80 mg/kg ketamine and 40 mg/kg xylazine and the surgical field was shaved and prepped with an antiseptic. The animals were placed on a heating pad to prevent loss of body heat during the surgical procedure. A 4 cm long abdominal midline incision was made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins as well as on the inferior vena cava near the bifurcation to block both outflow and inflow of the blood to the leg. An efflux enhancer solution (e.g., 0.5 mg papaverine in 3 ml saline) was injected into the external iliac artery though a 25 g needle. 1-10 minutes later, a 27 G butterfly needle was inserted into the lateral saphenous vein and 10.5 ml normal saline containing 500 µg pMIR48 plasmid DNA encoding firefly Luciferase was injected at a rate of 0.583 ml/sec. Fluid was injected in the direction of normal blood flow. The microvessel clips were removed 2 minutes after the injection and bleeding was controlled with pressure and gel foam. The abdominal muscles and skin were closed with 4-0 dexon suture.

| animal | Quad | Biceps | Hamstring | Gastroc | Shin | Foot | total |
|---|---|---|---|---|---|---|---|
| | | | Muscle tissue weight (g) | | | | |
| 1 | 2.13 | 1.07 | 1.89 | 1.31 | 0.62 | 0.09 | 7.1 |
| 2 | 2.01 | 1.02 | 1.43 | 1.18 | 0.20 | 0.06 | 5.9 |
| 3 | 1.32 | 1.11 | 1.12 | 1.36 | 0.43 | 0.16 | 5.5 |
| | | | Luciferase activity (relative light units) | | | | |
| 1 | 18510700 | 5633280 | 2421540 | 4058470 | 8732620 | 5240 | 39361850 |
| 2 | 44406070 | 20210730 | 15864580 | 3019110 | 27226910 | 27210 | 110754610 |
| 3 | 10689250 | 5126590 | 666520 | 1860300 | 1041520 | 4650 | 19388830 |
| | | | Luciferase (nanograms) | | | | |
| 1 | 1416.1 | 430.9 | 185.2 | 310.5 | 222.7 | 0.1 | 2565.5 |
| 2 | 3397.1 | 1546.1 | 1213.6 | 231.0 | 694.3 | 0.3 | 7082.4 |
| 3 | 817.7 | 392.2 | 51.0 | 142.3 | 26.6 | 0.0 | 1429.8 |
| mean | 1877.0 | 789.8 | 483.3 | 227.9 | 314.5 | 0.1 | 3692.5 |
| SEM | 779.4 | 378.4 | 367.2 | 48.6 | 198.1 | 0.1 | 1726.3 |
| | | | ng Luciferase/g Muscle | | | | |
| 1 | 664.8 | 402.8 | 98.0 | 237.0 | 359.2 | 0.6 | 360.8 |
| 2 | 1690.1 | 1515.8 | 848.7 | 195.7 | 3471.4 | 4.6 | 1200.4 |
| 3 | 619.5 | 353.3 | 45.5 | 104.6 | 61.8 | 0.3 | 260.0 |
| mean | 991.5 | 757.3 | 330.7 | 179.1 | 1297.5 | 1.8 | 607.1 |
| SEM | 349.6 | 379.5 | 259.4 | 39.1 | 1090.4 | 1.4 | 298.1 |

B. Medial saphenous vein injection—In this experiment we performed antegrade injections into the medial saphenous vein. 3 ml papaverine pretreatment, 500 µg pMIR48 plasmid DNA, 10 ml injection volume, 20 ml/min injection rate. This injection required an abdominal incision and an incision along the inside of the hind limb to expose the saphenous vein.

Microvessel clips were placed on the external iliac, caudal epigastric, internal iliac, deferent duct, and gluteal arteries and veins as well as on the inferior vena cava near the bifurcation to block both outflow and inflow of the blood to the leg. A pretreatment of papaverine (3.0 ml) was injected by hand into the saphenous vein (antegrade). 5 minutes later, a 27 gauge butterfly catheter was inserted into the saphenous vein and connected to a syringe pump. The 10 ml solution containing 500 µg plasmid DNA was delivered at a flow rate of 20 m/min. Transient swelling (increase in tissue size) throughout the limb was observed after the injection.

|  | Quad | Biceps | Hamstring | Gastroc | Shin | Foot | total |
| --- | --- | --- | --- | --- | --- | --- | --- |
| Tissue Weight (g) | 1.57 | 1.28 | 1.5 | 1.1 | 0.55 | 0.06 | 6.06 |
| Luciferase RLUs | 7016,230 | 69,733,530 | 8,775,140 | 14,942,710 | 3,289,150 | 4950 | 103,761,710 |
| Luciferase (ng) | 537 | 5335 | 671 | 1143 | 83.9 | 0.05 | 7770 |
| ng Luciferase/g Muscle | 342 | 4168 | 448 | 1039 | 152 | 0.8 | 1282 |

2.0-2.5ml papaverine pretreatment, 250 µg pMIR48 plamsid DNA, 5 ml injection volume, 10 ml/min injection rate. An incision was made extending from the groin to the ankle. A segment of the distal medial saphenous vein was dissected free and a clamped was placed on the distal vein. The proximal femoral vein and artery were also dissected free and clamped as well as the epigastric artery and vein. A pretreatment of papaverine (2.0-2.5 ml) was injected antegrade by hand into the saphenous vein. After 5 minutes, a 27 gauge butterfly needle catheter was inserted into the saphenous vein and connected to a syringe pump. 5.0 ml of plasmid DNA (250 µg) was then injected at a flow rate of 10 ml/min. The lower limb muscles were swollen (increase in tissue size) and some leakage occurred from the injection site as the injection progressed. After 2 minutes the clamps were removed and the vein allowed to reperfuse. Within several minutes the muscle regained a pink color and the vein returned to normal. The hole was sealed with gel foam.

C. Delivery of labeled dextran to limb skeletal muscle cells—An incision was made on the inside of the limb to expose the great saphenous vein and femoral vessels. Clamps were placed on the femoral artery and vein and the superficial caudal epigastic artery and vein. A 30-gauge needle catheter was inserted into the saphenous vein and secured with a microvascular clip. Papaverine (83 µg in 0.5 ml saline) was then injected by hand followed 5 minutes later by an injection of rhodamine labeled dextran (33 µg in 1.0 ml saline) at a flow rate of 4.5 ml/min. Two minutes after injection the clamps were removed and the limb was reperfused. 5 minutes after reperfusion, the muscle was harvested and frozen in OCT. FIG. 7 show the delivery of the dextran to skeletal muscle cells using this procedure.

19. Tissue Morphological Analysis.

A. Ringer's solution was injected into mouse tail vein using the procedure described above. The liver was immediately perfused with formalin/PBS, harvested, sectioned and analyzed by light microscopy (FIG. 8A). The figure shows the presence of vacuoles in hepatocytes, the enlargement of some cells, and greater separation between cells. A normal liver is shown for comparison (FIG. 8B). 24 h after injection, all animals exhibited normal liver morphology (data not shown).

B. Ringer's solution was injection into the iliac vein of rat using the procedure described above. Leg muscles were harvested prior to injection, and 5 min, 6 h and 24 h after injection. Muscles were then fixed, sectioned and analyzed by light microscopy. Normal muscle is shown in FIG. 9A. Samples

| animal | Quad | Biceps | Hamstring | Gastroc | Shin | Foot | total |
| --- | --- | --- | --- | --- | --- | --- | --- |
|  | Muscle tissue weight (g) | | | | | | |
| 1 | 2.09 | 1.00 | 1.30 | 1.13 | 0.65 | 0.08 | 6.25 |
| 2 | 1.59 | 1.16 | 1.18 | 1.20 | 0.68 | 0.07 | 5.88 |
| 3 | 1.72 | 1.01 | 1.52 | 1.06 | 0.48 | 0.09 | 5.88 |
|  | Luciferase activity (relative light units) | | | | | | |
| 1 | 151280 | 104060 | 6729270 | 7001820 | 4597130 | 4280 | 18587840 |
| 2 | 159400 | 119320 | 3099660 | 6752090 | 2675400 | 6890 | 12812760 |
| 3 | 30180 | 39880 | 1082720 | 7218640 | 2248320 | 2360 | 10622100 |
|  | Luciferase (nanograms) | | | | | | |
| 1 | 11.6 | 8.0 | 514.8 | 535.6 | 117.2 | 0.04 | 1187.2 |
| 2 | 12.2 | 9.1 | 237.1 | 516.5 | 68.2 | 0.07 | 843.3 |
| 3 | 2.3 | 3.1 | 82.8 | 552.2 | 57.3 | 0.02 | 697.8 |
| mean | 8.7 | 6.7 | 278.2 | 534.8 | 80.9 | 0.05 | 909.4 |
| SEM | 3.2 | 1.9 | 126.4 | 10.3 | 18.4 | 0.01 | 145.1 |
|  | ng Luciferase/g Muscle | | | | | | |
| 1 | 5.5 | 8.0 | 396.0 | 474.0 | 180.3 | 0.5 | 190.0 |
| 2 | 7.7 | 7.9 | 201.0 | 430.4 | 100.3 | 1.0 | 143.4 |
| 3 | 1.3 | 3.0 | 54.5 | 521.0 | 119.4 | 0.3 | 118.7 |
| mean | 4.8 | 6.3 | 217.1 | 475.1 | 133.4 | 0.6 | 150.7 |
| SEM | 1.9 | 1.6 | 98.9 | 26.1 | 24.1 | 0.2 | 20.9 | taken 5 min and 6 h after injection are shown in FIG. 9B and 9C respectively. At 5 min post injection one can observe the presence of vacuoles inside the muscle cells as well as greater separation between individual muscle cells (greater extravascular fluid volume). At 6 h post injection, the muscle tissue morphology is largely returned to normal. At 24 h post injection, the muscles exhibited normal morphology.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a protein or peptide to an extravascular cell in a mammalian target tissue in vivo comprising: inserting an injection solution containing the protein or peptide into the lumen of an efferent or afferent vessel of the target tissue wherein the inserting of the injection solution results in an increase in pressure in a vein of the target tissue of 10 mm Hg or greater thereby resulting in delivery of the protein or peptide to the extravascular cell.

2. The process of claim 1 wherein fluid flow out of the target tissue is occluded.

3. The process of claim 1 wherein the protein or peptide consists of a biologically active protein or peptide.

4. The process of claim 3 wherein the protein or peptide is greater than 5 kDa.

5. The process of claim 4 wherein the protein or peptide is greater than 30 kDa.

6. The process of claim 5 wherein the protein or peptide is greater than 500 kDa.

7. The process of claim 1 wherein the protein or peptide consists of a therapeutic molecule.

8. The process of claim 1 wherein the protein or peptide is in a complex.

9. The process of claim 1 wherein the injection solution contains a compound that increases vessel permeability.

10. The process of claim 9 wherein the compound consists of a vasodilator.

11. The process of claim 1 wherein the cell consists of a liver cell.

12. The process of claim 11 wherein the liver cell consists of a hepatocyte.

13. The process of claim 1 wherein the cell consists of a skeletal muscle cell.

14. The process of claim 1 wherein the cell consists of a heart muscle cell.

15. The process of claim 1 wherein the cell consists of a prostate cell.

16. The process of claim 1 wherein the vessel consists of a blood vessel.

17. The process of claim 16 wherein the blood vessel consists of an artery.

18. The process of claim 16 wherein the blood vessel consists of a vein.

19. The process of claim 1 wherein the vessel consists of a bile duct.

20. The process of claim 1 wherein the injection solution contains less than 20 mM salt.

21. The process of claim 20 wherein the injection solution contains less than 5 mM salt.

22. The process of claim 1 wherein the injection solution contains zwitterions.

23. The process of claim 1 wherein the injection solution is hypotonic.

24. The process of claim 1 wherein the injection solution is hypertonic.

25. A process for delivering a protein or peptide to an extravascular in vivo mammalian cell in a target tissue comprising: rapidly inserting a sufficient volume of injection solution containing the protein or peptide into the lumen of an efferent or afferent vessel of the target tissue and impeding fluid flow away from the tissue during the injection wherein the inserting of the injection solution results in an increase in pressure in a vein of the target tissue of 10 mm Hg or greater thereby resulting in delivery of the protein or peptide to the extravascular mammalian cell in the tissue.

* * * * *

SEQUENCE LISTING

```
<160> NUMBER OF SEQ ID NOS: 1

<210> SEQ ID NO 1
<211> LENGTH: 39
<212> TYPE: PRT
<213> ORGANISM: Simian virus 40

<400> SEQUENCE: 1

Cys Lys Lys Lys Ser Ser Ser Asp Asp Glu Ala Thr Ala Asp Ser Gln
1               5                   10                  15

His Ser Thr Pro Pro Lys Lys Lys Arg Lys Val Glu Asp Pro Lys Asp
            20                  25                  30

Phe Pro Ser Glu Leu Leu Ser
            35
```